US006395472B1

(12) United States Patent
Leary et al.

(10) Patent No.: US 6,395,472 B1
(45) Date of Patent: *May 28, 2002

(54) METHODS OF UTILIZING THE TT VIRUS

(75) Inventors: Thomas P. Leary, Kenosha, WI (US); James Erker, Hainesville, IL (US); Michelle Chalmers, Lake Villa, IL (US); John Simons, Grayslake, IL (US); Larry Birkenmeyer, Chicago, IL (US); Scott Muerhoff, Kenosha, WI (US); Tami Pilot-Matias, Green Oaks, IL (US); Suresh Desai, Libertyville, IL (US); Isa Mushahwar, Grayslake, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/245,248

(22) Filed: Feb. 5, 1999

(51) Int. Cl.[7] ................................................. C12Q 1/70
(52) U.S. Cl. .............................. 435/5; 435/6; 435/91.2; 536/24.3; 536/24.32; 536/24.33
(58) Field of Search ........................... 536/24.3, 24.32, 536/24.33; 435/5, 6, 91.2, 975; 29/52–71

(56) References Cited

U.S. PATENT DOCUMENTS

| 4,683,195 | A | 7/1987 | Mullis et al. |
| 4,683,202 | A | 7/1987 | Mullis |
| 5,427,930 | A | 6/1995 | Birkenmeyer et al. |

FOREIGN PATENT DOCUMENTS

| EP | 0320308 | 6/1989 |
| EP | 0439182 | 7/1991 |
| EP | 1 010 759 | 6/2000 |
| WO | 9320227 | 10/1993 |
| WO | 9905282 | 2/1999 |
| WO | 99 58638 | 11/1999 |

OTHER PUBLICATIONS

Nishizawa et al., *Biochem And Biophysical Res Commun* 241:92–97 (1997).
Okamoto et al., *Hepatology Res.* 10:1–16 (1998).
Simmonds et al., *The Lancet* 352:191–194 (1998).
Naoumov et al., *The Lancet* 352:195–197 (1998).
Desai et al., *The Journal of Infectious Diseases* In press: (1999).
Takahashi et al., *Hepatology Res.* 12:233–239 (1998).
Okamoto et al., *Journal of Medical Virology* 56:128–132 (1998).
Charlton et al., *Hepatology* 28:839–842 (1998).
Muzyczka, N., *Current Topics in Microbiology and Immunology* 158:97–129 (1992).
Kotin, R.M. *Human Gene Therapy* 5:793–801 (1994).
Haj–Ahmad et al., *Journal of Virology* 57:264–274 (1986).
Berkner K.L., *Biotechniques* 6:619–629 (1988).
Breakefield et al., *The New Biologist* 3:203–218 (1991).
Wolfe et al., *Nature Genetics* 1:379–384 (1992).
Grossi et al., *Archives of Virology* 102:275–283 (1988).
Milanesi et al., *Molecular and Cellular Biology*, 4:1551–1560 (1984).
Gazit et al., *Journal of Virology* 60:19–28 (1986).
Palmer et al., *Proc. Natl. Acad. Sci. USA* 84:1055–1059 (1987).
Takahashi, K. et al., "Partial–2.4–KB Sequences of TT Virus (TTV) Genome from eight Japanese Isolates: Diagnostic and Phylogenetic Implications", *Hepatology Research* 12:111–120 (1998).
Simmonds, P. et al., "Detection of a novel DNA virus (TTV) in blood donors and blood products", *The Lancet* 352:191–197 (1998).

*Primary Examiner*—Donna Wortman
*Assistant Examiner*—Robert A. Zeman
(74) *Attorney, Agent, or Firm*—Cheryl L. Becker

(57) ABSTRACT

The present invention relates to nucleic oligomer primers or probes useful for detection of TTV in test samples. Also provided are assays which utilize these primers and probes, as well as test kits which contain these oligomer primers and/or probes. In addition, the present invention encompasses the use of TTV nucleotide sequences as nucleic acid vectors and as markers for determining transmission between individuals as well as the route thereof. Additionally, the present invention encompasses a method of detecting TTV infection prior to xenotransplatation of a tissue or organ.

35 Claims, 11 Drawing Sheets

SEQUENCE LISTING

<160> NUMBER OF SEQ ID NOS: 71

<210> SEQ ID NO 1
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: A5430 primer

<400> SEQUENCE: 1
cagacagagg agaaggcaac atg                                              23

<210> SEQ ID NO 2
<211> LENGTH: 22
<212> TYPE: DNA
<213> ORGANISM: Homo sapien
<220> FEATURE:
<221> NAME/KEY: primer_bind
<222> LOCATION: (0)...(0)
<223> OTHER INFORMATION: A5427m primer
<221> NAME/KEY: misc_feature
<222> LOCATION: (6)...(6)
<223> OTHER INFORMATION: y = t/u or c at position 6
<221> NAME/KEY: misc_feature
<222> LOCATION: (21)...(21)
<223> OTHER INFORMATION: w = a or t/u at position 21

<400> SEQUENCE: 2
taccayttag ctctcattct wa                                               22

<210> SEQ ID NO 3
<211> LENGTH: 24
<212> TYPE: DNA
<213> ORGANISM: Homo sapien
<220> FEATURE:
<221> NAME/KEY: primer_bind
<222> LOCATION: (0)...(0)
<223> OTHER INFORMATION: A8761 primer
<221> NAME/KEY: misc_feature
<222> LOCATION: (3)...(3)
<223> OTHER INFORMATION: m = a or c at position 3
<221> NAME/KEY: misc_feature
<222> LOCATION: (6)...(6)
<223> OTHER INFORMATION: y = t/u or c at position 6
<221> NAME/KEY: misc_feature
<222> LOCATION: (10)...(10)
<223> OTHER INFORMATION: y = t/u or c at position 10
<221> NAME/KEY: misc_feature
<222> LOCATION: (12)...(12)
<223> OTHER INFORMATION: r = g or a at position 12

<400> SEQUENCE: 3
ggmaayatgy trtggataga ctgg                                             24

<210> SEQ ID NO 4
<211> LENGTH: 21
<212> TYPE: DNA

```
<213> ORGANISM: Homo sapien
<220> FEATURE:
<221> NAME/KEY: primer_bind
<222> LOCATION: (0)...(0)
<223> OTHER INFORMATION: A5432 primer

<400> SEQUENCE: 4
ctacctcctg gcattttacc a                                              21

<210> SEQ ID NO 5
<211> LENGTH: 22
<212> TYPE: DNA
<213> ORGANISM: Homo sapien
<220> FEATURE:
<221> NAME/KEY: primer_bind
<222> LOCATION: (0)...(0)
<223> OTHER INFORMATION: B19-Forward primer
<221> NAME/KEY: misc_feature
<222> LOCATION: (13)...(13)
<223> OTHER INFORMATION: y = t/u or c at position 13

<400> SEQUENCE: 5
gatggtgcaa acytttgcct cc                                             22

<210> SEQ ID NO 6
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: B19-Reverse primer

<400> SEQUENCE: 6
gcatgacttc agttaattct gca                                            23

<210> SEQ ID NO 7
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: TTVjs-s1 primer

<400> SEQUENCE: 7
agacagagga gaaggcaaca                                                20

<210> SEQ ID NO 8
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: TTVjs-a1 primer

<400> SEQUENCE: 8
gaccaaaaca tacacatgaa                                                20

<210> SEQ ID NO 9
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: B19.1699-s1 primer
```

-continued

```
<400> SEQUENCE: 9
gtaagcggga acactacaac                                              20

<210> SEQ ID NO 10
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: B19.2119-a1 primer

<400> SEQUENCE: 10
cggaggaaac tgggcttccg                                              20

<210> SEQ ID NO 11
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: TTV-specific primer

<400> SEQUENCE: 11
ctagctgcac ttccgaatgg ctg                                          23

<210> SEQ ID NO 12
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: TTV-specific primer

<400> SEQUENCE: 12
ggtactgttg gtcattgcga ggtgg                                        25

<210> SEQ ID NO 13
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: TTV-specific primer

<400> SEQUENCE: 13
gtgaagccac ggagggagat cag                                          23

<210> SEQ ID NO 14
<211> LENGTH: 24
<212> TYPE: DNA
<213> ORGANISM: Homo sapien
<220> FEATURE:
<221> NAME/KEY: primer_bind
<222> LOCATION: (0)...(0)
<223> OTHER INFORMATION: A1 primer

<400> SEQUENCE: 14
cctggcatct ttccatttcc aaag                                         24

<210> SEQ ID NO 15
<211> LENGTH: 25
<212> TYPE: DNA
<213> ORGANISM: Homo sapien
```

```
<220> FEATURE:
<221> NAME/KEY: primer_bind
<222> LOCATION: (0)...(0)
<223> OTHER INFORMATION: S2 primer

<400> SEQUENCE: 15
gactggctaa ctaaagatac ctcag                                          25

<210> SEQ ID NO 16
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: A2 primer

<400> SEQUENCE: 16
tccaaagtta aaactgtagg gtacg                                          25

<210> SEQ ID NO 17
<211> LENGTH: 24
<212> TYPE: DNA
<213> ORGANISM: Homo sapien
<220> FEATURE:
<221> NAME/KEY: primer_bind
<222> LOCATION: (0)...(0)
<223> OTHER INFORMATION: N22-A1 primer

<400> SEQUENCE: 17
gggtctgtgt gtactaagag ttgg                                           24

<210> SEQ ID NO 18
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: N22-A2 primer

<400> SEQUENCE: 18
aaagtctggc attcatgtgt atg                                            23

<210> SEQ ID NO 19
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: Anchored primer N22-S1

<400> SEQUENCE: 19
gccaggaggt agcagcaatg tgc                                            23

<210> SEQ ID NO 20
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: Anchored primer N22-S2

<400> SEQUENCE: 20
ctattagaat gagagctaag tggtacc                                        27
```

<210> SEQ ID NO 21
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: UFGH1-A1 primer

<400> SEQUENCE: 21
gctaagtaca cttgagtacc attgc                                    25

<210> SEQ ID NO 22
<211> LENGTH: 25
<212> TYPE: DNA
<213> ORGANISM: Homo sapien
<220> FEATURE:
<221> NAME/KEY: protein_bind
<222> LOCATION: (0)...(0)
<223> OTHER INFORMATION: UFGH1-A2 primer

<400> SEQUENCE: 22
ggtactgttg gtcattgcga ggtgg                                    25

<210> SEQ ID NO 23
<211> LENGTH: 24
<212> TYPE: DNA
<213> ORGANISM: Homo sapien
<220> FEATURE:
<221> NAME/KEY: primer_bind
<222> LOCATION: (0)...(0)
<223> OTHER INFORMATION: DFGH1-S1 primer

<400> SEQUENCE: 23
ctggaaggaa gagtatgagg cctg                                     24

<210> SEQ ID NO 24
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: DFGH1-S2 primer

<400> SEQUENCE: 24
ccctagaggc aatctaagag acacc                                    25

<210> SEQ ID NO 25
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: UFTTV1 primer

<400> SEQUENCE: 25
agccttttgt ggggtctgtg tgtacta                                  27

<210> SEQ ID NO 26
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: DFTTV1 primer

<400> SEQUENCE: 26
tggaaatggt aaaatgccag gaggtag                                27

<210> SEQ ID NO 27
<211> LENGTH: 28
<212> TYPE: DNA
<213> ORGANISM: Homo sapien
<220> FEATURE:
<221> NAME/KEY: primer_bind
<222> LOCATION: (0)...(0)
<223> OTHER INFORMATION: UFTTV2 primer

<400> SEQUENCE: 27
gtctggcatt catgtgtatg ttttggtc                               28

<210> SEQ ID NO 28
<211> LENGTH: 28
<212> TYPE: DNA
<213> ORGANISM: Homo sapien
<220> FEATURE:
<221> NAME/KEY: primer_bind
<222> LOCATION: (0)...(0)
<223> OTHER INFORMATION: DFTTV2 primer

<400> SEQUENCE: 28
gcagcaatgt gcctattaga atgagagc                               28

<210> SEQ ID NO 29
<211> LENGTH: 3852
<212> TYPE: DNA
<213> ORGANISM: Homo sapien

<400> SEQUENCE: 29
tttgtgctac gtcactaacc acgtgacgcc cacaggccaa ccgaatgcta tgtcgtgcac    60
ttcctgggcc gggtctacgt cctgatataa ctagctgcac ttccgaatgg ctgagttttc   120
cacgcccgtc cgcagcggtg aagccacgga gggagatcag cgcgtcccga gggcgggtgc   180
cggaggtgag tttacacacc ggagtcaagg ggcaattcgg gctcgggact ggccgggcta   240
tgggcaaggc tctgaaaaaa gcatgtttat cggcaggcat tacagaaaga aaagggcgct   300
gtcactgctt gctgtgcgaa caacacagaa ggctcgcaaa ctactaatag tgatgtggac   360
cccacctcgc aatgaccaac agtacctcaa ctggcaatgg tactcaagtg tacttagctc   420
ccacgctgct atgtgcgggt gtcccgacgc tgtcgctcat tttaatcatc ttgcttctgt   480
gcttcgcgcc ccgcaaaatc caccccgcc cggtccccag cgaaacctgc ccctccgacg   540
gctgccagct ctcccggctg cgccagaggc gcccggagat agagcaccat ggcctatggc   600
tggtggcgcc gaaggagaag aaggtggcgc agtggcgac gcagaccatg gaggcgccgc   660
tggaggaccc gaagacgcag acctgctaga cgccgtggcc gccgcagaaa cgtaaggaga   720
cggcgccgag gagggaggtg gaggaggagg tacaggagat ggaaaagaaa gggcaggcgg   780
agaaagaaag ctaaaataat aataagacaa tggcaaccaa actacaggag gagatgtaac   840
atagtgggct acattcccgt actgatatgt ggcgaaaata ctgtcagcag aaactatgcc   900
acacactcag acgataccaa ctacccagga ccctttgggg gggtatgac tacagacaaa     960
tttactctaa gaatcctgta tggtgagtac aagaggttta tgaactactg gacagcatct  1020
aacgaagatc tagacctctg tagatatctg ggagtaaacc tgtacttttt cagacaccca  1080
gatgtagact ttatcataaa gataaatact atgcctcctt tcttagacac agaactcaca  1140

```
gcccctagca tacacccagg catgctagcc ttagacaaga gagcaaggtg gatacccagc    1200
ttaaaatcta gaccgggaaa aaagcactat attaagataa gagtaggggc acctaaaatg    1260
ttcacagata agtggtaccc ccaaacagac ctctgtgaca tggtgctgct aaccgtctat    1320
gcgaccgcag cggatatgca atatccgttc ggctcaccac taactgactc tgtggttgtg    1380
aacttccagg ttctgcaatc catgtatgat gaaaaaatta gcatattacc agacgaaaaa    1440
atccaaagac aaaacctatt aactagtata tcaaactata ttcctttcta taataccaca    1500
cagacaatag ctcagctaaa accatttgta gatgcaggca atgcaatatc aggaacaacc    1560
acaacaacat ggggatcact actaaacaca accaaattca caactacaac taccaccaca    1620
tacacttacc caggtacaac aaacacaaca gtaactttta taacagctaa tgacagctgg    1680
tacagaggca cagtatacaa ccaaaacata aaagacgtag caaaaaaagc agcagaacta    1740
tactcaaaag caacaaaagc tgtactagga aacacattca ctacagaaga ttatacacta    1800
ggataccacg gaggcctata tagctccata tggctatccc ccggtagatc ttactttgaa    1860
acaccaggag catacacaga cataaaatat aatccttta cagacagagg agaaggaaac    1920
atgctgtgga tagactggct aagcaaaaaa aatatgaact atgacaaagt acaaagtaaa    1980
tgcctaatat cagacctacc tctgtgggca gcagcatatg gctatgtaga attctgtgca    2040
aaaagcacag gagaccaaaa catacacatg aatgccagac ttttaataag aagtcccttt    2100
acagaccccc aactcttagt acacacagac cccaccaaag gctttgttcc ttactcccta    2160
aattttggaa atggtaaaat gccaggaggt agcagcaatg tgcctattag aatgagagct    2220
aagtggtacc ccacactact tcaccagcaa gaagtactag aggccttagc acagtcaggc    2280 cccttttgcat accacgcaga cattaaaaaa gtatctctgg gtatgaaata ccgttttaag    2340
tggatctggg gtggaaaccc cgttcgccaa caggttgtta gaaatccctg caaagaaacc    2400
cactcctcgg gcaatagagt ccctagaagc ttacaaatcg ttgacccgaa atacaactca    2460
ccggaactca ctttccatac ctgggacttc aaacgtggcc tctttggccc gaaagctatt    2520
cagagaatgc aacaacaacc aacaactact gacattttt cagcaggccg caagagaccc    2580
aggagggaca ccgaggtgta ccactccagc caagaagggg agcaaaaaga agcttactt    2640 ttcccccag tcaagctcct cagacgagtc ccccgtggg aagactcgca gcaggaggaa    2700
agcgggtcgc aaagctcaga ggaagagacg cagaccgtct cccagcagct caagcagcag    2760
ctgcagcaac agcgaatcct gggagtcaaa ctcagactcc tgttcaacca gtccaaaaa    2820 atccaacaaa atcaagatat caaccctacc ttgttaccaa ggggggggga tctagcatcc    2880
ttatttcaaa tagcaccata aacatgtttg gagaccccaa accctacaac ccttccagta    2940
atgactggaa ggaagagtat gaggcctgta artactggga cagacccct agaggcaatc    3000 taagagacac cccctactac ccctgggccc caaggagaa ccagtaccgt gtaaacttta    3060
agcttggatt tcaataaagc taggccgtgg gactttcact tgtcggtgtc tgcttataaa    3120
ggtcaccaag cactccgagc ggagcgagga gtgcgaccct tggggctca acgccttcgg    3180 agccgcgcgc tacgccttcg gctgcgcgcg gcacctcaga ccccgctcg tgctgacgcg    3240 ctcgcgcgcg tcagaccact tcgggcttgc ggggtcggg aaatttgcta aacagactcc    3300
gagttgccat tggacactgg agctgtgaat cagtaacgaa agtgagtggg gccagacttc    3360
gccataaggc cttatcttc tcgccatttg tcagtgtcgg gggtcgcgt aggcttcggc    3420 ctccattta gggcctaaaa actaccaaaa tggccgttcc agtgacgtca cagccgccat    3480
tttaagtagc tgacgtcaag gattgacgtg aaggttaaag gtcatcctcg gcggaagcta    3540
```

```
cacaaaatgg tggacaacat cttccgggtc aaaggtcgtg cacacgtcat aagtcacgtg    3600
gtggggaccc gctgtaaccc ggaagtaggc cccgtcacgt gatttgtcac gtgtgtacac    3660
gtcaccgccg ccattttgtt ttacaaaatg gccgacttcc ttcctctttt ttaaaaaaag    3720
gcgccaaaaa accgtcggcg ggggggccgc gcgctgcgcg cgcggccccc ggggaggca    3780 ttgcctcccc cccccgcgcg catgcgcgcg ggtccccccc cctccggggg gctccgcccc    3840
ccggcccccc cc                                                        3852
```

<210> SEQ ID NO 30
<211> LENGTH: 202
<212> TYPE: PRT
<213> ORGANISM: Homo sapien

<400> SEQUENCE: 30

```
Met Ala Glu Phe Ser Thr Pro Val Arg Ser Gly Glu Ala Thr Glu Gly
  1               5                  10                  15

Asp Gln Arg Val Pro Arg Ala Gly Ala Gly Gly Glu Phe Thr His Arg
                 20                  25                  30

Ser Gln Gly Ala Ile Arg Ala Arg Asp Trp Pro Gly Tyr Gly Gln Gly
             35                  40                  45

Ser Glu Lys Ser Met Phe Ile Gly Arg His Tyr Arg Lys Lys Arg Ala
 50                  55                  60

Leu Ser Leu Leu Ala Val Arg Thr Thr Gln Lys Ala Arg Lys Leu Leu
 65                  70                  75                  80

Ile Val Met Trp Thr Pro Pro Arg Asn Asp Gln Gln Tyr Leu Asn Trp
                 85                  90                  95

Gln Trp Tyr Ser Ser Val Leu Ser Ser His Ala Ala Met Cys Gly Cys
            100                 105                 110

Pro Asp Ala Val Ala His Phe Asn His Leu Ala Ser Val Leu Arg Ala
        115                 120                 125

Pro Gln Asn Pro Pro Pro Gly Pro Gln Arg Asn Leu Pro Leu Arg
    130                 135                 140

Arg Leu Pro Ala Leu Pro Ala Ala Pro Glu Ala Pro Gly Asp Arg Ala
145                 150                 155                 160

Pro Trp Pro Met Ala Gly Gly Ala Glu Gly Glu Gly Gly Ala Gly
                165                 170                 175

Gly Asp Ala Asp His Gly Gly Ala Ala Gly Gly Pro Glu Asp Ala Asp
            180                 185                 190

Leu Leu Asp Ala Val Ala Ala Ala Glu Thr
        195                 200
```

<210> SEQ ID NO 31
<211> LENGTH: 770
<212> TYPE: PRT
<213> ORGANISM: Homo sapien

<400> SEQUENCE: 31

```
Met Ala Tyr Gly Trp Trp Arg Arg Arg Arg Arg Trp Arg Arg Trp
  1               5                  10                  15

Arg Arg Arg Pro Trp Arg Arg Arg Trp Arg Thr Arg Arg Arg Arg Pro
                 20                  25                  30

Ala Arg Arg Arg Gly Arg Arg Arg Asn Val Arg Arg Arg Arg Gly
             35                  40                  45

Gly Arg Trp Arg Arg Arg Tyr Arg Arg Trp Lys Arg Lys Gly Arg Arg
 50                  55                  60
```

-continued

```
Arg Lys Lys Ala Lys Ile Ile Ile Arg Gln Trp Gln Pro Asn Tyr Arg
 65                  70                  75                  80

Arg Arg Cys Asn Ile Val Gly Tyr Ile Pro Val Leu Ile Cys Gly Glu
                 85                  90                  95

Asn Thr Val Ser Arg Asn Tyr Ala Thr His Ser Asp Asp Thr Asn Tyr
                100                 105                 110

Pro Gly Pro Phe Gly Gly Gly Met Thr Thr Asp Lys Phe Thr Leu Arg
                115                 120                 125

Ile Leu Tyr Gly Glu Tyr Lys Arg Phe Met Asn Tyr Trp Thr Ala Ser
130                 135                 140

Asn Glu Asp Leu Asp Leu Cys Arg Tyr Leu Gly Val Asn Leu Tyr Phe
145                 150                 155                 160

Phe Arg His Pro Asp Val Asp Phe Ile Ile Lys Ile Asn Thr Met Pro
                165                 170                 175

Pro Phe Leu Asp Thr Glu Leu Thr Ala Pro Ser Ile His Pro Gly Met
                180                 185                 190

Leu Ala Leu Asp Lys Arg Ala Arg Trp Ile Pro Ser Leu Lys Ser Arg
                195                 200                 205

Pro Gly Lys Lys His Tyr Ile Lys Ile Arg Val Gly Ala Pro Lys Met
                210                 215                 220

Phe Thr Asp Lys Trp Tyr Pro Gln Thr Asp Leu Cys Asp Met Val Leu
225                 230                 235                 240

Leu Thr Val Tyr Ala Thr Ala Ala Asp Met Gln Tyr Pro Phe Gly Ser
                245                 250                 255

Pro Leu Thr Asp Ser Val Val Val Asn Phe Gln Val Leu Gln Ser Met
                260                 265                 270

Tyr Asp Glu Lys Ile Ser Ile Leu Pro Asp Glu Lys Ile Gln Arg Gln
                275                 280                 285

Asn Leu Leu Thr Ser Ile Ser Asn Tyr Ile Pro Phe Tyr Asn Thr Thr
                290                 295                 300

Gln Thr Ile Ala Gln Leu Lys Pro Phe Val Asp Ala Gly Asn Ala Ile
305                 310                 315                 320

Ser Gly Thr Thr Thr Thr Thr Trp Gly Ser Leu Leu Asn Thr Thr Lys
                325                 330                 335

Phe Thr Thr Thr Thr Thr Thr Thr Tyr Thr Tyr Pro Gly Thr Thr Asn
                340                 345                 350

Thr Thr Val Thr Phe Ile Thr Ala Asn Asp Ser Trp Tyr Arg Gly Thr
                355                 360                 365

Val Tyr Asn Gln Asn Ile Lys Asp Val Ala Lys Lys Ala Ala Glu Leu
370                 375                 380

Tyr Ser Lys Ala Thr Lys Ala Val Leu Gly Asn Thr Phe Thr Thr Glu
385                 390                 395                 400

Asp Tyr Thr Leu Gly Tyr His Gly Gly Leu Tyr Ser Ser Ile Trp Leu
                405                 410                 415

Ser Pro Gly Arg Ser Tyr Phe Glu Thr Pro Gly Ala Tyr Thr Asp Ile
                420                 425                 430

Lys Tyr Asn Pro Phe Thr Asp Arg Gly Glu Gly Asn Met Leu Trp Ile
                435                 440                 445

Asp Trp Leu Ser Lys Lys Asn Met Asn Tyr Asp Lys Val Gln Ser Lys
                450                 455                 460

Cys Leu Ile Ser Asp Leu Pro Leu Trp Ala Ala Ala Tyr Gly Tyr Val
465                 470                 475                 480
```

```
Glu Phe Cys Ala Lys Ser Thr Gly Asp Gln Asn Ile His Met Asn Ala
                485                 490                 495

Arg Leu Leu Ile Arg Ser Pro Phe Thr Asp Pro Gln Leu Leu Val His
            500                 505                 510

Thr Asp Pro Thr Lys Gly Phe Val Pro Tyr Ser Leu Asn Phe Gly Asn
        515                 520                 525

Gly Lys Met Pro Gly Gly Ser Ser Asn Val Pro Ile Arg Met Arg Ala
    530                 535                 540

Lys Trp Tyr Pro Thr Leu Leu His Gln Gln Glu Val Leu Glu Ala Leu
545                 550                 555                 560

Ala Gln Ser Gly Pro Phe Ala Tyr His Ala Asp Ile Lys Lys Val Ser
                565                 570                 575

Leu Gly Met Lys Tyr Arg Phe Lys Trp Ile Trp Gly Gly Asn Pro Val
            580                 585                 590

Arg Gln Gln Val Val Arg Asn Pro Cys Lys Glu Thr His Ser Ser Gly
        595                 600                 605

Asn Arg Val Pro Arg Ser Leu Gln Ile Val Asp Pro Lys Tyr Asn Ser
    610                 615                 620

Pro Glu Leu Thr Phe His Thr Trp Asp Phe Lys Arg Gly Leu Phe Gly
625                 630                 635                 640

Pro Lys Ala Ile Gln Arg Met Gln Gln Gln Pro Thr Thr Thr Asp Ile
                645                 650                 655

Phe Ser Ala Gly Arg Lys Arg Pro Arg Arg Asp Thr Glu Val Tyr His
            660                 665                 670

Ser Ser Gln Glu Gly Glu Gln Lys Glu Ser Leu Leu Phe Pro Pro Val
        675                 680                 685

Lys Leu Leu Arg Arg Val Pro Pro Trp Glu Asp Ser Gln Gln Glu Glu
    690                 695                 700

Ser Gly Ser Gln Ser Ser Glu Glu Thr Gln Thr Val Ser Gln Gln
705                 710                 715                 720

Leu Lys Gln Gln Leu Gln Gln Arg Ile Leu Gly Val Lys Leu Arg
                725                 730                 735

Leu Leu Phe Asn Gln Val Gln Lys Ile Gln Gln Asn Gln Asp Ile Asn
            740                 745                 750

Pro Thr Leu Leu Pro Arg Gly Gly Asp Leu Ala Ser Leu Phe Gln Ile
        755                 760                 765

Ala Pro
    770

<210> SEQ ID NO 32
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: RD037 primer

<400> SEQUENCE: 32
gcagcagcat atggatatgt                                                    20

<210> SEQ ID NO 33
<211> LENGTH: 20
<212> TYPE: DNA
<213> ORGANISM: Homo sapien
<220> FEATURE:
<221> NAME/KEY: primer_bind
<222> LOCATION: (0)...(0)
```

<223> OTHER INFORMATION: RD038 primer

<400> SEQUENCE: 33
tgactgtgct aaagcctcta                                        20

<210> SEQ ID NO 34
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: RD051 primer

<400> SEQUENCE: 34
catacacatg aatgccaggc                                        20

<210> SEQ ID NO 35
<211> LENGTH: 20
<212> TYPE: DNA
<213> ORGANISM: Homo sapien
<220> FEATURE:
<221> NAME/KEY: primer_bind
<222> LOCATION: (0)...(0)
<223> OTHER INFORMATION: RD052 primer

<400> SEQUENCE: 35
gtacttcttg ctggtgaaat                                        20

<210> SEQ ID NO 36
<211> LENGTH: 30
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv0.5 primer

<400> SEQUENCE: 36
ctctttaaac tttggaaatg gtaaaatgcc                             30

<210> SEQ ID NO 37
<211> LENGTH: 28
<212> TYPE: DNA
<213> ORGANISM: Homo sapien
<220> FEATURE:
<221> NAME/KEY: primer_bind
<222> LOCATION: (0)...(0)
<223> OTHER INFORMATION: ufttv1 primer

<400> SEQUENCE: 37
gtctggcatt catgtgtatg ttttggtc                               28

<210> SEQ ID NO 38
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv2-2 primer

<400> SEQUENCE: 38
tggaaatggt aaaatgccag gaggtag                                27

<210> SEQ ID NO 39
<211> LENGTH: 27

```
<212> TYPE: DNA
<213> ORGANISM: Homo sapien
<220> FEATURE:
<221> NAME/KEY: primer_bind
<222> LOCATION: (0)...(0)
<223> OTHER INFORMATION: ufttv2-2 primer

<400> SEQUENCE: 39
agccttttgt ggggtctgtg tgtacta                                27

<210> SEQ ID NO 40
<211> LENGTH: 28
<212> TYPE: DNA
<213> ORGANISM: Homo sapien
<220> FEATURE:
<221> NAME/KEY: primer_bind
<222> LOCATION: (0)...(0)
<223> OTHER INFORMATION: ufttv1b primer

<400> SEQUENCE: 40
gtctggcatt catgtgtatg tttgtgtc                               28

<210> SEQ ID NO 41
<211> LENGTH: 30
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv2b primer

<400> SEQUENCE: 41
cagttttaac tttggaaatg gaaagatgcc                             30

<210> SEQ ID NO 42
<211> LENGTH: 28
<212> TYPE: DNA
<213> ORGANISM: Homo sapien
<220> FEATURE:
<221> NAME/KEY: primer_bind
<222> LOCATION: (0)...(0)
<223> OTHER INFORMATION: ufttv2a primer

<400> SEQUENCE: 42
atctacagtt gtgttctatg tttgtgtc                               28

<210> SEQ ID NO 43
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv2b-2 primer

<400> SEQUENCE: 43
tggaaatgga aagatgccag gcggcag                                27

<210> SEQ ID NO 44
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: ufttv2b-2 primer

<400> SEQUENCE: 44
```
atcccctgag ggggttgttg tgatcta                    27

<210> SEQ ID NO 45
<211> LENGTH: 30
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv2c primer

<400> SEQUENCE: 45
tagcctcaac tttggaaatg gtaaaatgcc                 30

<210> SEQ ID NO 46
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv2c-2 primer

<400> SEQUENCE: 46
tggaaatggt aaaatgccag gcggtag                    27

<210> SEQ ID NO 47
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: ufttv2c-2 primer

<400> SEQUENCE: 47
atcctctgag gggattgttg tggtcta                    27

<210> SEQ ID NO 48
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: uftype3-a1 primer

<400> SEQUENCE: 48
tactactctg gcgttcatgt ctatg                      25

<210> SEQ ID NO 49
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: uftype3-a2 primer

<400> SEQUENCE: 49
cagtattctg cgtacccgta tactg                      25

<210> SEQ ID NO 50
<211> LENGTH: 27
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv1-3con primer

<400> SEQUENCE: 50
caggagactc taacatagac atgaacg                                27

<210> SEQ ID NO 51
<211> LENGTH: 26
<212> TYPE: DNA
<213> ORGANISM: Homo sapien
<220> FEATURE:
<221> NAME/KEY: primer_bind
<222> LOCATION: (0)...(0)
<223> OTHER INFORMATION: dfttv2-3con primer

<400> SEQUENCE: 51
taacatagac atgaacgcca gagtag                                 26

<210> SEQ ID NO 52
<211> LENGTH: 3852
<212> TYPE: DNA
<213> ORGANISM: Homo sapien

<400> SEQUENCE: 52

```
attttgctac gtcactaacc gcgtgacacc cacaggccaa ccgaatgcta tgtcatccat      60
ttcctgggcc gggtttacgt cctcatataa gtaagcgcac ttccgaatgg ctgagttttc     120
cacgcccgtc cgcagcggtg aagccacgga gggagatctc cgcgtcccga gggcgggtgc     180
cgaaggtgag tttacacacc gaagtcaagg ggcaattcgg gctcgggact ggccgggcta     240
tgggcaaggc tctgaaaaaa gcatgtttat tggcaggcat tacagaaaga aaagggcgct     300
gtcactgtat gctgtgcgaa caacaaagaa ggcttgcaaa ctactaatag taatgtggac     360
cccacctcgc aatgatcaac agtaccttaa ctggcaatgg tactcaagtg tacttagctc     420
ccacgctgct atgtgcgggt gtcccgacgc tgctgctcat tttaatcatc ttgcttctgt     480
gcttcgtgcc ccgcaaaacc cacccctcc cggtccccag cgaaacctgc ccctccgacg     540
gctgccggct ctcccggctg cgccagaggc gcccggagat agagcaccat ggcctatggc     600
tggtggcgcc gaaggagaag acggtggcgc aggtggagac gcagaccatg gaggcgccgc     660
tggaggaccc gaagacgcag acctgctaga cgccgtggcc accgcagaaa cgtaaggaga     720
cgccgcagag gagggaggtg gaggaggaga tataggagat ggaaagaaa gggcaggcgc     780
agaaaaaaag ctaaaataat aataagacaa tggcaaccaa actacagaag gagatgtaac     840
atagtaggct acatccctgt actaatatgt ggcgaaaata ctgtcagcag aaactatgcc     900
acacactcag acgtaccaa ctacccagga cccttcgggg ggggtatgac tacagacaaa     960
tttactttaa gaattttgta tgatgagtac aaaaggttta tgaactactg gacagcatct    1020
aacgaagacc tagaccttg tagatatcta ggagtaaaca tgtaccttt cagacaccca    1080
gatgtagatt ttatcataaa aattaatacc atgcctcctt ttctagacac agaactcaca    1140
gcccctagca tacacccagg catgctagcc ctagacaaaa gagcaagatg gatacctagc    1200
ttaaaatcta gaccgggaaa aaaacactat attaaaataa gagtagggc accaaaaatg    1260
ttcactgata aatggtaccc ccaaacagat cttttgtgaca tggtgcttct aactgtctat    1320
gcaaccgcag cggatatgca atatccgttc ggctcaccac taactgactc tgtggttgtg    1380
aacttccagg ttctgcaatc catgtatgat gaacatatta gcatattacc agaccaacaa    1440
acacacagag aaaatttact tagtaacata acaaaataca ttcccttta taataccaca    1500
```

-continued

```
caaactatag cccaattaaa gccatttata gatgcaggca atgtaacaac aagcacaaca    1560
ccactaacat ggggatcatg cataaacaca accaagttta ctacagcaac cacagtaact    1620
tatacatatc caggcaccac cacaaccaca gtaactatgt taagctgtaa tgactcctgg    1680
tacagaggaa cagtatataa caataaaatt acagaagtac aataaaagc agctacatta     1740
tactcaaagg caacaaaaac cttgctagga acaccttca caactgagga ctacacacta     1800
gaatatcatg gaggactgta cagctcaata tggctatccg ctggtagatc ttactttgaa    1860
acaccggag catatacaga cataaagtac aatccattca cagacagagg agaaggcaac     1920
atgttatgga tagactgggt aagcaaaaaa acatgaact atgacaaagt acaaagtaaa     1980
tgcttaatat cagacatacc tctatgggca gcagcatatg gatatgtaga attttgtgca    2040
aaaagtacag gagaccaaaa catacacatg aatgccaggc tactaataag aagtcccttt    2100
acagacccac aactactagt acacacagac cccacaaaag gctttgttcc ttactcttta    2160
aactttggaa atggtaaaat gccaggaggt agtagtaatg tgcctattag aatgagagct    2220
aaatggtatc caacattatt tcaccagcaa gaggtactag aggccttagc acagtcaggc    2280
cccttgcat accactcaga cattaaaaaa gtatctctgg gtatgaaata ccgttttaag     2340
tggatctggg gtggaaaccc cgttcgccaa caggttgcta gaaatccctg caaagaaacc    2400
cactcctcgg tcaatagagt ccctagaagc ttacaaatcg ttgacccgaa atacaactca    2460
ccggaactca cattccatac ctgggacttc agacgtggcc tatttggccc gaaagctata    2520
cagagaatgc aacaacaacc aacaactact gacattttt cagcaggccg caagagaccc     2580
aggagggaca ccgaggtgta ccactccagc caagaaaggg agcaaaaaga agcttactt     2640
ttcccccag tcaagctcct cagacgagtc ccccgtggg aagactcgca gcaggaggaa      2700
agcgggtcac aaagctcaga ggaagagacg cagacactct cccagcagct caagcagcag    2760
ctgccgcaac agcgaatcct gggactcaaa ctcagactcc tatccaacca aatccaaaaa    2820
atccaacaaa atcaagatat caaccctacc ttgttaccaa ggggggggga tctagcatcc    2880
ttatttcaaa tagcaccata aacatgtttg gtgaccccaa accttacaac ccttccagta    2940
atgactggaa agaggagtac gaggcctgta gaatatggga cagaccccc agaggcaacc     3000
taagagatac cccttctac ccctgggccc caaggaaaa ccagtaccgt gtaaacttta      3060
aacttggatt tcaataaagc taggccgtgg gactttcact tgtcggtgtc tacttataaa    3120
agtaactaag cactccgagc gaagcgagga gtgcgaccct ggggctca acgccttcgg      3180
agccgcgcgc tacgccttcg gctgcgcgcg gcacctcaga cccccgctcg tgctgacacg    3240
ctcgcgcgtg tcagaccact tcgggctcgc ggggtcggg aaatttacta acagactcc     3300
gagttgccat tggactcagg agctatgaat cagtaacgaa agtgagtgag ccagacttc    3360
gccataaggc ctttatcttc ttgccatttg tcagtaacag gggtcgccat agacttcggc   3420
ctccatttta ccttgtaaaa actaccaaaa tggccgttcc agtgacgtca cagccgccat   3480
tttaagtagc tgacgtcaag gattgacgta aggttaaag gtcatcctcg gcggaagcta    3540
cacaaaatgg tggacaacat cttccgggtc aaaggttgtg catacgtcac aagtcacgtg    3600
gagggacac gctgtaaccc ggaagtaggc ccgtcacgt gacttaccac gtgtgtacac      3660
gtcaccgccg ccatttgttt aacaaaatg gctgacttcc ttcctctttt ttgaaaaaag    3720
gcgccaaaaa accgtcggcg gggggccgc gcgctgcgcg cgcggccccc ggggaggca     3780
ttgcctcccc cccgcgcg cacgcgcgcg ggtcccccc cctccggggg gctccgcccc      3840
ccggcccccc cc                                                       3852
```

<210> SEQ ID NO 53
<211> LENGTH: 3853
<212> TYPE: DNA
<213> ORGANISM: Homo sapien

<400> SEQUENCE: 53

```
ggcttagtgc gtcaccaccc acgtgacccg cctccgccaa ttaacaggta cttcgtacac      60
ttcctgggcg ggcttataag actaatataa gtagctgcac ttccgaatgg ctgagttttc     120
cacgcccgtc cgcagcggtg aagccacgga gggagctcag cgcgtcccga gggcgggtgc     180
cggaggtgag tttacacacc gcagtcaagg ggcaattcgg gctcgggact ggccgggctt     240
tgggcaaggc tcttaaaaaa gctatgttta ttggcaggca ctaccgaaag aaaagggcgc     300
tgctactgct atctgtgcat tctacaaaga caaagggaa acttctaata gctatgtgga      360
ctcccccacg caatgatcaa caataccta actggcaatg gtacacttct gtacttagct     420
cccactctgc tatgtgcggg tgttccgacg ctatcgctca tcttaatcat cttgctaatc     480
tgcttcgtgc cccgcaaaat ccgccccgc ctgataatcc aagaccccta cccgtgcgag      540
cactgcctgc tcccccggct gcccacgagg cagccggtga tcgagcacca tggcctatgg     600
gtggtggagg agacgccgga ggcgctggcg caggtggaga cgccgaccat ggaggcgccg     660
ctggaggacc cgcagacgca gacctgctag acgccgtggc cgccgcagaa cgtaaggag      720
acggcgcaga gggaggtgga gaaggaggta caggaggtgg aaaagaaagg gcagacgtag     780
aagaaaagca aaaataataa taagacagtg gcagccaaac tacagaagaa gatgtaatat     840
agtgggctac ctccctatac ttatctgtgg tggaaatact gtttctagaa actatgccac     900
acactcagac gatactaact atccaggacc ctttgggga ggcatgacca cagacaaatt      960
cagccttaga atactatatg atgaatacaa aagatttatg aactactgga cagcctcaaa    1020
tgaggaccta gatctctgta gatatctagg atgcactttt tacttcttta gacaccctga    1080
agtagacttt attataaaaa taaacaccat gcccccattc ttagatacaa ccataacagc    1140
acctagcata cacccaggcc tcatggccct agacaaaaga gccagatgga ttccttctct    1200
taaaaataga ccaggtaaaa aacactatat aaaaattaga gtaggggctc ctaaaatgtt    1260
cacagataaa tggtaccctc aaacagacct ctgtgacatg acactgctaa ctatctatgc    1320
aaccgcagcg gatatgcaat atccgttcgg ctcaccacta actgacactg tggttgttaa    1380
ctcccaagtt ctgcaatcca tgtatgatga acaattagc atattacctg atgaaaaaac     1440
taaagaaat agccttctta cttctataag aagctacata ccttttttata atactacaca    1500
aacaatagct caattaaaac catttgtaga tgcaggagga cacacaacag gctcaacaac    1560
aactacatgg ggacaactat aaacacaac taaatttacc actaccacaa caaccacata    1620
cacataccct ggcaccacaa atacagcagt aacatttata acagccaatg atacctggta    1680
cagggggaaca gcatataaag ataacattaa agatgtacca caaaagcag cacaattata     1740
ctttcaaaca acacaaaaac tactaggaaa cacattccat ggctcagatg aaacacttga    1800
ataccatgca ggcctataca gctctatctg gctatcacca ggtagatcct actttgaaac    1860
accaggtgca tacacagaca ttaaatataa cccttttaca gacagaggag aaggcaacat    1920
gctgtggata gactggctaa gtaaaaaaaa catgaaatat gacaaagtgc aaagtaagtg    1980
cctagtagca gacctaccac tgtgggcagc agcatatggt tatgtagaat ctgctctaa     2040
aagcacagga gacacaaaca tacacatgaa tgccagacta ctaataagaa gtccttttac    2100
```

-continued

```
agacccccag ctaatagtac acacagaccc cactaaaggc tttgtaccct attctttaaa      2160
ctttggaaat ggtaaaatgc caggaggtag cagcaatgtt cccataagaa tgagagctaa      2220
gtggtacccc actttatccc accaacaaga agttctagag gccttagcac agtcaggacc      2280
ctttgcttat cactcagaca ttaaaaaagt atctctaggc ataaaatacc gttttaagtg      2340
gatctggggt ggaaacccg ttcgccaaca ggttgttaga aatccctgca aggaaccccca     2400 ctcctcgggc aatagagtcc ctagaagcat acaaatcgtt gacccgagat acaactcacc      2460
ggaacttacc atccatgcct gggacttcag acgtggcttc tttggcccga aagctattca      2520
aagaatgcaa caacaaccaa ctgctactga attttttttca gcaggccgca agagacccag     2580
aagggacaca gaagtgtatc agtccgacca agaaaaggag caaaaagaaa gctcgctttt      2640 cccccccagtc aagctcctcc gaagagtccc cccgtgggag gactcggaac aggagcaaag    2700
cgggtcgcaa agctcagagg aagagacggc gaccctctcc cagcagctca aacagcagct     2760
gcagcagcag cgagtcttgg gagtcaaact cagactcctg ttcaaccaag tccaaaaaat     2820
ccaacaaaat caagatatca accctacctt gttaccaagg gggggggatc tagtatcctt     2880
ctttcaggct gtaccataaa tatgtttcca gaccctaaac cttactgccc ctccagcaat     2940
gactggaaag aagagtatga ggcctgtaaa tattgggata gacctcccag acacaacctt    3000
agagaccccc cctttttaccc ctgggcccct aaaaacaatc cttgcaatgt aagctttaaa    3060
cttggcttca aataaactag gccgtgggag tttcacttgt cggtgtctac ctctataagt     3120
cactaagcac tccgagcgca gcgaggagtg cgacccttcc ccctggtgca acgccctcgg    3180
cggccgcgcg ctacgccttc ggctgcgcgc ggcacctcgg accccgctc gtgctgacac      3240 gcttgcgcgt gtcagaccac ttcgggctcg cggggtcgg gaaatttgct aaacagactc      3300
cgagttgcca ttggacactg tagctatgaa tcagtaacga aagtgagtgg ggccagactt     3360
cgccataagg cctttatctt cttgccattt gtcagtattg ggggtcgcca taaactttgg     3420
gctccatttt aggccttccg gactacaaaa atcgccatat tgtgacgtc agagccgcca      3480 ttttaagtca gctctgggga ggcgtgactt ccagttcaaa ggtcatcctc accataactg     3540
gcacaaaatg gccgccaact tcttccgggt caaggtcac tgctacgtca taggtgacgt      3600
ggggggggac ctacttaaac acggaagtag gccccgacac gtcactgtca cgtgacagta    3660
cgtcacagcc gccatttgt tttacaaaat agccgacttc cttcctcttt tttaaaaaaa      3720
ggcgccaaaa aaccgtcggc ggggggggccg cgcgctgcgc gcgcggcccc cggggaggc     3780 acagcctccc ccccccgcgc gcatgcgcgc gggtccccccc ccctccgggg ggctccgccc    3840
cccggccccc ccc                                                        3853
```

<210> SEQ ID NO 54
<211> LENGTH: 3839
<212> TYPE: DNA
<213> ORGANISM: Homo sapien

<400> SEQUENCE: 54

```
gctacgtcac taacctacgt gtccgtctcc tataggccgg acaccgtcta cgtcatacac       60
ctcctgggca tggtctacgt gataatataa gtggcagcac ttccgaatgg ctgagttttc      120
cacgcccgtc cgcggagagg gagccacgga ggtgatcccc aacgtcccga gggcgggtgc      180
cggaggtgag tttacacacc ggagtcaagg ggcaattcgg gctcgggact ggccgggcta     240
tgggcaagac tctgaaaaat gcactttttct aggtgtagca gaaagaaaag gacactgtca    300
ctgctaccac tgcacccttc acagaaagct aggccatctg tgagaggtat gtggagaccc     360
```

-continued

```
cccaggcgaa atgaattcac tattcaacgt gactggttct acagttgctt tcactcccac    420
tcttctatgt gtggctgtgc tgattttatt aatcatctca atcatatcgc tgctatgctc    480
ggccgtccgg aagaccagaa ccctcctccg ccacccgggg ctctaagacc cctacctgct    540
ctcccggccg cccccgaggc gcccggtgat cgagcaccat ggcctatggg tggtggcgca    600
agcggcgaag gcgcccgtgg tggaggagga gatggcgccg ctggagacgc cgtcggagac    660
cccgcagacg ccgacctcgt cgccgctatc gacgccgcag aacagtaagg agacgcggca    720 ggggaggtg gactaagaga tatagacgat ggcgccgcaa aggcaaacgc agaggcaaaa    780
aaaaaattat tataaaacaa tggcagccca actacagacg cagatgcaac atagtgggct    840
acatgcctct acttatatgt ggggaaaata ctgttgccag aaactatgcc acccactcag    900
acgacagcta ctaccctgga ccctttgggg gggaatgac cacagacaaa tttactctaa    960
gaattctata tgatgaatac aagagattta tgaattactg acagcctca acgaggacc    1020 tagacttgtg tagataccta ggatgtactc tatatgtatt tagacaccca gaagtagact    1080
ttataattat aataaacaca tctcctccat ttctagacac agagataaca ggccccagca    1140
tacacccggg tatgatggcc ctcaacaaaa gagccagatg gatacctagc ataaaaaca    1200 gaccaggcag aaaacactat gtaaagatta agtgggagc cccccgaatg ttcacagata    1260
agtggtaccc ccagacagac ctctgtgaca tgacactcct aacgatcttt gcctctgcgg    1320
cggatatgca atatccgttc ggctcaccac taactgacac tatagttgtg tcattccaag    1380
ttctgcaatc catgttcaac gactgcctga gtgtacttcc tactaacttt acagaaacat    1440
caggcaaagg cgcacaatta catgataaaa ttattaacca tttaccctac tacaacacca    1500
cacaaacaca agcacaattt aagagattta cagaaaacca agaagcaaca aatggaaaca    1560
atgtatgggc aaactacgta aacagctgta aatttaacaa acaagaatca cctaaaagtg    1620
acaatggcat aggaggccca tactgctcat actcagacac atggtacaaa ggcacagcat    1680
acaataacaa aattacaact ataccctgaaa agcaagcaa actatactat gaggagacta    1740
aaaaattaat aggaataaca tttacaggat cctcacacag gttgcactac tgcggaggcc    1800
tgtactcctc agtatggcta tctgcaggca gatcatactt tgaaaccaag ggtccctaca    1860
cagacataac atacaaccca ttctcagaca gaggcgaagg caacatgctg tggatagact    1920
ggctaactaa agacacctca gtatatgaga aaacacagag taaatgtctt atacaagaca    1980
tgcccttatg ggccyctgtg ttcggattct ccgagtactg cagtaaagta acaggagaca    2040
caaacataga acacractcc agatgtgtta ttagaagccc ctacacagtg ccacaactgt    2100
tagatcacaa caacccctc aggggatacg tgccctacag ttttaacttt ggaaatggaa    2160
agatgccagg cggcagcagc caggtaccca ttagaatgag agcaaagtgg taccctaccc    2220
tttttcacca aaaagaagta ctagaagcca ttgcacagtc gggcccttc gcatatcact    2280 cagatattaa aaaagtgtca ctgggcttaa aatacagatt taagtgggtg tggggtggca    2340
accccgtgtc ccaacaggtt gttaggaacc cctgcaagac cacccaaggt tcctcgggca    2400
atagactccc tcgatcaata caagtcgttg acccgcggta caacacacca gaactcacca    2460
ttcacgcgtg ggacttcaga catggggtct ttggcagaaa agctattaag agaatgcaag    2520
aacaaccaat acctcatgac acttttttcag cagggtacaa acgcagccgc cgagatacag    2580
aagcactcca atccagccaa gaagagcaac aaaaagaaaa cttactttc ccagtccagc    2640 agctcaagcg agtccccccg tgggagacgt cgcaagagag ccaaagcgag gaagaaacct    2700
```

-continued

```
cgcaaaaaca ggagaccctc tcccagcaac tcagagacca gctgcacaag cagcgggtca      2760
tgggagacca actcaggtca ctcatctacc aaatgcagag ggtccaacaa aatcaacaca      2820
taaaccctat gttattgcca aagggtctgg cattaacttc tatttctcgc agtgtaacat      2880
agatatgttc ggggacccca aaccctacaa cccctcctcc aatgactgga aggaggagta      2940
cgaggcctgc aggtactggg acagaccccc cagacacaac ctgaggagca ccccccacta      3000
tccctgggcc cccaccccca aaccataccg tgtcaacttt gccctcaact acaaataaac      3060
ggtggccgtg ggagcttcac ttgtcggtgt ctacctctta aggtcactaa gcactccgag      3120
cgtcagcgag gagtgcgacc cttaaccaag gggcaactcc ctcgaagtcc ggcgctacgc      3180
gcttcgcgct cgcgccggaca tctcggaccc cccctcgacc cgaatcgctt gcgcgattcg      3240
gacctgcggc ctcggggggg tcgggggctt tactaaacag actccgaggt gccattggac      3300
actgaggggg caaacagcaa cgaaagtgag tggggccagg cttttgccata aggccttat      3360 cttcttgcca tttgtccgcg accggggggtc gctcctagac gcggaccccg tttcggggtc      3420
cttccggatt cctcggcgcc gttccagtga cgtcacgggc gccatgttaa gtggctgtcg      3480
ccgaggattg acgtcacagt tcaaaggtca tcctcgacgg taaccgcaaa catggcggac      3540
aatctcttcc gggtcaaagg tcgtgcatgc gtcataagtc acatgacagg gtccactta      3600 aacacggaag taggccccga catgtgactc gtcacgtgtg tacacgtcac gaccgccatt      3660
ttgtataaca aaatggccga cttccttcct cttttttgaa aaaggcgcg aaaaaaccgt      3720 cggcgggggg gccgcgcgct gcgcgcgcgg ccccccgggg aggcaacgcc tcccccccc      3780 gcgcgcatgc gcgcgggtcc ccccccctcc gggggggctcc gccccccggc ccccccgt      3839
```

<210> SEQ ID NO 55
<211> LENGTH: 3840
<212> TYPE: DNA
<213> ORGANISM: Homo sapien

<400> SEQUENCE: 55

```
gctacgtcac taacctacgt gtccgtctcc tataggccag acaccgtcta cgtcatacac       60
ttcctgggca tggtctacgt gataatataa gtggcagcac ttccgaatgg ctgagttttc      120
cacgcccgtc cgcggagagg gagccacgga ggggatcccg aacgtcccga gggcgggtgc      180
cgaaggtgag tttacacacc gcagtcaagg ggcaattcgg gctcgggact ggccgggcta      240
tgggcaaggc tctgaaaaat gcacttttct aggtgtagca gaaagaaaag gacactgtca      300
ctgctaccag tgcacccttc acagaaagct aggccatctg tgagaggtat gtggagaccc      360
cccaggcgaa atgaattcac tattcaacgt aactggttct acagttgctt tcactcccac      420
tcttctatgt gtggctgtac tgattttatt ggtcatttca atcacatcgc tgctatgctc      480
ggccgtccgg aagaccagaa ccctcctccg ccacccgggg ctgtgagacc cctacctgct      540
ctcccggccg ccccccgaggc gcccggtgat cgagcaccat ggcctatggg tggtggcgca      600
ggcgacgaag gcgcccgtgg tggaggagga gatggcgccg ctggagacgc cgtcggagac      660
cccgcagacg ccgacctcgt cgccgctatc gacgccgcag aacagtaagg agacgcggca      720
gggggaggtg gactaagaga tatagacgat ggcgccgcaa aggcaaacgc aaaggcaaaa      780
aaaaaattat tataaaacaa tggcagccca actacagacg cagatgcaac atagtgggct      840
acatgcctct acttatatgt ggggagaata ctgttgccag aaactatgcc acccactcag      900
acgacagcta ctaccctgga ccctttgggg ggggaatgac cgcagacaaa tttactctaa      960
gaattctata tgatgaatac aagagattta tgaattactg gacagcctca aacgaggacc     1020
```

-continued

```
tagacctgtg tagataccta ggatgtactt tatatgtatt tagacaccca gaagtagact    1080
ttataattat aattaacaca tcacctccat ttctagacac cgagataaca ggccctagca    1140
tacacccggg tatgatggcc ctcaacaaac gagtcagatg gatacctagc ataaagaaca    1200
gaccaggcaa aaaacactat gtaaagatta aagtgggagc cccccgaatg ttcacagata    1260
agtggtaccc ccagacagac ctctgtgaca tgacactcct aacgatcttt gcctctgcgg    1320
cggatatgca atatccgttc ggctcaccac taactgacac tatagttgtg tcactccaag    1380
ttctgcaatc catgttcaac gactgcctga gtgtacttcc tactaacttt gtagaaacaa    1440
caggcaaagg cacacaatta cataagaaaa ttataaatca tttaccgtac tacaacacca    1500
cacaaacaca agcacaattt aagagattta tagaaaacaa aactgcaaca aatggagaca    1560
atatatgggc aaactacatc aacaccgaaa aatttaacaa gaacagtca cctaaaaatg     1620 acaatggcat aggaggtcca tactgcacct actcagacac atggtacaaa ggcacagcat    1680
acaacgagaa aattaaaaag atacctgagg aggcaagcaa gctatactat gaagagacta    1740
aacaattaat aggaataaca tttacaggat cctcacacag gttgcactac tgcggaggcc    1800
tgtactcctc agtatggcta tctgcaggca gatcgtactt tgaaaccaag ggtccctaca    1860
cagacataac atacaaccca ttctcagaca gaggcgaagg caacatgctg tggatagact    1920
ggctaactaa agrtacctca gtatatgaca aaacacagag taaatgtctt atagaaaaca    1980
tgcccttgtg ggcgtctgtg tacggattct ccgagtactg cagtaaagta acaggagaca    2040
caaacataga tcacaactgc agatgtgtta ttagaagccc ctacacagtg ccacaactgt    2100
tagatcacaa caaccccctg aggggatacg taccgtacag ttttaacttt ggaaatggaa    2160
agatgccagg cggcagcagc caggtaccca ttagaatgag agcaaagtgg tacccctaccc   2220 tctttcacca aaaagaagta ctagaagcct tagcacagtc gggcccctttt gcatatcact    2280 cagatattaa aaaagtgtca ctgggcttaa aatacagatt taagtgggtg tggggtggca    2340
accccgtgtc ccaacaggtt gttaggaacc cctgcaagac cacccaaggt tcctcgggca    2400
gtagagtgcc tcgatcaata caagtcgttg acccgcggta caacacacca gaactcacca    2460
ttcacgcgtg ggacttcaga catggggttct ttggcaaaaa agctattaag cgaatgcagg    2520
agcaaccaat acctcatgac acttttttcag cagggttcaa gcgcagtcgc cgagatacag    2580
aagcactcca atccagccaa gaagagcacg aaaaagaaaa cttacttttc ccagtccagc    2640
agctcaagcg agtcccccccg tgggagacct cgcaagagag ccaaagcgag gaagaaaact    2700
cgcaaaaaca ggagaccctc tcccagcaac tcagagacca gctgcacaag cagcggctca    2760
tgggagagca actccgatcg ctcctctacc aaatgcagag ggtccaacaa atcaacaca     2820 taaaccctat gttattgcca aagggtctgg cattaacgtc tatttctcac aatgtaatat    2880
agatatgttt ggtgaccccca aaccctacaa gccctcctcc aatgactggg aggaggagta    2940
cgaggccgca aagcactggg acagaccccc cagacacgac ctcagaagca ccccccttcta   3000 ccctgggcc cccaccccta aaccatacaa tgtcaacttt gcccttaact acaaataaac     3060
ggtggccgtg ggagtttcac ttgtcggtgt ctacctctta aggtcactaa gcactccgag    3120
cgtaagcgag gagtgcgacc ctctaccaag ggcaactcc ctcgaagtcc ggcgctacgc     3180
gcttcgcgct gcgccggaca ctctcggacc ccctcgacc cgaatcgctt gcgcgattcg    3240
gacctgcggc ctcggggggg tcggggggctt tattaaacag actccgagat gccattggac    3300 actgagggg tgaacagcaa cgaaagtgag tggggccaga cttcgccata gggcctttat    3360
```

-continued

| | |
|---|---|
| cttcttgcca tttgtccgcg accggggtc gctcctaggc gcggacccccg tttccgggtc | 3420 |
| cttccgggtt cctcggcgcc gttccagtga cgtcacgggc gccatcttaa gtggctgtcg | 3480 |
| ccgaggattg acgtcacagt tcaaaggtca tcctcggcgg taaccgcaaa gatggcggtc | 3540 |
| aatctctttc gggtcaaagg tcgcgcatac gtcataagtc acatgtctag ggtccactt | 3600 |
| aaacacggaa gtaggccccg acatgtgact cgtcacgtgt gtgcacgtca cggccgccat | 3660 |
| tttgttttac aaaatggccg acttccttcc tcttttttaa aaaaggcgc caaaaaaccg | 3720 |
| tcggcggggg ggccgcgcgc tgcgcgcgcg gcccccgggg gaggcacagc ctccccccc | 3780 |
| cgcgcgcatg cgcgcgggtc ccccccccctc cggggggctc cgcccccccgg cccccccgt | 3840 |

<210> SEQ ID NO 56
<211> LENGTH: 3839
<212> TYPE: DNA
<213> ORGANISM: Homo sapien

<400> SEQUENCE: 56

| | |
|---|---|
| gctacgtcac taacctacgt gtccgtctcc cataggccgg acactgtcta cgtcatacac | 60 |
| ttcctgggca tggtctacgt gataatataa gtagcagcac ttccgaatgg ctgagttttc | 120 |
| tacgcccgtc cgcggagagg gagccacgga gaggatcccg aacgtcccga gggcgggtgc | 180 |
| cggaggtgag tttacacacc ggagtcaagg ggcaattcgg gctcgggact ggccgggcta | 240 |
| tgggcaaggc tctgaaaaat gcacttttct aggtgtagca gaaagaaaag gacactgtca | 300 |
| ctgctacctc tgcacccttc acagaaagct aagccatctg tgagaggtat gtggagaccc | 360 |
| cccaggcgaa atgaattcac tattcaacgt aactggttct acagttgctt ttactcccac | 420 |
| tcttctatgt gtggctgtcc tgattttatt ggtcatttca atcacatcgc tgctatgctc | 480 |
| ggccgtccgg aagaccagaa ccctcctccg ccacccgggg ctgtgagacc cctacccgct | 540 |
| ctcccggccg ccccccgaggc gcccggtgat cgagcaccat ggcctatggg tggtggcgca | 600 |
| ggcgacgaag gcgcccgtgg tggaggagga gatggcgccg ctggagacgc cgtcggagac | 660 |
| cccgcagacg ccgacctcgt cgccgctatc gacgccgcag aacagtaagg agacgcggca | 720 |
| gggggaggtg gactaagaga tatagacgat ggcgccgcaa aggcaaacgc agaggcaaaa | 780 |
| aaaaaattat tataaaacaa tggcagccca actacagacg cagatgcaac atagtgggct | 840 |
| acatgcctct acttatatgt ggggaaaata ctgttgccag aaactatgcc acccactcag | 900 |
| acgacagcta ctaccctgga cccttttgggg ggggaatgac cacagacaaa tttacttaa | 960 |
| gaatcctata tgatgaatac aagagattta tgaattactg acagcctca aacgaggacc | 1020 |
| tagacctgtg tagatacccta ggatgtactc tatatgtatt tagacaccca gaagtagact | 1080 |
| ttataattat aataaacaca tctcctccat tcctagacac agagataaca ggccctagca | 1140 |
| tacacccggg tatgatggcc ctcaacaaaa gagccagatg gatacctagc ataaaaaaca | 1200 |
| gaccaggcag aaaacactat gtgaaaatta agtaggagc ccccgaatg ttcacagata | 1260 |
| agtagtatcc ccagacagac ctctgtgaca tgacactcct aacgatcttt gccagtgcgg | 1320 |
| cggatatgca atatccgttc ggctcaccac taactgacac tatagttgtg tcattccaag | 1380 |
| ttctgcaatc catgtacaac gactgcctca gtgtacttcc tactaacttt acagaaggaa | 1440 |
| caggcaaagg cacacaatta catgataaaa ttattaatca tttaccctac tacaacacca | 1500 |
| cacaaacaca agcacaattc aagagattta tagaaaacaa atcagcaaca aatggggaca | 1560 |
| atgtatgggc aaactacata aacagcacaa aatttaacac acaagaatca cctaaaaatg | 1620 |
| acagtggcat aggaggccca tactgcacat acgcagatac atggtacaaa ggcacagcat | 1680 |

```
acaatgagaa aattaaaaac atacctaaac aagcaagcca actatactat gaagaaacta    1740
aaaaattaat tggcattaca ttcacaggat cctcacacag gttgcactac tgcggaggcc    1800
tgtactcctc agtatggcta tctgcaggca gatcatactt tgaaaccaag ggtccctaca    1860
cagacataac atacaaccca ttctcagaca gaggcgaagg aaacatgctg tggatagact    1920
ggctaactaa agatacctca gtatatgaca aaatacagag taaatgtctt atacaagaca    1980
tgcccttatg ggcctctgta tacggattct ccgagtactg cagtaaagta acaggagaca    2040
caaacataga acacaactgy agatgtgtta ttaggagccc ctacacagta ccacaactgt    2100
tagatcacaa caaccccctc aggggatacg taccctacag ttttaacttt ggaaatggaa    2160
agatgccggg cggcagcagc caggtaccca ttagaatgag agcaaagtgg taccctaccc    2220 ttttcacca aaagaagta ctagaagcct tagcacagtc gggccccttt gcatatcact    2280
cagatattaa aaagtttca ctgggcttaa aatacagatt taagtgggtg tggggtggca    2340
accccgtgtc ccaacaggtt gttaggaacc cctgcaagac cacccaaggt tcctcgggca    2400
gtagagtgcc tcgatcaata caagtcgttg acccgcgata caacacacca gaactcacga    2460
ttcacgcgtg ggacttcaga catgggttct ttggcagaaa ggctattaag cgaatgcagg    2520
aacaaccaat acctcatgac acttttttcag cagggttcaa gcgcagtcgc cgagatacag    2580
aagcactcca atgcagcgaa gaagacctcc aaaaagaaaa cttactttc ccagtccagc     2640 agctcaagcg agtccccccg tgggagacct cgcaagagag ccaaagcgag gaagaaaact    2700
cgcaaaaaca ggagaccctc tcccagcaac tcagagacca gctgcacaag cagcggctca    2760
tgggagagca actccgatcg ctcctctacc aaatgcagag ggtccaacaa atcaacaca     2820 taaaccctat gttattgcca aagggtctgg cattaacttc tatttctcac aatgtaatat    2880
agatatgttt ggtgacccca aaccctacaa cccctcctcc aatgactgga aggaggagta    2940
cgaggccgca aagtactggg acagaccccc cagacgcgac ctcaggagca ccccttttta    3000
cccctgggcc cccaccccca aaccatacaa tgtcaacttt gccctcaact acaaataaac    3060
ggtggccgtg ggagtttcac ttgtcggtgt ctacctctta aggtcactaa gcactccgag    3120
cgtaagcgag gagtgcgacc ctctaccaag gggcaactcc ctcgaagtcc ggcgctacgc    3180
gcttcgcgct gcgccggaca tctcggaccc cccctcgacc cgaatcgctt gcgcgattcg    3240
gacctgcggc ctcgggggg tcgggaactt tattaaacgg actccgaggt gccattggac      3300 actgagggg tgaacagcaa cgaaagtgag tggggccaga cttcgccata gggcctttat      3360
cttcttgcca tttgttcgcg accggggtc gctcctaggc gcggacccg tttcggggtc      3420 cttccgggtt catcagcgcc gttccagtga cgtcacgagc gccatcttaa gtggctgtcg    3480
ccgaggattg gcgtcacagt tcaaggtca tcctcggcgg taaccgcaaa gatggcggtc     3540
aatctcyttc aggtcaaagg tcgtgcatac gtcataagtc acatgacagg ggtccactta    3600
aacacggaag taggccccga catgtgactc gtcacgtgtg tacacgtcac ggccgcaatt    3660
ttgttttaca aaatgccga cttccttcct cttttttaaa aaaggcgcc aaaaaaccgt      3720 cggcgggggg gccgcgcgct gcgcgcgcgg ccccggggg aggcaaggcc tccccccccc     3780
gcgcgcatgc gcgcgggtcc ccccccctcc gggggctcc gccccccggc cccccccgt      3839
```

<210> SEQ ID NO 57
<211> LENGTH: 3839
<212> TYPE: DNA
<213> ORGANISM: Homo sapien -continued

```
<400> SEQUENCE: 57
gctacgtcac taaccgacgt gtccgtctcc tataggccgg acaccgtcta cgtcatacac      60
ttcctgggca tggtctacgt gataatataa gtggcagcac ttccaaatgg ctgagttttc     120
cacgcccgtc cgcagagagg gagccacgga ggggatcccg aacgtcccga gggcgggtgc     180
cggaggtgag tttacacacc ggagtcaagg ggcaattcgg gctcgggact ggccgggcta     240
tgggcaaggc tcttaaaaat gcactttttct aggtgcagta gaaagaaaag gacactgtca    300
ctgctaccac tgcaccattc acagaaagct aggccatctg tgagaggtat gtggagaccc     360
cccgtgcgaa atgacttcac tattcaacgt aactggttct acagttgctt ttactcccac     420
acttctatgt gcgggtgtgc tgatttttatt ggtcatttca atcacatcgc tgctatgctc    480
ggccgtccgg aagaccagaa ccctcctccg ccacccgggg ctctgagacc cctacccgct     540
cccccggccg ccgccgaggc gcccggtgat cgagcaccat ggcctatcgg tggtggtgga     600
ggcgacggag gcgcccgtgg aggaggagga gatggcgccg ctggagacgt cgccggagac     660
cccgcagacg ccgacctcgt cgccgctatc gacgccgcag aacagtaagg agacgcggca     720
gggggaggtg gactaggaga tatagacgat ggcgccgcaa gggcaaacgc agaggcaaaa     780
aaaagattat tataaaacag tggcagccca actacactcg gagatgcaac atagtgggct     840
acctacctct gctaatctgt ggagaaaata ctgttgctac aaactatgcc acccactcag     900
acgacagcta ctaccccgga cccttttgggg ggggaatgac tacagacaaa tttactctaa    960
gaatactgta tgatgagtac aagaggttta tgaactactg gaccgcctca aacgaggacc    1020
tagacctctg tagatacctg ggacttactc tatatgtgtt tagacaccca gaagtagact    1080
ttatactaac tataaatacc tcccctccat ttctagacac agaaataaca gggcctagca    1140
tacatccagg tatgatggcc ctcaacaaaa gagccaggtg gatacctagc ttaaaaaaca    1200
gaccaggcag aaagcactat gtaaagatta agtgggagc ccccgaatg ttcacagata     1260
agtggtaccc ccagacagac ctctgtgaca tgacactcct aacgatcttt gccagtgcgg    1320
cggatatgca atatccgttc ggctcaccac taactgacac tatagttgtg tcattccaag    1380
ttctgcaatc catgtacaac gactgcctga gcatacttcc tgataatttt gtagaacaca    1440
caggcaaagg cacccagcta cataaaaaaa taatacaaca tttaccctac tacaacacca    1500
cacaaacaca agcacaattt aaaagagttg tagaaaacat gtcagcaacc aatggaaaca    1560
atgtatgggc aaactacata aatactataa agttcacaga cacacaaact cctgaaaatg    1620
attcaggcat aggaggccct tacaccaatt attcagactc atggtacaaa ggcacagtat    1680
acaataataa aattaaagat atacctgaaa agcaagtaa attatactac gaccaaacca    1740
aacaactaat tggcattaca tttacaggat ccacacacag actacactac tgtggaggcc    1800
tatactcttc cgtatggcta tcagcaggta gatcctactt tgaaacgaaa ggcccataca    1860
cagacatcac ttacaacccc ttttcagaca gaggagaggg taatatgcta tggatagact    1920
ggctaactaa aaatgactca tcctactcaa aaacaagtag caagtgcctc atagaaaact    1980
taccccctgtg ggcctcagta tacggataca agagtactg cagcaaagta acaggagata    2040
caaacataga acataactgc agatgtgtta tcagaagccc ctacagtca ccacagctgt    2100
tagaccacaa caatcccctc agaggttacg tgccttatag cctcaacttt ggaaatggta    2160
aaatgccagg cggtagcagc ctagtaccca ttagaatgag agccaagtgg taccccactc    2220
tgttccacca aaaagaagta ctagaggcca tagcacaggc gggtcccttt gcataccact    2280
cagacattaa gaaagtatcc ctgggcataa agtacagatt taagtgggtg tggggtggca    2340
```

```
acccgtgtc ccaacaggtt gttagaaacc cctgcaagac cacccaaggt tcctcgggca    2400
atagagtgcc tcgatcaata caagtcgttg acccgcggta caacacgcca gagctcacca    2460
tacacgcgtg ggacttcaga catgggttct ttggcagaaa agctattaag agaatgcaag    2520
aacaaccaat acctcatgac acttttcag cagggttcag gcgcagtcgc cgagatacag    2580
aagcactcca atgcagccaa gaagagcaac aaaaagaaaa cttactttc ccagtccagc    2640 agctcaagcg agtcccccg tgggagacct cgcaagagag ccaaagcgag gaagaaaact    2700
cgcaaaaaca ggagaccctc tcccagcaac tcagagacca gctgcacaag cagcggctca    2760
tgggagagca actccgatcg ctcctctacc aaatgcagag ggttcaacaa aatcaacaca    2820
taaaccctat gttattgcca aagggtctgg cattaacttc tatttctcac aatgtaatat    2880
agatatgttt ggtgacccca aaccctacaa cccctcctcc aatgactgga aggaggagta    2940
ccaggccgca aagtactggg acagaccccc cagacgcgac ctgaggagca cccccttcta    3000
cccctgggcc ccaccccca aaccatacaa tgtcaacttt gccctcaact acaaataaac    3060
ggtggccgtg ggagtttcac ttgtcggtgt ctacctctta aggtcactaa gcactccgag    3120
cgtaagcgag gagtgcgacc ctctaccaag gggcaactcc ctcgaagtcc ggcgctacgc    3180
gcttcgcgct gcgccggaca tctcggaccc cccctcgacc cgaatcgctt gcgcgattcg    3240
gacctgcggc tcggggggg tcgggggctt tattaaacgg actccgaggt gccattggac    3300
actgaggggg tggacagcaa cgaaagtgag tggggccaga cttcgccata gggccttat    3360 cttcttgcca tttgtccgcg accggggtc gctcctaggc gcgacccccg tttcggggtc    3420
cttccgggtt cgtcggcgcc gttccagtga cgtcacgggc gccatcttaa gtggctgtcg    3480
ctgaggattg acgtcacagt tcaaaggtca tcctcggcgg taaccgcaaa gatggcggtc    3540
aatctcttcc gggtcaaagg tcgtgcatac gtcataagtc acatgacagg agtccactta    3600
aacacggaag taggccccga catgtgactc gtcacgtgtg tacacgtcac ggccgccatt    3660
ttgttttaca aaatggccga cttccttcct ctttttaaa aaaggcgcg aaaaaaccgt    3720 cggcgggggg gccgcgcgct gcgcgcgcgg ccccgggg aggccacgcc tccccccccc    3780
gcgcgcatgc gcgcgggtcc ccccccctcc gggggctcc gccccccggc cccccgt      3839
```

<210> SEQ ID NO 58
<211> LENGTH: 3537
<212> TYPE: DNA
<213> ORGANISM: Homo sapien

<400> SEQUENCE: 58

```
gctgcacttc cgaatggctg agttttccac gcccgtccgc agcggtgaag ccacggaggg     60
agctcagcgc gtcccgaggg cgggtgccga aggtgagttt acacaccgga gtcaaggggc    120
aattcgggct cgggactggc cgggctatgg gcaaggctct taaaaatgca cttttctagg    180
atatccagga agaaaaggct actgctactg cacacagtgc caactccaca gaaaactctc    240
aaacttttaa gaggtatgtg gagtcctccc actgacgatg aacgtgtccg cgagcgaaaa    300
tggtttctcg caactgtcta ttctcactct gctttctgtg gctgcaatga tcctgtcggt    360
cacctctgtc gcctggctac tctctctaac cgtccggaga acccgggacc ctccggggga    420
cgtcgtgctc cttcgatcgg ggtcctaccc gctctcccgg ctgctaccga gcagccaggt    480
gatcgagcac catggcctat gggtggtgga ggagacgccc cagaaggtgg aagagatgga    540
ggagaaggcc caggtggaga cgcccatgga ggacccgcag acgcagacct gctagacgcc    600
```

-continued

```
gtggacgccg cggaacagta aggagacgga ggcgcgggag gtggaggagg cgctatagga      660
ggtggaggag aaagggcaga cgcaggagaa aaagaaact tataataaga caatggcagc       720
caaactatac cagaaagtgc aacatagtag gctacatgcc agtaatcatg tgtggagaaa      780
acactctaat aagaaactat gccacacacg cagacgactg ctactggccg ggacccttg      840 ggggcggcat ggccacccag aaattcacac ccagaatcct gtacgatgac tacaagaggt     900
ttatgaacta ctggacctcc tcaaacgagg acctagacct ctgtagatac aggggagtca    960
ccctgtactt tttcagacac ccagatgtag actttatcat cttaataaac accacacctc    1020
cattcgtaga tacagagatc acaggaccca gcatacatcc gggcatgatg gccctgaaca    1080
agagagccag gttcatcccc agcctaaaga ctagacctgg cagaagacac atagtaaaga    1140
ttagagtggg ggcccccaaa ctgtacgagg acaagtggta cccccagtca gaactctgtg    1200
acgtgcccct gctaaccgtc tacgcgaccg cagcggatat gcaatatccg ttcggctcac    1260
cactaactga cactcctgtt gtaaccttcc aagtgttgcg cagcatgtac aacgacgccc    1320
tcagcacact tccctctaac tttgaaaacg caagcagtcc aggccaaaaa ctttacaaag    1380
aaatatctac atatttacca tactacaaca ccacagaaac aatagcacaa ctaaagagat    1440
atgtagaaaa tacagaaaaa aatggcacaa cgccaaaccc gtggcaatca aaatatgtaa    1500
acactactgc cttcaccact gcactaaatg ttacaactga aaaccatac accaccttct    1560 cagacagctg gtacaggggc acagtataca aagaaacaat cactgaagtg ccacttgccg    1620
cagcaaaact ctatcaaaac caaacaaaaa agctgctgtc tacaacattt acaggagggt    1680
ccgagtacct agaataccat ggaggcctgt acagctccat atggctatca gcaggccgat    1740
cctactttga aacaaaggga gcatacacag acatctgcta caaccctac acagacagag    1800 gagagggcaa catggtgtgg atagactggc tatcaaaaac agactccaga tatgacaaaa    1860
cccgcagcaa atgccttata gaaaagctac ccctatgggc agcagtatac gggtacccag    1920
aatactgtgc caagagcacc ggagactcaa acatagacat gaacgccaga gtagtaataa    1980
ggtgccccta caccgtcccc cagatgatag acaccagcga cgaactaagg ggcttcatag    2040
tatacagctt taactttggc aggggcaaaa tgcccggagg cagcagcgag gtacccataa    2100
gaatgagagc caagtggtac ccctgcctgt ttcaccaaaa agaagttcta gaagccttgg    2160
gacagtcggg cccctttcgcc taccactgcg accaaaaaaa agcagtgcta ggtctaaaat    2220
acagatttca ctggatatgg ggcggaagcc ccgtgtttcc acaggttgtt agaaacccct    2280
gcaaagacac acacggttcc tcgggcccta gaaagcctcg ctcaatacaa atcattgacc    2340
cgaagtacaa caccagagt ctcacaatcc acgcgtggga tttcagacgt ggcttctttg    2400
gctcaaaagc tattaaaaga atgcaacaac aaccaacaga tgctgaactt cttccaccag    2460
gccgcaagag gagcaggcga gacacagaag ccctccaaag cagccaagaa aagcaaaaag    2520
aaagcttact tttcaaacac ctccagctcc agcgacgaat accccatgg gaaagctcgc    2580 aggcctcgca gacagaggca gagagcgaaa aagagcaaga ggcagtctc tcccagcagc    2640 tccgagagca gctttaccag caaaagctcc tcggcaagca gctcagggaa atgttcctac    2700
aactccacaa atccaacaa atcaacacg tcaaccctac cttattgcca agggatcagg    2760
ctttaatctg ctggtctcag attcagtaat taacatgttt ggagaccta aaccatacaa    2820 accctccagc aacgactgga agaggagta cgaggccgct aagtattggg acaggcccc    2880 cagatctaac cttagagata acccccttcta tccctgggcc cccccaagca atccctacaa    2940
agtaaacttt aaactaggct tccaataaag ctaggccgtg ggagtttcac ttgtcggtgt    3000
```

```
ctgcttctta aggtcgccaa gcactccgag cgtaagcgag gagtgcgacc ctccccccg    3060 gtagcaactt cttcggagtc cggcgctacg ccttcggctg cgccggacac ctcagacccc    3120
ccctccaccc gaaacgcttg cgcgtttcgg accttcggcg tcgggggggt cgggagcttt    3180
attaaacaga ctccgagttg ccattggaca ctggagctgt gaatcagtaa cgaaagtgag    3240
tggggccaga cttcgccata aggcctttat cttcttgcca ttggatggtg gggagggtcg    3300
ccataggctt cagcctcggt tttaggcctt ccggactaca aaaatggcgg atttcgtgac    3360
gtcacggccg ccattttaag tcagcgctgg ggaggcatga ctgtaagttc aaaggtcatc    3420
ctcaccggaa ctgacacaaa atggccgcca atttcttccg ggtcaaaggt cacgcctacg    3480
tcatagatga cgtaggaggg cgtactctgt aaacacggaa gtaggccccg acacgtg       3537
```

<210> SEQ ID NO 59
<211> LENGTH: 3539
<212> TYPE: DNA
<213> ORGANISM: Homo sapien

<400> SEQUENCE: 59

```
gctgcacttc cgaatggctg agttttccac gcccgtccgc agcggtgaag ccacggaggg      60
agctcagcgc gtcccgaggg cgggtgccgg aggtgagttt acacaccgga gtcaaggggc     120
aattcgggct cgggactggc cgggctatgg gcaaggctct taaaaatgca cttttctagg     180
atatccagaa agaaaaggct actgctactg caaacagagc cagctccaca gaagactctc     240
aaacttttaa aaggtatgtg gagtcctccc actgacgatg aacgtgtccg cgagcgaaaa     300
tggttcctcg ccactgttta ttctcactct gctttctgtg gctgcaatga tcctgtcggc     360
cacctctgtc gcttggctac tctatctaac cgtccggaga acccgggacc ctccggggga     420
cgtcgtgctc cttcgatcgg gatcctaccg ctctcccgg ctgctaccga gcagcccggt     480
gatcgagcac catggcctat gggtggtgga ggagacgccg cagaaggtgg aagagatgga     540
ggagaaggcc caggtggaga cgcccatgga ggacccgcag acgcagacct gctagacgcc     600
gtggacgccg cagaacagta aggagacgga ggcgcgggag gtggaggagg cgctatagga     660
ggtggaggag aaagggcaga cgcgggagaa aaagaaact tataataaaa caatggcagc     720
caaactatac cagagagtgc aacatagtag gctacatgcc agtaatcatg tgtggagaga     780
acactctaat aagaaactat gccacacacg cagacgactg ctactggccg ggaccctttg     840
ggggcggcat ggccacccag aaattcacac tcagaatcct gtacgatgac tacaagaggt     900
ttatgaacta ctggacctcc tcaaacgagg acctagacct ctgtagatac aggggagtca     960
ccctgtactt tttcagaaac ccagatgtag actttatcat cctcataaac accacacctc    1020
cgttcgtaga tacagagatc acaggaccca gcatacatcc gggcatgatg gccctcaaca    1080
aaagagccag gttcatcccc agcctaaaaa ctagacctgg cagaagacac atagtaaaga    1140
ttaaagtggg ggccccaaa ctgtacgagg acaagtggta cccccagtca gaactctgtg    1200
acatgcccct actaaccgtc tacgccaccg cagcggatat gcaatatccg ttcggctcac    1260
cactaactga cactcctgtt gtaaccttcc aagtgttgcg cagcatgtac aacgacgccc    1320
ttagcatact tccctctaac tttcaaagcc cagacagtcc aggccaaaaa ctttacgaac    1380
aaatatctaa gtatttacca tactacaaca ccacagaaac aatggcacaa ctaaagagat    1440
atatagaaaa tacagaaaaa ataccacat cgccaaaccc atggcaaaca aaatatgtaa    1500
acactactgc cttcaccact ccacaaactg ttacaactca acagccatac accagcttct    1560
```

```
cagacagctg gtacaggggc acagtataca caaacgaaat cactaaggtg ccacttgccg    1620
cagcaaaagt gtatgaaact caaacaaaaa acctgctgtc tacaacattt acaggagggt    1680
cagagtacct agaataccat ggaggcctgt acagctccat atggctatca gcaggccgat    1740
cctactttga acaaagggga gcatacacag acatctgcta caaccccctac acagacagag   1800 gagagggcaa catggtgtgg atagactggc tatcaaaaac agactccaga tatgacaaaa    1860
cccgcagcaa atgccttata gaaaagctac ccctatgggc agcagtatac gggtacgcag    1920
aatactgtgc caagagcacc ggagactcaa acatagacat gaacgccaga gtagtaatta    1980 ggtgcccctca caccacccccc cagatgatag acaccagcga cgaactaagg ggcttcatag   2040
tatacagctt taactttggc aggggcaaaa tgcccggagg cagcagcgag gtacccatta    2100
gaatgagagc caagtggtac ccctgcctac ttcaccaaaa aggagttcta gaagccttag    2160
gacagtcagg ccccttcgcc taccaccgcg accaaaaaaa agcagtgcta ggtctaaaat    2220
acagatttca ctggatatgg ggcggaaacc ccgtgtttcc acaggttgtt agaaaccccct    2280 gcaaagacac acacggttcc tcgggcccta gaaagcctcg ctcaatacaa atcattgacc    2340
cgaagtacaa cacaccagag ctcacaatcc acgcgtggga tttcagacgt ggcttctttg    2400
gcccaaaagc tattaagaga atgcaacaac aaccaacaga tgctgaactt cttccaccag    2460
gccgcaagag gagcaggcga gacaccgaag ccctccaaag cagccaagaa aagcagaaag    2520
aaagcttact tttcaaacag ctccagctcc ggcgacgagt accccgtgg gaaagctcgc    2580 aggcctcgca gacagaggca gagagcgaaa agagcaaga ggacagtctc tcccagcagc    2640
tccgagagca gcttcaccag caaaagctcc tcggcaagca gctcagggaa atgttcctac    2700
aactccacaa aatccaacaa aatcaacacg tcaaccctac cctattgcca aaagatcagg    2760 cttttaatatg ctggtctcag attcagtaat taacatgttc ggagacccta accatacaa    2820 accctccagc aacgactgga aagaggagta cgaggccgct aaatattggg acaggccccc    2880
cagatttgac cttagagata agcccttcta tccctgggcc cccccaagca atccctacaa    2940
agtaaacttt aaactaggct ttcaataaag ctaggccgtg ggagtttcac ttgtcggtgt    3000
ctgcttctta aggtcgccaa gcactccgag cgtaagcgag gagtgcgacc ctcccccccg    3060
gtagcaactt cttcggagtc cggcgctacg ccttcggctg cgccggacac ctcagacccc    3120
ccctccaccc gaaacgcttg cgcgtttcgg accttcggcg tcgggggggt cgggagcttt    3180
attaaacaga ctccgagttg ccattggaca ctggagctgt gaatcagtaa cgaaagtgag    3240
tggggccaga cttcgccata aggcctttat cttcttgcca tttgtcagtg tagggggtcg    3300
ccataggctt cggcctcgtt tttaggcctt ccggactaca aaaatggcag attccgtgac    3360
gtcatggccg ccatttttaag taaggcggaa gcagctgtcc ctgtaacaaa atggcggcga    3420
cagccttccg ctttgcacaa aatggaggtg tttatcttcc gggtcaaagg tcacgcctac    3480
gtcataagtc acgtgggagg gacccgctgc gcatacacgg aagtaggccc cgacacgtg    3539
```

<210> SEQ ID NO 60
<211> LENGTH: 22
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetAforward1 primer

<400> SEQUENCE: 60
gctgcacttc cgaatggctg ag    22

<210> SEQ ID NO 61
<211> LENGTH: 22
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetAreverse1 primer

<400> SEQUENCE: 61
ccaccagcca taggccatgg tg                                             22

<210> SEQ ID NO 62
<211> LENGTH: 21
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetAforward2 primer

<400> SEQUENCE: 62
gagttttcca cgcccgtccg c                                              21

<210> SEQ ID NO 63
<211> LENGTH: 22
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetAreverse2 primer

<400> SEQUENCE: 63
ccagccatag gccatggtgc tc                                             22

<210> SEQ ID NO 64
<211> LENGTH: 24
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetBforward1 primer

<400> SEQUENCE: 64
gtgggacttt cacttgtcgg tgtc                                           24

<210> SEQ ID NO 65
<211> LENGTH: 25
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetBreverse1 primer

<400> SEQUENCE: 65
gacaaatggc aagaagataa aggcc                                          25

<210> SEQ ID NO 66
<211> LENGTH: 22
<212> TYPE: DNA
<213> ORGANISM: Homo sapien
<220> FEATURE:
<221> NAME/KEY: primer_bind
<222> LOCATION: (0)...(0)

<223> OTHER INFORMATION: SetBforward2 primer

<400> SEQUENCE: 66
aggtcactaa gcactccgag cg                                    22

<210> SEQ ID NO 67
<211> LENGTH: 21
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetBreverse2 primer

<400> SEQUENCE: 67
gcgaagtctg gccccactca c                                     21

<210> SEQ ID NO 68
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetCforward1 primer

<400> SEQUENCE: 68
cagactccga gttgccattg gac                                   23

<210> SEQ ID NO 69
<211> LENGTH: 22
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetCreverse1 primer

<400> SEQUENCE: 69
cacgtgtcgg ggcctacttc cg                                    22

<210> SEQ ID NO 70
<211> LENGTH: 23
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetCforward2 primer

<400> SEQUENCE: 70
gcaacgaaag tgagtggggc cag                                   23

<210> SEQ ID NO 71
<211> LENGTH: 21
<212> TYPE: DNA
<213> ORGANISM: Homo sapien
<220> FEATURE:
<221> NAME/KEY: primer_bind
<222> LOCATION: (0)...(0)
<223> OTHER INFORMATION: SetCreverse2 primer

<400> SEQUENCE: 71
ggtttccgcc gaggatgacc t                                     21

METHODS OF UTILIZING THE TT VIRUS

BACKGROUND OF THE INVENTION

1. Field of the Invention

The present invention relates generally to the TT virus and to methods of use thereof. More particularly, the present invention relates to nucleic acid primers useful for detection of the TT virus, use of the TT virus as a vector, use of the TT virus for human and veterinary diagnostics, and use of the TT virus for testing prior to transplantation or xenotransplantation. Additionally, the present invention includes use of TT virus sequence diversity as a means of monitoring viral transmission between individuals.

2. Background of the Invention

Recently, a novel human DNA virus was isolated from the serum of a Japanese patient (initials T.T.) with cryptogenic hepatitis (Nishizawa et al., Biochem Biophys Res Commun 241:92–97 (1997)). Utilizing PCR, TT virus (TTV) was detected in sera from three of five patients with non-A to GBV-C hepatitis. Subsequently, the nearly complete nucleotide sequence of the TTV genome, encompassing 3739 bases, and a more sensitive PCR assay for the detection of virus in serum were reported (Okamoto et al., Hepatol. Res. 10:1–16 (1998)). In addition, based upon sensitivity to single-strand but not double-strand-specific endonucleases, the virus appeared to possess a single-stranded DNA genome. Data presented regarding the size of the genome, its single-strandedness, and resistance to detergents, suggested that TTV was similar to the parvoviruses (Okamoto et al., Hepatol. Res. 10:1–16 (1998)). However, the buoyant density in CsCl (1.31–1.32 g/ml) was lower than that reported for the parvoviruses.

Several PCR studies have been performed to assess the prevalence of this virus in various populations. One assay described by Okamoto et al. (Okamoto et al., Hepatol. Res. 10:1–16 (1998)) detected TTV DNA in hemophiliacs (68%), intravenous drug abusers (40%), patients on maintenance hemodialysis (46%) and those with cryptogenic hepatitis and/or chronic liver disease (46–48%). Further, TTV infection in Japanese normal blood donors was found to be 12%. The rates of TTV infection in the United Kingdom have recently been reported at 1.9% (19 of 1000 blood donors) (Simmonds et al., The Lancet 352:191–194 (1998)) using two distinct primers sets and 10% (3 of 30 healthy controls) (Naoumov et al., The Lancet 352:195–197 (1998)) using the PCR strategy of Okamoto (Okamoto et al., Hepatol. Res. 10:1–16 (1998)). Both of these reports identified TTV DNA in patients at risk for acquiring parenterally transmitted viruses (27–39%) and/or in patients with hepatitis (19–22%). These studies suggest that TTV can be transmitted via blood or blood products and may also be associated with some cases of cryptogenic hepatitis.

The preliminary epidemiological studies of TTV described above utilized several different first generation PCR primer pairs. Desai et al. (Desai et al., J. Infect. Dis. in press:(1999)) compared the sensitivities of two first generation TTV PCR primers sets and demonstrated that the majority of TTV-positive samples were detected by only one of the two primer sets. Thus, previous reports that utilized a single PCR primer pair may have significantly underestimated the true prevalence of the virus. Second generation PCR assays for TTV appear to confirm the underestimation of TTV prevalence. Specifically, a PCR assay described by Takahashi et al (Takahashi et al., Hepatol. Res. 12:233–239 (1998)) that was 10 to 100 times more sensitive than the assay described by Okamoto et al (Okamoto et al., Hepatol. Res. 10:1–16 (1998)) found TTV present in 92 of 100 healthy individuals who visited a Japanese hospital for routine health screening. Therefore, TTV prevalence in the normal Japanese population appears to be much higher than the 12% originally reported.

The high rate of TTV carriers in the normal population may not be compatible with an exclusive parenteral transmission route. A possible fecal-oral transmission route was suggested by a study that demonstrated the presence of TTV in the feces of infected humans (Okamoto et al., J. of Med. Virol. 56:128–132 (1998)). Additional non-parenteral routes of infection may explain the high prevalence of TTV infection in healthy individuals. Finally, based upon limited prevalence studies and the high rates of TTV in the normal populations (Charlton et al., Hepatology 28:839–842 (1998; Naoumov et al., The Lancet 352:195–197 (1998; Simmonds et al., The Lancet 352:191–194 (1998)), the association between TTV infection and human hepatitis is questionable.

The detection of TTV in test samples can be enhanced by the use of DNA amplification assays that utilize DNA oligomers as primers, since the amount of DNA target nucleotides present in a test sample may be in minute amounts. Methods for amplifying and detecting a target nucleic acid sequence that may be present in a test sample are well-known in the art. Such methods include the polymerase chain reaction (PCR) described in U.S. Pat. Nos. 4,683,195 and 4,683,202, the ligase chain reaction (LCR) described in European Patent Application EP-A-320 308, gap LCR (GLCR) described in European Patent Application EP-A-439 182 and U.S. Pat. No. 5,427,930 which is incorporated herein by reference, multiplex LCR described in International Patent Application No. WO 93/20227, and the like. These methods have found widespread application in the medical diagnostic field as well as in the fields of genetics, molecular biology and biochemistry.

It would be advantageous to provide DNA oligomer primers derived from TTV and diagnostics, and test kits which utilize these primers. Such primers could greatly enhance the ability to more accurately detect TTV infections, and track the virus' route of transmission.

In addition to the advantages of viral detection, viruses have the potential to serve as vectors for purposes such as expression of cloned genes in culture and development of treatments for disease through gene therapy. Viruses that have been developed into vectors include those with DNA genomes such as adeno-associated virus (see, e.g., Muzyczka, N., Current Topics in Microbiol. and Immunol. 158:97–129 (1992) and Kotin, R. M., Human Gene Therapy 5:793–801 (1994)), adenovirus (see, e.g., Haj-Ahmad et al., J. Virol. 57:264–274 (1986) and Berkner, K. L., BioTechniques 6:619–629 (1988)), herpes virus (see, e.g., Breakefield et al., New Biol. 3:203–218 (1991) and Wolfe et al., Nature Genetics 1:379–384 (1992)) and papovavirus (see, e.g., Grossi et al., Arch. Virol. 102:275–283 (1988) and Milanesi et al., Mol Cell. Biol. 4:1551–1560 (1984)), and those with RNA genomes such as modified retroviruses (see, e.g., Gazit et al., Journal of Virology 60:19–28 (1986) and Palmer et al., Proc. Natl. Acad. Sci. USA 84:1055–1059 (1987)).

DNA viruses with small genomes, such as TTV, typically encode relatively few proteins and rely on the host cell to provide most replication and expression functions, thereby reducing the complexity of their interaction with the host cell. Furthermore, TTV infection does not appear to be associated with any disease, as is evidenced by its presence in nearly 100% of some human, normal populations. Its high prevalence also suggests that infection occurs readily, and that re-infection is common, as is implied by co-infections with multiple strains. All these traits are desirable in a gene therapy vector, which should be uncomplicated, non-pathogenic, easily delivered and have the potential for multiple treatments, or for being maintained over extended periods of time.

Comparison of numerous TTV genomes has demonstrated a high sequence diversity and an apparent lack of geographic localization. This implies either a high mutation rate, due to a low fidelity replicase, or an ancient virus family that has undergone extensive evolutionary drift. Researchers of HIV have used its sequence diversity as a basis for epidemiological studies and to demonstrate specific transmission of a viral infection from one individual to another. Likewise, the diversity of TTV may help establish the primary route of infection, and benefit investigations, such as forensics, that attempt to demonstrate contact between individuals.

All U.S. patents and publications are herein incorporated in their entirety by reference.

SUMMARY OF THE INVENTION

The present invention includes primers of probes specific for TT virus (TTV). These primers or probes are represented by SEQ ID NO:29, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70 and SEQ ID NO:71. Of particular interest within the above grouping are SEQ ID NOS:60–71.

Additionally, the present invention encompasses a method for detecting the presence of TTV target nucleotides which may be present in a test sample. This method comprises the steps of:(a) contacting a test sample suspected of containing a target TTV nucleotide sequence with a TTV primer pair consisting of: 1) SEQ ID NO:60 and 2) a primer selected from the group consisting of SEQ ID NO:61, SEQ ID NO:63, SEQ ID NO:65, SEQ ID NO:67, SEQ ID NO:69 and SEQ ID NO:71, to form a reaction mixture which generates a product; (b) contacting the reaction mixture with a TTV primer pair consisting of: 1) SEQ ID NO:62 and 2) a primer selected from the group consisting of SEQ ID NO:61, SEQ ID NO:63, SEQ ID NO:65, SEQ ID NO:67, SEQ ID NO:69 and SEQ ID NO:71, wherein the nucleotide sequence of the selected primer hybridizes with the product of the reaction mixture of (a); and (c) detecting the presence of the TTV target nucleotide in the test sample. The primer pair of step (a) consists of, for example SEQ ID NO:60 and SEQ ID NO:61, and the primer pair of step (b) consists of for example, SEQ ID NO:62 and SEQ ID NO:63.

Furthermore, the present invention also includes a method for detecting the presence of TTV target nucleotides which may be present in a test sample comprising the steps of: (a) contacting a test sample suspected of containing a target TTV nucleotide sequence with a TTV primer pair consisting of: 1) SEQ ID NO:64 and 2) a primer selected from the group consisting of SEQ ID NO:61, SEQ ID NO:63, SEQ ID NO:65, SEQ ID NO:67, SEQ ID NO:69 and SEQ ID NO:71, to form a reaction mixture which generates a product; (b) contacting the reaction mixture with a TTV primer pair consisting of: 1) SEQ ID NO:66 and 2) a primer selected from the group consisting of SEQ ID SEQ ID NO:61, SEQ ID NO:63, SEQ ID NO:65, SEQ ID NO:67, SEQ ID NO:69 and SEQ ID NO:71, wherein the nucleotide sequence of the selected primer hybridizes with the product of the reaction mixture of (a); and (c) detecting the presence of the TTV target nucleotide in the test sample. The primer pair of step (a) consists of, for example SEQ ID NO:64 and SEQ ID NO:65, and the primer pair of step (b) consists of, for example, SEQ ID NO:66 and SEQ ID NO: 67.

Moreover, the present invention also encompasses a method for detecting the presence of TTV target nucleotides which may be present in a test sample. This method comprises the steps of: (a) contacting a test sample suspected of containing a target TTV nucleotide sequence with a TTV primer pair consisting of: 1) SEQ ID NO:68 and 2) a primer selected from the group consisting of SEQ ID NO:61, SEQ ID NO:63, SEQ ID NO:65, SEQ ID NO;67, SEQ ID NO:69 and SEQ ID NO:71, to form a reaction mixture which generates a product; (b) contacting the reaction mixture with a TTV primer pair consisting of: 1) SEQ ID NO:70 and 2) a primer selected from the group consisting of SEQ ID NO:61, SEQ ID NO:63, SEQ ID NO:65, SEQ ID NO:67, SEQ ID NO:69 and SEQ ID NO:71, wherein the nucleotide sequence of the selected primer hybridizes with the product of the reaction mixture; and (c) detecting the presence of the target TTV nucleotide in the test sample. The primer pair of step (a) consists of, for example, SEQ ID NO:68 and SEQ ID NO:69, and the primer pair of step (b) consists of, for example, SEQ ID NO:70 and SEQ ID NO:71. In any of the above methods, the test sample may be isolated from a human or an animal; thus, the methods may be used for both human and veterinary diagnostic purposes.

Additionally, the present invention includes a test kit for detecting target TTV nucleotides in a test sample, comprising: (a) a container containing a primer pair specific for a TTV target nucleotide, wherein said primer pair consists of 1) SEQ ID NO:60 and 2) a primer selected from the group consisting of SEQ ID NO:61, SEQ ID NO:63, SEQ ID NO:65, SEQ ID NO:67, SEQ ID NO:69 and SEQ ID NO:71; and (b) a container containing a primer pair specific for TTV, wherein said primer pair consists of 1) SEQ ID NO:62 and 2) a primer selected from the group consisting of is SEQ ID NO:61, SEQ ID NO:63, SEQ ID NO:65, SEQ ID NO:67, SEQ ID NO;69 and SEQ ID NO:71. The primer pair of (a) consists of, for example, SEQ ID NO:60 and SEQ ID NO:61, and said primer pair of (b) consists of SEQ ID NO:62 and SEQ ID NO:63.

The present invention also encompasses a test kit for detecting target TTV nucleotides in a test sample, comprising: (a) a container containing a primer pair specific for a TTV target nucleotide, wherein the primer pair consists of 1)SEQ ID NO:64 and 2) a primer selected from the group consisting of SEQ ID NO:61, SEQ ID NO:63, SEQ ID NO:65. SEQ ID NO:67, SEQ ID NO:69 and SEQ ID NO:71; (b) a container containing a primer pair specific for TTV, wherein the primer pair consists of 1) SEQ ID NO:66 and 2) a primer selected from the group consisting of SEQ ID NO:61, SEQ ID NO:63, SEQ ID NO:65, SEQ ID NO:67, SEQ ID NO:69 and SEQ ID NO:71. The primer pair of (a) consists of, for example, SEQ ID NO:64 and SEQ ID NO:65, and the primer pair of (b) consists of, for example, SEQ ID NO:66 and SEQ ID NO:67.

Additionally, the present invention includes a test kit for detecting target TTV nucleotides in a test sample, comprising: (a) a container containing a primer pair specific for a TTV target nucleotide, wherein the primer pair consists of: 1) SEQ ID NO:68 and 2) a primer selected from the group consisting of SEQ ID NO:61, SEQ ID NO:63, SEQ ID NO:65, SEQ ID NO:67, SEQ ID NO:69 and SEQ ID NO:71;

(b) a container containing a primer pair specific for TTV, wherein the primer pair consists of: 1) SEQ ID NO:70 and 2) a primer selected from the group consisting of SEQ ID NO:61, SEQ ID NO:63, SEQ ID NO:65, SEQ ID NO:67, SEQ ID NO:69 and SEQ ID NO:71. The primer pair of (a) consists of, for example, SEQ ID NO:68 and SEQ ID NO:69, and the pair of (b) consists of, for example, SEQ ID NO:70 and SEQ ID NO:71. Any of the test samples may be isolated from a human or an animal.

Furthermore, the present invention also encompasses a TTV-based vector comprising: 1) a promoter; 2) a heterologous DNA sequence; and 3) a nucleotide sequence encoding TTV, a fragment of the nucleotide sequence or a complement of the nucleotide sequence or the fragment, wherein the heterologous DNA sequence is operably linked to the promoter. The promoter may be derived from TTV or from a heterologous source. The heterologous DNA sequence may encode a polynucleotide sequence that is complementary to a targeted RNA sequence. For example, the heterologous DNA sequence may encodes protein. The vector may be capable of being packaged into TTV particles for stable maintenance or expression of said heterologous DNA sequence.

The invention also includes a host cell comprising the above vector. The host cell may be eukaryotic.

Additionally, the invention includes a method of expressing the heterologous DNA sequence or a product encoded by the heterologous DNA sequence, in a host, comprising introducing the vector into a host for a time and under conditions sufficient for expression of the heterologous DNA sequence or product encoded thereby.

The invention also includes a method of detecting transmission of TTV from one individual to another comprising the steps of: (a) obtaining a biological sample from an individual having TTV; (b) isolating a TTV DNA sequence from the biological sample; (c) obtaining a biological sample from a second individual having TTV; (d) isolating a TTV DNA sequence from the biological sample of the second individual; (e) comparing the TTV DNA sequence of the first individual with the TTV DNA sequence of the second individual, identity between the DNA sequence of the first individual and the DNA sequence of the second individual indicating transmission of TTV from one individual to the other.

The invention also includes a method of determining TTV-infection in a tissue or organ prior to transplantation or xenotransplantation of the tissue or organ comprising the steps of:

(a) contacting a biological sample suspecting of containing a TTV target nucleotide sequence, from a potential donor animal, with a TTV primer pair represented by SEQ ID NO:60 and SEQ ID NO:61 to form a first reaction mixture;
(b) contacting said reaction mixture with a TTV primer pair represented by SEQ ID NO:62 and SEQ ID NO:63 in order to form a second reaction mixture; and (c) detecting the presence of the TTV target nucleotide in the test sample, presence of the nucleotide indicating TTV-infection in the biological sample and in the tissue or organ. The invention also includes a method of determining TTV-infection in a tissue or organ prior to transplantation or xenotransplantation of the tissue or organ comprising the steps of: (a) contacting a biological sample suspecting of containing a TTV target nucleotide sequence, from a potential donor animal, with a TTV primer pair represented by SEQ ID NO:64 and SEQ ID NO:65, to form a first reaction mixture; (b) contacting the reaction mixture with a TTV primer pair represented by SEQ ID NO:66 and SEQ ID NO:67; and c) detecting the presence of the TTV target nucleotide in the test sample, presence of the nucleotide indicating TTV-infection in the biological sample and in the tissue or organ.

Additionally, a method of determining TTV-infection in a tissue or organ prior to transplantation or xenotransplantation of said tissue or organ comprising the steps of:

(a) contacting a biological sample suspecting of containing a TTV target nucleotide sequence, from a potential donor animal, with a TTV primer pair represented by SEQ ID NO:68 and SEQ ID NO:69, to form a first reaction mixture;
(b) contacting said reaction mixture with a TTV primer pair represented by SEQ ID NO:70 and SEQ ID NO:71; and
(c) detecting the presence of the TTV target nucleotide in said test sample, presence of said nucleotide indicating TTV-infection in said biological sample and in said tissue or organ. In the above-mentioned methods, the biological sample may be selected from the group consisting of blood, tissue and an organ.

Additionally, the invention includes a method of detecting the presence of target TTV nucleotides in a test sample, comprising the steps of:

(a) contacting a test sample suspecting of containing a target TTV nucleotide with a primer pair represented by SEQ ID NO:60 and SEQ ID NO:61, to form a reaction mixture; (b) contacting said reaction mixture with at least one TTV probe selected from the group consisting of SEQ ID NO:62 and SEQ ID NO:63; and (c) detecting the presence of said target TTV nucleotide in said test sample. In yet another embodiment of the method, the test sample may be contacted with a primer pair represented by SEQ ID NO:64 and SEQ ID NO:65 and the resulting reaction mixture contacted with at least one TTV probe selected from the group consisting of SEQ ID NO:66 and SEQ ID NO:67. In yet another embodiment, the test sample may be contacted with primer pair SEQ ID NO:68 and SEQ ID NO:69 and the resulting reaction mixture contacted with at least one TTV probe selected from the group consisting of SEQ ID NO:70 and SEQ ID NO:71. In the above-mentioned embodiments, at least one TTV probe may be conjugated to a detectable signal-generating compound. Such a compound is selected from the group consisting of a chemiluminescent compound, fluorescein and an enzyme. In the alternative, the TTV probe may be conjugated to an antibody.

The invention also includes a method of detecting TTV target nucleotides which may be present in a test sample comprising contacting the test sample suspected of containing a target TTV nucleotide sequence with a TTV primer pair consisting of 1) a primer selected from the group consisting of: SEQ ID NO:60, SEQ ID NO:62, SEQ ID NO:64, SEQ ID NO:66, SEQ ID NO:68, and SEQ ID NO:70, and 2) a primer selected from the group consisting: SEQ ID NO:61, SEQ ID NO:63, SEQ ID NO:65, SEQ ID NO:67, SEQ ID NO:69, and SEQ ID NO:71, to form a reaction mixture which generates a product. In another embodiment, the method further comprises the steps of a) contacting the reaction mixture with a TTV primer pair consisting of: 1) a primer selected from the group consisting of: SEQ ID NO:60, SEQ ID NO:62, SEQ ID NO:64, SEQ ID NO:66, SEQ ID NO:68, and SEQ ID NO:70, wherein the nucleotide sequence of the selected primer hybridizes with the product of the reaction mixture and 2) a primer selected from the group consisting: SEQ ID NO:61, SEQ ID NO:63, SEQ ID NO:65, SEQ ID NO:67, SEQ ID NO:69, and SEQ ID NO:71, wherein the nucleotide sequence of the selected primer hybridizes with the product of the reaction mixture, and b) detecting the presence of the TTV target nucleotide in the test sample.

The present invention provides novel TT virus (TTV) DNA oligomer primers and probes. These DNA primers and probes are identified as SEQUENCE ID NOS. 60–71.

The present invention also provides an assay for detecting the presence of TTV in a test sample, which comprises (a) contacting a test sample suspected of containing a target TTV DNA sequence with a pair of TTV primers selected from the group consisting of the pair of SEQUENCE ID NOS. 60 and 61, followed by the pair of SEQUENCE ID NOS. 62 and 63; or the pair of SEQUENCE ID NOS. 64 and 65, followed by the pair of SEQUENCE ID NOS. 66 and 67; or the pair of SEQUENCE ID NOS. 68 and 69, followed by the pair of SEQUENCE ID NOS. 70 and 71, and (b) detecting the presence of the target DNA in the test sample. The TTV primers can be conjugated to a signal generating compound. This signal generating compound is selected from the group consisting of a chemiluminescent compound, a fluorescein compound and an enzyme. The reaction can be performed on a solid phase. Each primer can be attached to a different hapten such as adamantane and carbazole.

Also provided is a test kit for detecting target TTV DNA in a test sample, comprising (a) a container containing a TTV primer, wherein the primer is selected from the group consisting of the pair of SEQUENCE ID NOS. 60 and 61, followed by the pair of SEQUENCE ID NOS. 62 and 63; or the pair of SEQUENCE ID NOS. 64 and 65, followed by the pair of SEQUENCE ID NOS. 66 and 67; or the pair of SEQUENCE ID NOS. 68 and 69, followed by the pair of SEQUENCE ID NOS. 70 and 71, and (b) a container containing a detection reagents. The TTV primers can be conjugated to a detectable signal generating compound. This signal generating compound is selected from the group consisting of a chemiluminescent compound, a fluorescein compound and an enzyme. The reaction can be performed on a solid phase. Each primer primer can be attached to a different hapten such as adamantane and carbazole.

Also provided is the proposed use of the TTV genome, or parts thereof, to construct a vector for expression of cloned genes in culture or in gene therapy treatment. The vector can consist of the entire viral genome, either modified or wild type. It can also consist of parts of the genome such as the replication origin, specific genes, promoters or other control elements either by themselves or in conjunction with non-TTV sequences. A vector family is also proposed. The family would consist of identical sequences except for variable region(s) that prohibit re-infection of a previously infected host. The variable region(s) might encode epitopes from TTV isolates that do not show shared immunity, thus allowing multiple or prolonged treatment protocols.

Further provided is the use of TTV genomic diversity as a traceable marker to follow transmission of the virus between individuals, such traceability to be used in epidemiological or forensic studies.

DETAILED DESCRIPTION OF THE INVENTION

Figure 1:
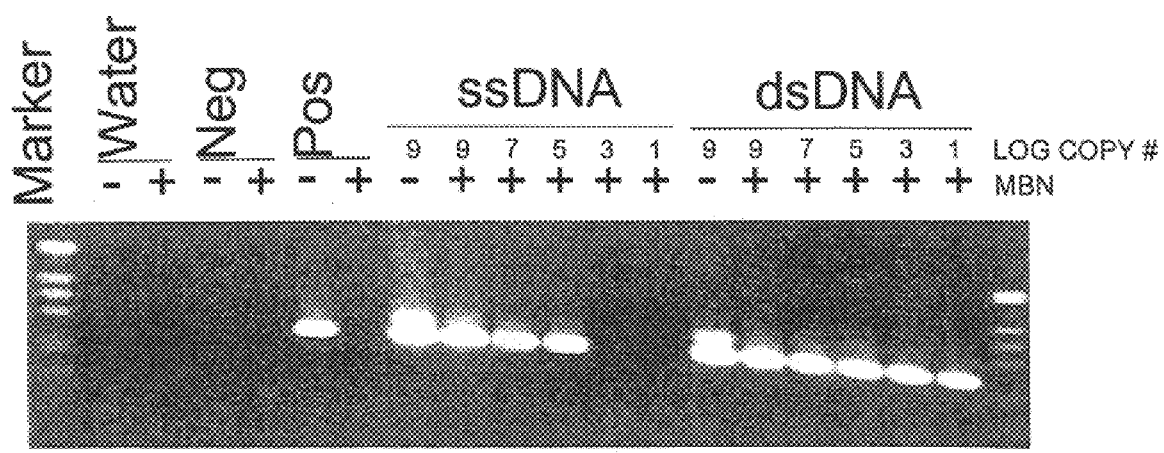
FIG. 1 shows the sensitivity of the TTV genome to mung bean nuclease where the log copy number of single stranded phagmid DNA (ssDNA) or double stranded plasmid DNA (dsDNA) present in control MBN digests are displayed.

The present invention relates to novel DNA oligomer primers and probes, methods of utilizing these primers and/or probes, test kits which comprise these primers and/or probes, and diagnostic methods for determining the presence of TTV target nucleotide sequences in human and in animals. Also provided are the use of TTV nucleotide sequences as nucleic acid vectors, the use of TTV nucleotide sequences for testing prior to transplantation or xenotransplantation, and the use of TTV nucleotide sequences as markers for determining the route of TTV transmission between individuals.

More specifically, portions of the nucleic acid sequences derived from TTV are useful as primers or probes to determine the presence of TTV in test samples, and to isolate naturally occurring variants. These sequences also make available polypeptide sequences of TTV antigens encoded within the TTV genome(s) and permit the production of polypeptides which are useful as standards or reagents in diagnostic tests and/or as components of vaccines. Isolation and sequencing of other portions of the TTV genome also can be accomplished by utilizing PCR primers and/or probes derived from these nucleic acid sequences, thus allowing additional primers, probes and polypeptides of the TTV to be established, which will be useful in the diagnosis and/or treatment of TTV, both as a prophylactic and therapeutic agent. These nucleic acid primers and probes are identified as SEQUENCE ID NOS. 52–59 and 60–71. These primers and probes hybridize to TTV sequence, or their complement, in regions of high sequence conservation. Thus, these primers and probes can be used in PCR assays to specifically and efficiently amplify TTV sequences with the reduced likelihood of failed amplification (and false-negative assay results) due to primer mismatches.

The present invention also provides test kits containing reagents which can be used for the detection of the presence and/or amount of polynucleotides derived from TTV. The test kit may comprise, for example, one or more containers such as vials or bottles, with each container containing a separate reagent such as a nucleic acid primer, probe or a cocktail of nucleic acid primers or probes. Other components such as buffers, controls, and the like, known to those of ordinary skill in art, may be included in such test kits.

The term "ITT Virus" or "TTV", as used herein, collectively denotes a viral species, and attenuated strains or defective interfering particles derived therefrom. This virus may be transmitted via person to person contact (including sexual transmission, respiratory and parenteral routes) or via intraveneous drug use. The methods as described herein will allow the identification of individuals who have acquired TTV. As described herein, the TTV genome is comprised of DNA. Analysis of the nucleotide sequence and deduced amino acid sequence of the TTV reveals that viruses of this group have a genome organization similar to yet distinct from that of the Circoviridae family. Similar to the Circoviridae, TTV is a non-enveloped virus which contains a single-stranded circular DNA genome. However, it should be noted that TTV demonstrated no sequence similarity with members of the Circoviridae based upon comparison of nucleic acid or deduced amino acid sequences using the BLAST algorithms, and the TTV virion and genome are much larger than those found for the Circoviridae. Thus, in view of the above, TTV, for purposes of the present invention, has been assigned to the family or genus Circinoviridae.

The term "similarity" and/or "identity" are used herein to describe the degree of relatedness between two polynucleotides or polypeptide sequences. The techniques for determining amino acid sequence "similarity" and/or "identity" are well-known in the art and include, for example, directly determining the amino acid sequence and comparing it to the seqeunces provided herein; determining the nucleotide sequence of the genomic material of TTV, and determining the amino acid sequence encoded therein, and comparing the corresponding regions. In general, by "identity" is meant the exact match-up of either the nucleotide sequence of TTV and that of another strain(s) or the amino acid sequence of TTV and that of another strain(s) at the appropriate place on each genome. Also, in general, by "similarity" is meant the exact match-up of amino acid sequence of TTV and that of another strain(s) at the appropriate place, where the amino acids are identical or possess similar chemical and/or physical properties such as charge or hydrophobicity. The programs available in the Wisconsin Sequence Analysis Package, Version 9 (available from the Genetics Computer Group, Madison, Wis., 53711), for example, the GAP program, are capable of calculating both the identity and similarity between two polynucleotide or two polypeptide sequences. Specifically, the GAP program uses the algorithm of Needleman and Wunsch (*J. Mol. Biol.* 48:443–453 (1970)) with the default penalties for gap creation and gap extension set at 50 and 3, respectively, for nucleotide alignments, and with the default penalties for gap creation and gap extension set at 12 and 4, respectively, for amino acid alignments. Other programs for calculating identity and similarity between two sequences such as FASTA (Pearson and Lipman, *Proc. Natl. Acad. Sci. USA* 85:24444–2448 (1988) and BLAST (Altschul et al., *J. Mol. Biol.* 215:403–410 (1990)) are known in the art.

Additionally, several parameters are applicable, either alone or in combination, in identifying a strain of TTV. For example, it is expected that the overall nucleotide sequence identity of the genomes between TTV strains will be about 45% or greater, since it is now believed that the TTV strains may be genetically related, preferably about 60% or greater, and more preferably, about 80% or greater.

Also, it is expected that the overall sequence identity of the genomes between TTV strains at the amino acid level will be about 35% or greater since it is now believed that the TTV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

A polynucleotide "derived from" a designated sequence for example, the TTV DNA, or from the TTV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, and is similar to, or complementary to, a region of the designated nucleotide sequence. Preferably, the sequence of the region from which the polynucleotide is derived is similar to, or complementary to, a sequence which is unique to the TTV genome. Whether or not a sequence is similar to, or complementary to, a sequence which is unique to a TTV genome, can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of TTV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

The terms "polynucleotide," "oligomer" and "oligonucleotide" are used interchangeably herein. The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

"TTV containing a sequence corresponding to a DNA" means that the TTV contains a polynucleotide sequence which is similar to or complementary to a sequence in the designated DNA. The degree of similarity or complementarity to the DNA will be approximately 50% or greater, will preferably be at least about 70%, and even more preferably will be at least about 90%. The sequence which corresponds will be at least about 70 nucleotides, preferably at least about 80 nucleotides, and even more preferably at least about 90 nucleotides in length. The correspondence between the TTV and the DNA can be determined by methods known in the art, and include, for example, a direct comparison of the sequenced material with the DNAs described, or hybridization and digestion with single strand nucleases, followed by size determination of the digested fragments.

"Purified viral polynucleotide" refers to a TTV genome or fragment thereof which is essentially free, i.e., contains less than about 50%, preferably less than about 70%, and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means a TTV polypeptide or fragment thereof which is essentially free, that is, contains less than about 50%, preferably less than about 70%, and even more preferably, less than about 90% of of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in, and are unique to, the designated polypeptide(s), usually TTV proteins. Immunological identity may be determined by antibody binding and/or competition in binding. These techniques are known to the routineer and also are described herein. The uniqueness of an epitope also can be determined by computer searches of known data banks, such as GenBank®, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

The term "individual" as used herein refers to vertebrates, particularly members of the mammalian species and includes but is not limited to domestic animals, sports animals, primates and humans; more particularly the term refers to tamarins, chimpanzees and humans.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

A "positive stranded genome" virus denotes that the genome, whether RNA or DNA, is single-stranded and encodes a viral polypeptide(s).

A "negative stranded genome" virus denotes that the genome, whether RNA or DNA, is single-stranded and is complementary to that of the "plus" strand.

The term "test sample" refers to a component of an individuals body which is the source of the analyte (such as, antibodies of interest, antigens of interest or polynucleotides of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

"Purified TTV" refers to a preparation of TTV which has been isolated from the cellular constituents with which the virus is normally associated, and from other types of viruses which may be present in the infected tissue. The techniques for isolating viruses are known to those skilled in the art and include, for example, centrifugation and affinity chromatography.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, duracytes and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing capture reagents on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes and other configurations known to those of ordinary skill in the art.

It is contemplated and within the scope of the invention that the solid phase also can comprise any suitable porous material with sufficient porosity to allow access by detection antibodies or polynucleotides, and a suitable surface affinity to bind antigens or polynucleotides. Microporous structures are generally preferred, but materials with gel structure in the hydrated state may be used as well. Such useful solid supports include but are not limited to natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen; synthetic polymers which may be prepared with suitably porous structures, such as vinyl polymers; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes such as films, sheets, beads or plates, or they may be coated onto or bonded or laminated to appropriate inert carriers, such as paper, glass, plastic films, or fabrics.

The porous structure of nitrocellulose has excellent absorption and adsorption qualities for a wide variety of reagents. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen, antibody or polynucleotide to the support. The irreversible binding of the antigen or antibody is obtained, however, in general, by adsorption on the porous material by poorly understood hydrophobic forces. Suitable solid supports also are described in U.S. Pat. No. 5,075,077.

The "indicator reagent" comprises a "signal generating compound" (also termed a "label") generates a measurable signal detectable by external means conjugated (attached) to a specific binding member for TTV. "Specific binding member" as used herein means a member of a specific binding pair. That is, two different molecules where one of the molecules through chemical or physical means specifically binds to the second molecule. In addition to being an antibody member of a specific binding pair for TTV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. Furthermore, specific binding pairs can include members that are analogs of the original specific binding members, for example, an analyte-analog. An immunoreactive specific binding member can be an antibody or fragment thereof, an antigen or fragment thereof, or an antibody/antigen complex including those formed by recombinant DNA molecules that bind either to TTV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The term "detection label" refers to a molecule or moiety having a property or characteristic which is capable of detection. A detection label can be directly detectable as with, for example, radioisotopes, fluorophores, chemiluminophores, enzymes, colloidal particles, fluorescent microparticles and the like; or a label may be indirectly detectable as with, for example, specific binding members. It will be understood that direct labels may require additional components such as, for example, substrates, triggering reagents, light, and the like to enable detection of the label. When indirect labels are used for detection, they are typically used in combination with a conjugate. A "conjugate" is typically a specific binding member which has been attached or coupled to a directly detectable label. Similar to the synthesis of solid phase reagents, coupling chemistries for synthesizing a conjugate are well known in the art and can include, for example, any chemical means and/or physical means that does not destroy the specific binding property of the specific binding member or the detectable property of the label.

The term "hapten", as used herein, refers to a partial antigen or non-protein binding member which binds to an antibody, but which does not elicit antibody formation unless coupled to a carrier protein. Examples of haptens include biotin, avidin, adamantane and carbazole.

"Analyte," as used herein, is the substance to be detected which may be present in the test sample. The analyte can be any substance for which there exists a naturally occurring specific binding member (such as an antibody), or for which a specific binding member can be prepared (such as a polynucleotide). Thus, an analyte is a substance that can bind to one or more specific binding members in an assay. "Analyte" also includes target nucleotide sequences and any antigenic substances such as haptens, antibodies and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

Embodiments which utilize ion capture procedures for immobilizing an immobilizable reaction complex with a negatively charged polymer, described in EP publication 0326100 and EP publication no. 0406473, can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0273115.

Also, the methods of the present invention can be adapted for use in systems which utilize microparticle technology including in automated and semi-automated systems wherein the solid phase comprises a microparticle (magnetic or non-magnetic). Such systems include those described in U.S. Pat. No. 5,244,630 and U.S. Pat. No. 5,089,424 which correspond to published EPO application Nos. EP 0425633 and EP 0424634, respectively.

The use of scanning probe microscopy (SPM) for analyte detection also is adaptable. In scanning probe microscopy, in particular in atomic force microscopy, the capture phase is adhered to a solid phase and a scanning probe microscope is utilized to detect antigen/antibody complexes which may be present on the surface of the solid phase. The use of scanning tunnel microscopy eliminates the need for labels that normally must be utilized in many immunoassay systems to detect antigen/antibody complexes. Such a system is described in U.S. patent application Ser. No. 07/662,147, now abandoned.

It is contemplated and within the scope of the present invention that the TTV group of viruses may be detectable in assays by use of synthetic, recombinant or native primers or probes that are common to all TT viruses (termed "universal" primers or probes). It also is within the scope of the present invention that different synthetic, recombinant or native primers or probes identifying different regions from the TTV genome can be used in assay formats. Such assay formats are known to those of ordinary skill in the art and are discussed hereinbelow.

Using determined portions of the isolated TTV nucleic acid sequences as a basis, oligomers of approximately eight nucleotides or more can be prepared, either by excision or synthetically, which hybridize with the TTV genome. Such oligomers are useful in identification of the viral agent(s), further characterization of the viral genome, as well as in detection of the virus(es) in diseased individuals. The natural or derived primers or probes for TTV polynucleotides are a length that allows the detection of unique viral sequences. While six to eight nucleotides may be a workable length, sequences of ten to twelve nucleotides are preferred, and those of about 20 nucleotides may be most preferred. These sequences preferably will derive from regions that lack heterogeneity. These primers or probes can be prepared using routine, standard methods including automated oligonucleotide synthetic methods. A complement of any unique portion of the TTV genome will be satisfactory. Complete complementarity is desirable for use as primers or probes, although it may be unnecessary as the length of the primers or probes is increased.

When used as diagnostic reagents, the test sample to be analyzed, such as blood or serum, may be treated such as to extract the nucleic acids contained therein. The resulting nucleic acid from the sample may be subjected to amplification techniques such as Ligase Chain Reaction (LCR), Polymerase Chain Reaction (PCR), Q-beta replicase, NASBA, etc.

The primers or probes can be made completely complementary to the TTV genome. Therefore, usually high stringency conditions are desirable in order to prevent false positives. However, conditions of high stringency should be used only if the primers or probes are complementary to regions of the TTV genome that lack heterogeneity. The stringency of annealing is determined by a number of other factors, including temperature, ionic strength, primer or probe length and primer probe concentration.

It is contemplated that the TTV genome sequences may be present in serum of infected individuals at relatively low levels, for example, approximately $10^2$–$10^3$ sequences per milliliter. This level may require that amplification techniques, such as the LCR or the PCR, be used in detection assays. The amplified sequence(s) then may be detected using an assay such as those known in the art. The primers or probes can be packaged in diagnostic kits which include the primer or probe nucleic acid sequences, which sequences may be labeled; alternatively, the primers or probes may be unlabelled and the ingredients for labeling could be included with the kit. The kit also may contain other suitably packaged reagents and materials needed or desirable for the particular amplification protocol, for example, standards as well as instructions for performing the assay.

Other known amplification methods which can be utilized herein include but are not limited to the so-called "NASBA" or "3SR" technique taught in *PNAS USA* 87:1874–1878 (1990) and also discussed in *Nature*: 350 (No. 6313):91–92 (1991) and Q-beta replicase.

PCR amplification also can be performed in situ utilizing the reagents described herein. In situ PCR involves taking morphologically intact tissues, cells or chromosomes through the nucleic acid amplification process to demonstrate the presence of a particular piece of genetic information. Since it does not require homogenization of cells and extraction of the target sequence, it provides precise localization and distribution of a sequence in cell populations. In situ amplification can identify the sequence of interest concentrated in the cells containing it. It also can identify the type and fraction of the cells in a heterogeneous cell population containing the sequence of interest. Both DNA and RNA can be detected.

Assays as described herein may utilize one viral antigen derived from any clone-containing TTV nucleic acid sequence, or from the composite nucleic acid sequences derived from the TTV nucleic acid sequences in these clones, or from the TTV genome from which the nucleic acid sequences in these clones are derived. Or, the immunoassay may use a combination of viral antigens derived from these sources. It also may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described herein. Signals also may be amplified by using biotin and avidin, enzyme labels or biotin anti-biotin systems, such as that described in pending U.S. patent application Ser. No. 08/608,849, now abandoned; Ser. No. 08/070,647, now abandoned; Ser. No. 08/418,981, now abandoned; and Ser. No. 08/687,785, now abandoned.

It should be noted that any of the diagnostic assays described herein may be utilized in connection with humans or animals. For example, one may wish to determine whether an animal (e.g., a goat, a dog, a cat, a cow, or a horse) has been exposed to the virus and act accordingly with respect to administration of anti-viral agents. Additionally, one may wish to administer vectors to the animal and thereby carry out gene therapy. Since animals have many of the same therapeutic needs and physical conditions as humans, the applicability of the methods described herein to animals as well as humans is quite apparent and is encompassed within the scope of the invention.

It should be noted that the TTV nucleic acid sequences may also be used to gain further information on the sequence of the TTV genome, and for identification and isolation of the TTV agent. Thus, it is contemplated that this knowledge will aid in the characterization of TTV including the nature of the TTV genome, the structure of the viral particle, and the nature of the antigens of which it is composed. This information, in turn, can lead to additional polynucleotide primers, polypeptides derived from the TTV genome, and antibodies directed against TTV epitopes useful for the diagnosis and/or treatment of TTV infections.

Synthetic oligonucleotides may be prepared using an automated oligonucleotide synthesizer such as that described by Warner, *DNA* 3:401 (1984). If desired, the synthetic strands may be labeled with $^{32}$p by treatment with polynucleotide kinase in the presence of $^{32}$p-ATP, using standard conditions for the reaction. DNA sequences including those isolated from genomic or libraries, may be modified by known methods which include site directed mutagenesis as described by Zoller, *Nucleic Acids Res.* 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned.

Polymerase chain reaction (PCR) and ligase chain reaction (LCR) are techniques for amplifying any desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to geometrically increase the number of target sequence molecules. PCR is disclosed in U.S. Pat. No. 4,683,195 and No. 4,683,202.

LCR is an alternate mechanism for target amplification. In LCR, two sense (first and second) probes and two antisense (third and fourth) probes are employed in excess over the target. The first probe hybridizes to a first segment of the target strand and the second probe hybridizes to a second segment of the target strand, the first and second segments being positioned so that the primary probes can be ligated into a fused product. Further, a third (secondary) probe can hybridize to a portion of the first probe and a fourth (secondary) probe can hybridize to a portion of the second probe in a similar ligatable fashion. If the target is initially double stranded, the secondary probes will also hybridize to the target complement in the first instance. Once the fused strand of sense and antisense probes are separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described in EP-A-320,308, hereby incorporated by reference. Other aspects of LCR technique are disclosed in EP-A-439,182, which is incorporated herein by reference.

In one embodiment, the present invention generally comprises the steps of contacting a test sample suspected of containing a target TTV nucleotide sequence with amplification reaction reagents comprising an amplification primer pair, that can hybridize with a region of the TTV sequences, followed by amplification with another set of primers. (Alternatively, a primer pair may be used followed by the use of a probe.) Primers and probes employed according to the methods herein may be labeled with capture and detection labels wherein one primer of the initial pair is labeled with one type of label and one primer of the second pair (or sole probe) is labeled with the other type of label.

After the amplicon products are formed, they are detected by gel electrophoresis and visualization with ethidium bromide as is know in the art. Alternatively, standard heterogeneous assay formats are suitable for detecting the products using the detection labels and capture labels present on the primers. The products can be bound to a solid phase reagent by virtue of the capture label and detected by virtue of the detection label. In cases where the detection label is directly detectable, the presence of the products on the solid phase can be detected by causing the label to produce a detectable signal, if necessary, and detecting the signal. In cases where the label is not indirectly detectable, the captured products can be contacted with a conjugate, which generally comprises a binding member attached to a directly detectable label. The conjugate becomes bound to the complexes and the conjugate's presence on the complexes can be detected with the directly detectable label. Thus, the presence of the products on the solid phase reagent can be determined. Those skilled in the art will recognize that wash steps may be employed to wash away non-captured amplicon or primer as well as unbound conjugate.

A test sample is typically anything suspected of containing a target sequence. Test samples can be prepared using methodologies well known in the art such as by obtaining a specimen from an individual and, if necessary, disrupting any cells contained therein to release target nucleic acids. Although the target sequence is described as single stranded, it also is contemplated to include the case where the target sequence is actually double stranded but is merely separated from its complement prior to hybridization with the amplification primer sequences. In the case where PCR is employed in the preferred method, the ends of the target sequences are usually known. In cases where LCR or a modification thereof is employed in the preferred method, the entire target sequence is usually known. Typically, the target sequence is a nucleic acid sequence such as for example RNA or DNA.

The method provided herein can be used in well known amplification reactions that thermal cycle reaction mixtures, particularly in PCR and GLCR. Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one where complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filing the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

Typically, the PCR primer sequences or the LCR probe sequences are in the range of between 20 and 50 nucleotides long, more typically in the range of between 20 and 30 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labelling oligonucleotides such as the primers or probes of the present invention. Enzo Biochemical (New York, N.Y.) and Clontech (Palo Alto, Calif.) both have described and commercialized oligo-labeling techniques. For example, a primary amine can be attached to a 3' oligo terminus using $3^1$-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, U.S. patent application Ser. No. 08/625,566, now abandoned, and U.S. Pat. No. 5,290,925, which are each incorporated herein by reference, teach methods for labeling oligos at their 5' and 3' termini, respectively. Publications WO92/10505, published Jun. 25, 1992 and WO 92/11388 published Jul. 9, 1992 teach methods for labeling oligos at their 5' and 3' ends respectively. According to one known method for labeling an oligonucleotide, a label-phosphoramidite reagent is prepared and used to add the label to the oligonucleotide during its synthesis. See, for example, N. T. Thuong et al., Tet. Letters 29(46):5905–5908 (1988); or J. S. Cohen et al., published U.S. patent application Ser. No. 07/246,688 (NTIS ORDER No. PAT-APPL-7–246,688) (1989). Preferably, oligos are labeled at their 3' and 5' ends.

Capture labels are carried by one or more of the primers (or the probe) and can be a specific binding member which forms a binding pair with the solid phase reagent's specific binding member. It will be understood, of course that one or more primers and/or the probe itself may serve as the capture label. For example, in the case where a solid phase reagent's binding member is a nucleic acid sequence, it may be selected such that it binds a complementary portion of the primer or probe to thereby immobilize the primer or probe to the solid phase. In the case where the primer or probe itself serves as the capture label, at least a portion of the primer or probe will be free to hybridize with a nucleic acid on a solid phase.

Generally, amplicon members can be detected using techniques commonly employed to perform heterogeneous immunoassays. Preferably, in this embodiment, detection is performed according to the protocols used by the commercially available Abbott LCx® instrumentation (Abbott Laboratories; Abbott Park, Ill.).

The primers disclosed herein are useful in typical PCR assays, wherein the test sample is contacted with a pair of primers, amplification is performed, amplification then occurs with another pair of primers (or a probe is utilized) and the products are detected.

Another method proposed herein pertains to the use of the TTV genome, or parts thereof, in a nucleic acid vector suitable for expression of cloned genes, either in cell culture or in the context of gene therapy. A wide range of chimeric TTV-based vectors incorporating nucleic acid sequences from multiple sources could be constructed by one skilled in the art [Maniatis (1989) "Molecular Cloning: A Laboratory Manual"]. In particular, portions of the TTV genome responsible for specific viral functions (e.g., replication, expression, virion formation), in conjunction with nucleic acid sequences that confer other desired traits, may be propagated as plasmid clones. The TTV sequence of interest may then be excised from the plasmid clone using appropriate restriction enzymes, and gel purified. A ligation reaction may then be performed containing the gel purified TTV sequence in conjunction with similarly prepared non-TTV nucleic acid sequences that confer other desired traits (e.g., the ability to replicate, and be selected for, in procaryotic cells). The desired ligation product may then be clone purified and confirmed by DNA sequencing. The amount of TTV present in such a vector may range from as few as 20 nucleotides up to the complete TTV genome. Furthermore, the TTV sequences used can be either wild type or modified, using commercially available in vitro mutagenesis kits, to alter specific properties such as vector capacity, efficiency of replication, host cell range, transmission and the like.

Alternatively, the entire TTV genome could be used, either in its wild type form or modified to alter specific properties such as vector capacity, efficiency of replication, host cell range, transmission and the like.

With respect to conditions for growth of TTV in cell culture, various cell lines (e.g., fibroblasts, hepatocytes, HeLa cells) and growth media may be tested for the ability to propagate the virus. Furthermore, studies may be done to establish the site(s) of TTV replication in animals and humans by testing for the presence, in various tissues, of the TTV "plus" strand (i.e. non-genomic strand). This information is significant if the vector depends on TTV sequences for replication and/or transmission. Such information is not as important if the vector does not replicate within the host cell or transmission between cells, or if such functions are provided by other non-TTV sequences.

Introduction of the vector into cell culture may be achieved by several common methods known to those skilled in the art, including transformation or micro-injection of purified DNA into the cells, and infection of cells by virions containing the vector genome. Similarly, administration of the vectors to animals or humans could be accomplished by several methods. Purified vector DNA or infectious virions can be injected directly into the organism (e.g. intra-muscular or intravenous injection). Alternatively, cells into which the vector has been previously introduced (described above) can be injected into the organism, or infectious virions can be introduced through mucous membranes (e.g., in aerosol form through the lining of the lung).

Potential applications of a TTV-based vector are the same as for vectors already in use. This includes cell culture production of useful proteins, such as antigens for vaccines or diagnostic tests, and enzymes of clinical or research value. Gene therapy [Anderson (1992) "Human Gene Therapy", Science 256:808–813] for replacement of defective genes such as the LDL receptor for hypercholesterolemia [Wilson et al. (1990) "Prospects for Gene Therapy of Familial Hypercholesterolemia", *Mol. Biol. Med.* 7:223–232; Grossman et al. (1992) "Frontiers in Gene Therapy: LDL Receptor Replacement for Hypercholesterolemia", J. Lab. Clin. Med. 5:457–460] or hypoxanthine-guanine phosphoribosyltransferase for gout [Davidson et al. (1989) "Human Hypoxanthine-guanine Phosphoribosyltransferase Deficiency: The *Molecular Defect in a Patient with Gout (HPRT$_{ASHVILLE}$)*", J. Biol. Chem. 264:520–525], are but a few of the conditions [Schwandt et al. (1989) "Genetic-disorders of Metabolism in Adults", Internist 30:547–555] possibly treatable with a TTV-based vector.

As used herein, the term "vector" refers to a nucleic acid sequence that can be ligated to other nucleic acid sequences, conferring on these other sequences any or all of the following: the ability to be introduced into cells, to be replicated within cells, and to be expressed within cells or to be transmitted between cells.

A family of closely related TTV vectors is also proposed. Members of the family would vary chiefly in those regions of the TTV genome that encode epitopes recognized by the immune system of a host, resulting in clearance of the vector. The epitope-encoding region for each vector would be derived from a TTV isolate that does not show shared immunity with any of the other members of the vector family. Existence of such non-cross reactive TTV isolates is strongly suggested by the demonstration of co-infections and the high prevalence level in humans. The appearance, then loss, of detectable TTV in an experimentally infected chimpanzee, and the common inability of DNA virus-based gene therapy to successfully repeat a second round in humans, suggests that immunity is a potential concern. Thus, the vector panel described above could be used to maintain or repeat treatment of an individual who has developed immunity to the initial vector.

A further method is proposed that relies on the high sequence diversity of the TTV genome. In this method TTV genomic DNA would be isolated from two or more individuals, amplified and sequenced, either partially or in full. Comparison of the sequences would then be performed across a region of known high variability. Furthermore, the region should be sufficiently large such that the chance of two isolates having the exact, or nearly exact, nucleic acid sequence is minimized. The more similar the TTV sequences are to one another, the more likely it is that the individuals involved were infected from a common source or that one individual infected the other. Therefor, even in a population with a high level of pre-existing TTV infections, studies can be done on the specific mode of transmission of TTV within social groups, or under controlled conditions.

Not only is this information useful from an epidemiological standpoint, but it also has applications to fields such as forensics. In this embodiment, TTV genomic sequence could be used to establish previous contact between individuals and, depending on the mode of transmission, what the nature of the contact was. In particular, existing data suggest that TTV can be transmitted by parenteral exposure. (Okamoto et al., *Hepatology Research* 10:1–16 (1998; Simmonds et al., *The Lancet* 352:191–194 (1998; Desai et al., *J. Infect. Dis.* in press:(1999)) Furthermore, the presence of TTV detected in fecal samples (Okamoto et al., *J. of Med. Virol.* 56:128–132 (1998)) suggests that this virus might also be spread by the fecal-oral oral route. In addition, it is conceivable that other routes of transmission are possible (e.g., sexual or aerosal). Additional studies will be needed to address these possibilities. Of course, independent of how TTV is spread, the high level of sequence divergence noted among the isolates identified to date (see Example 5) implies that one could use the variability of the TTV genome to establish contact between people. For example, since TTV is transmitted parenterally, one could potentially determine whether intravenous drug users share contaminated needles. Similarly, if TTV is transmitted sexually, one could potentially demonstrate sexual contact between two individuals, months after such contact, by comparing TTV sequences. Thus, the TTV virus may be utilized for forensic purposes.

Moreover, xenotransplantation presents another area where assays for TTV may prove useful. Although xenogenic tissue grafts may help solve the current shortage of organ donation, the possible zoonosis of viruses from the transplanted organ is a concern (*Curr. Opin. Immunol.* 10:539–542 (1998)). Specifically, the presence of an animal virus in transplanted tissue may result in graft rejection or, due to the immunosupressed state of a transplant recipient, exacerbated disease and death. Therefore, identifying TTV-free animals for tissue donation would appear prudent. Thus, encompassed within the present invention is a method of screening potential organs donors for TTV using an assay similar to that described in detail in Example 7. Animals that test positive for genomic TTV sequences in their serum or plasma could then be rejected as possible donors, if appropriate.

The present invention will now be described by way of examples, which are meant to illustrate, but not to limit, the spirit and scope of the invention.

EXAMPLES

Example 1

Transmission of TTV to Non-human Primates

Several studies have observed a high prevalence of TTV in individuals at risk for infection with parenterally transmitted viruses, suggesting that TT virus can be transmitted by blood and/or blood products. However, there have been no cases of TTV transmission reported in the literature to date. To investigate whether TTV is a transmissible agent, and if it can be transmitted parenterally, serum or plasma from two chronic nonA-GBV-C hepatitis patients known to be infected with TTV were intravenously inoculated into chimpanzees.

Non-human primate transmission studies were conducted at the Southwest Foundation for Biomedical Research in San Antonio, Tex. All animals were maintained and monitored according to protocols that met all relevant requirements for the humane care and ethical use of primates in an approved facility. Baseline serum levels were established for the liver-specific enzymes alanine aminotransferase (ALT), gamma-glutamyltransferase (GGT) and aspartate aminotransferase (AST). Animals were inoculated intravenously with TTV-containing human serum or plasma from individuals diagnosed with chronic nonA-E hepatitis and then monitored twice weekly for serum levels of the above liver-specific enzymes. Chimpanzee 314 (CH314) was inoculated with 20 ml of human plasma from patient A and chimpanzee 306 (CH306) was inoculated with 2.0 ml human serum from patient B.

TTV viremia was determined by nested PCR using a modified primer set orginally described by (Simmonds et al., The Lancet 352:191–194 (1998)). First round primers were A5430 (SEQ ID NO. 1) and a modified A5427 primer (SEQ ID NO. 2); second round primers were A8761 (SEQ ID NO. 3) and A5432 (SEQ ID NO. 4) was used in the first round amplification. PCR used total nucleic acids extracted from 100 µl chimpanzee serum using the QIAamp Blood Kit (QIAGEN, Chatsworth, Calif.) as directed by the manufacturer. Nucleic acids were ethanol precipitated and suspended in 25 µl of water. First round PCR utilized 4 µl of the extracted nucleic acids in a 20 µl reaction volume. Cycling conditions for first round (45 cycles) and second round (40 cycles) amplification were 94° C. for 1 minute followed by 94° C./20 sec, 55° C./30 sec, and 72° C./30 sec; final extension at 72° C./5 min. Products were analyzed by agarose gel electrophoresis with visualization by ethidium bromide fluorescence. The approximate titers of TTV in the human inocula were determined by making serial 2-fold dilutions of extracted nucleic acids and performing PCR as described above.

Fecal material was suspended in PBS (15% w:v), vortexed and centrifuged at 3000×g, 4° C. for 10 min. The supernatant was transferred to a clean tube and centrifuged at 8000×g at 4° C. for 5 minutes. Nucleic acids were extracted from 200 µl of the resulting supernatant using the QIAamp Blood Kit. Nucleic acids were ethanol precipitated and resuspended in 15 µl water. TTV PCR was performed as described above.

Twenty ml of plasma from one patient (approximate TTV titer: $2 \times 10^3$ genome copies/ml) was inoculated into chimpanzee 314 (CH314). Two ml of serum from a second patient (approximate TTV titer: $1 \times 10^3$ genome copies/ml) was inoculated into chimpanzee 306 (CH306). TTV DNA was detected in CH314 serum for 28 days starting 93 days post-inoculation (PI, Table 1).

TABLE 1

Presence of TTV in chimpanzee serum

| CHIMP 314 | | CHIMP 306 | |
|---|---|---|---|
| Weeks Post-Inoculation | TTV PCR | Weeks Post-Inoculation | TTV PCR |
| −0.7 | − | −0.2 | − |
| 1 | − | 1 | − |
| 2 | − | 2 | − |
| 3 | − | 3.3 | − |
| 5 | − | 4.3 | − |
| 7 | − | 6 | − |
| 9.3 | − | 8.3 | − |
| 10.3 | − | 10.3 | − |
| 13.3 | + | 12.3 | − |
| 15.3 | + | 19 | − |
| 17.3 | + | 21 | − |
| 32.3 | − | 21.3 | + |
| 33.3 | − | 22 | + |
| 34.3 | − | 23 | + |
| | | 25 | + |
| | | 26.3 | + |
| | | 27.3 | + |
| | | 28 | + |
| | | 29 | + |
| | | 30 | + |
| | | 31 | + |

The duration of the viremia is unclear because samples between 121 and 226 days PI were not available. However, sera collected later than 226 days were negative. TTV DNA was detected in CH306 serum starting at 149 days PI and remained positive until 219 days PI, at which time viral DNA became undetectable. The later appearance of TTV viremia in CH306, compared to CH314 (149 vs. 93 days PI), may be due to the lower volume and titer of the inoculum used. Nucleic acids extracted from CH306 fecal samples spanning 133–175 days post-inoculation were tested for TTV via nested PCR, however TTV DNA was not detected. Thus, TTV is either (a) not shed in the feces of CH306, or (b) not present in the feces during the time frame tested, or (c) below the limit of detection. TTV sequences present in the human inocula and in the corresponding chimpanzee recipients were found to be 100% identical, while the sequences of the TTV PCR products from the two human inocula were only 91% identical (data not shown). The complete conservation of TTV sequences between source and recipient indicates that TTV infection was derived from its corresponding inoculum, thus demonstrating the infectious nature of the inoculum and the parenteral transmissibility of the virus. Neither chimpanzee exhibited any biochemical or histologic evidence of hepatitis.

Example 2

Biophysical Characterization of TTV

In an effort to further characterize TT virus, the studies of Nishizawa et al. and Okamoto et al. (Nishizawa et al., Biochem Biophys Res Commun 241:92–97 (1997); Okamoto et al., Hepatol. Res. 10:1–16 (1998)) were extended and repeated through biophysical characterization of the virus. The present data confirm the single-strandedness of the DNA genome and strongly suggest that it is circular and not linear as previously believed. In addition, nuclease protection assays using strand-specific probes suggests that TTV possesses a negative-stranded genome.

Example 2.1

Estimation of TTV Particle Size

Filtration studies to determine the approximate size of the putative virion utilized 50 µl of TTV positive serum combined with parvovirus B19-containing human serum (10 virus particles). The sample was diluted to 1.0 ml with phosphate buffered saline (PBS) and spun for 10 min at 12,000×g and 4° C. The supernatant was passed sequentially through 13 mm polycarbonate filters (Costar) with decreasing pore sizes of 200 nm, 100 nm, 50 nm, 30 nm and 15 nm. PBS (100 µl) containing 0.1 mg/ml bovine serum albumin was passed through all filters prior to use. Aliquots (100 µl) of unfiltered serum and the resulting filtrates were extracted for total nucleic acid using the DNA/RNA Isolation Kit (Amersham Life Science Inc., Arlington Heights, Ill.) as directed by the manufacturer. TTV and B19 sequences were detected by PCR (20 µl final reaction volume) by using AmpliTaq Gold DNA polymerase (Perkin Elmer, Foster City, Calif.) and 2 µl (20%) of each extracted sample. TTV primers were as described in Example 1 (SEQ ID NOS. 7 and 8). Parvovirus B19 primers were: B19-forward (SEQ ID NO. 9) and B19-reverse (SEQ ID NO. 10). Reactions were heated 8 min at 94° C. followed by 40 cycles of 94° C./20 sec, 55° C./30 sec and 72° C./30 sec, followed by 3 min final extension at 72° C. Second round of amplification was performed as described above using an aliquot of the first round products and either the same primers (B19, SEQ ID NOS. 5 and 6) or nested primers (TTV, SEQ ID NOS. 3 and 4). Products were analyzed by agarose gel electrophoresis with visualization by ethidium bromide fluorescence.

As expected, parvovirus B19 particles (a nonenveloped, single-stranded DNA virus with a reported diameter of 18 nm to 22 nm) was detected in the 200 nm, 100 nm, 50 nm and 30nm filtrates, but not in the 15 nm filtrate. TTV was detected in the 200 nm, 100 nm, and 50 nm filtrates but not in the 30 nm or 15 nm filtrates. Thus, TTV virions appear to exist in serum with a particle diameter between 30 and 50 nm.

Example 2.2

Determination of TTV Buoyant Density

Human sera containing TT virus (200 µl) or parvovirus B19 (20 µl, approximately 2 ng B19 DNA) were mixed and centrifuged at 14,000×g for 15 minutes at 4° C. Supernatants were combined and mixed with 11.5 ml CsCl (1.302 g/ml). Isopycnic gradients were formed by centrifugation in a Beckman SW41Ti rotor at 35,000 rpm (150,000×g) for 65 hours at 6° C. Fractions (≈800 µl) were collected from the bottom of each gradient, refractive indices were measured to determine the density, and 200 µl of each fraction was extracted for total nucleic acids using the High Pure Viral RNA kit (Boehringer Mannheim, Indianapolis, Ind.). One-tenth of the isolated nucleic acid was tested for TTV or B19 by PCR using AmpliTaq Gold (Perkin Elmer, Foster City, Calif.) as directed by the manufacturer. PCR reactions (20 µl) utilized 1 µM primers (TTV: SEQ ID NOS. 7 and 8, B19: SEQ ID NOS. 9 and 10). Reactions were thermocycled (94° C., 9 min; 40 cycles of 94° C./20 sec, 55° C./30 sec, 72° C./30 sec; final extension at 72° C./10 min) and 10 µl from each reaction were separated by agarose gel electrophoresis, capillary transferred to Hybond-N+ (Amersham, Arlington Heights, Ill.), and visualized via Southern hybridization using an amplicon-specific $^{32}$P-labeled DNA probe.

PCR analysis of the gradient fractions located TTV in fractions with a density of 1.31–1.34 g/ml (data not shown). This is similar to the CsCl buoyant density reported by Okamoto et al. (Okamoto et al., *Hepatol. Res.* 10:1–16 (1998)). In contrast, parvovirus B19 was found in fractions with a density of 1.38–1.51 g/ml (data not shown). Thus, TTV possesses a buoyant density significantly lighter than parvovirus B19.

Example 2.3

Demonstration of the Single-stranded Nature of the TTV Genome

To investigate whether the TTV genome was single or double stranded, serum nucleic acids obtained using the DNA/RNA Isolation Kit (USB) were treated with Mung Bean Nuclease (NEB, Beverly, Mass.) at a final concentration of 1.0 U/µl for 30 minutes at 30° C (10 µl volume). Ten microliters of 50 mM Tris (pH 8.9) was added and the samples heated to 99° C. for 5 minutes. Samples were then diluted to 100 µl with PCR reaction mix to achieve 1×concentration and amplified for 35 cycles (95° C., 20 seconds; 55° C., 30 seconds; 72° C., 30 seconds) with TTV-specific primers (SEQ ID NOS. 11 and 12). Heminested PCR reactions were then performed using 5 µl of the first round product with SEQ ID NOS. 13 and 12. Both TTV positive and negative serum samples were tested, and the experiment was controlled by using a double-stranded plasmid (pGEM-T EASY, Promega, Madison, Wis.) containing a 1.3 kbp insert derived from TTV and a single-stranded phagmid of the same plasmid. Phagmid were produced as described (Sambrook et al., (1989)) using R408 helper phage (Stratagene, La Jolla, Calif.). Single-stranded phagmid DNA was isolated with the QIAquick Spin M13 kit (Qiagen, Chatsworth, Calif.) and quantitated by UV absorbance.

PCR amplification of these nucleic acids revealed the presence of the viral DNA prior to, but not following digestion with MEN (FIG. 1). Under the same reaction conditions, double-stranded plasmid DNA containing a 1.3 kbp fragment of the TTV genome was resistant to MBN digestion, while single-stranded phagmid DNA derived from the same plasmid was not. This result indicates that the genome of TT virus is single-stranded, at least within the region amplified by the primers used to detect the virus in these experiments.

Example 2.4

Determination of TTV Genome Polarity

To establish the polarity of the TTV genome, a hybridization/nuclease protection assay was performed using serum total nucleic acids containing TTV DNA and strand-specific RNA run-off transcripts made from plasmids containing identical TTV sequences, but in opposite orientations. Reduction of template plasmid DNA concentration to below detectable limits was achieved by repeated digestion with DNAse I and organic extraction with TRIzol reagent (GibcoBRL, Gaithersburg, Md.). Control experiments used plus or minus strand, single-strand phagmid DNA made from the same plasmids.

Total nucleic acid was extracted as above from TTV-positive human serum (100 µl) with a sequence identical to that of the cloned TTV sequence over the region to be analyzed, and resuspended in 40 µl of water. Plus or minus strand RNA transcripts (2 ng, 10$^{10}$ copies) were mixed, in separate reactions, with (a) plus or minus strand phagmid DNA (300 copies), (b) 10 µl of the extracted nucleic acids, and (c) water without DNA. The samples were dried under vacuum, dissolved in 8 µl of 30 mM EPPS, pH 8.1 containing 3 mM EDTA, overlaid with mineral oil and heated for 3 minutes at 99° C. After adding 2 µl of NaCl (5M), the samples were hybridized at 67° C. for 21 hours. One half (5 µl) of each hybridization was added to 45 µl buffer (33.3 mM sodium acetate, pH 5.2; 1.44 mM $ZnSO_4$; 5.56 glycerol), with or without Mung Bean Nuclease (6 Units/reaction), and incubated 30 minutes at 30° C. The nuclease was inactivated by adding 6 µl of 467 mM Tris-HCl, pH 8.9; 14 mM EDTA and heating 5 minutes at 99° C. Nucleic acid was ethanol precipitated and resuspended in 20 µl water. Four microliters of each sample was tested for the presence of TTV sequences by nested PCR (20 µl) followed by agarose gel electrophoresis as described above. The first round primers were A8761 (SEQ ID NO. 3) and A1 (SEQ ID NO. 14); second round primers were S2 (SEQ ID NO. 15) and A2 (SEQ ID NO. 16). These primers are specific for, and contained within, the cloned TTV region from which run-off transcripts and phagemid were made.

In the absence of nuclease, TTV was always detected except in the RNA-only hybridizations (Table 2). In the presence of nuclease, however, TTV viral DNA was detected only in hybridizations containing plus-strand RNA. The TTV-containing phagemid DNA controls were detected only when the hybridizations contained the opposite strand RNA. These results strongly suggest that TTV is a negative-stranded DNA virus.

TABLE 2

| Hybridization[a] | | PCR Detection of TTV | |
|---|---|---|---|
| RNA | DNA | Without MBN[c] | With MBN |
| Plus[b] | Plus | + | − |
| Plus | Minus | + | + |
| Plus | TTV | + | + |
| Plus | None | − | − |
| Minus | Plus | + | + |
| Minus | Minus | + | − |
| Minus | TTV | + | − |
| Minus | None | − | − |

[a]Nucleic acids present in the hybridization
[b]The strand polarity of the nucleic acid, plus or minus
[c]Treatment of the hybridization with or without Mung Bean Nuclease (MBN)

Example 3

Genomic Extension and Demonstration of the Circular Nature of TTV

To obtain the genomic sequence, total nucleic acids were extracted from a West African individual (GH1) using the DNA/RNA Isolation Kit (Amersham Life Science Inc., Arlington Heights, Ill.) as recommended by the manufacturer. Initial anchored PCR extension products were generated up- and down-stream of the N22 clone region (Nishizawa et al., *Biochem Biophys Res Commun* 241:92–97 (1997)) by anchored PCR (Sorensen et al., *J. of Virol.* 67:7118–7124 (1993); Leary et al., *J. of Med. Virol.* 48:60–67 (1996)). The TTV-specific primers used to obtain sequences upstream of the N22 region were: N22-A1 (SEQ ID NO. 17) and N22A2 (SEQ ID NO. 18). The anchored primers used to obtain sequences downstream of the N22 region were: N22-S1 (SEQ ID NO. 19) and N22-S2 (SEQ ID NO. 20). To test the possibility that the TTV genome is circular, inverted PCR using nested primers derived from the anchored PCR products was performed with Takara LA TAQ (PanVera Corporation, Madison, Wis.) as described by the manufacturer using the following primers: UFGH1-A1 (SEQ ID NO. 21), UFGH1-A2 (SEQ ID NO. 22), DFGH1-S1 (SEQ ID NO. 23), and DFGH1-S2 (SEQ ID NO. 24). The circular nature of the virus was confirmed by nested genome-length PCR using primers derived from the N22 region and Takara LA TAQ (first round, UFTTV1: SEQ ID NO. 25 and DFTTV1: SEQ ID NO. 26; second round, UFTTV2: SEQ ID NO.27 and DFTTV2: SEQ ID NO. 28). All PCR products were cloned into pGEM-T EASY vector (Promega, Madison, Wis.) and 2–4 clones sequenced. Sequencing reactions were performed with ABI Big Dye or Prism dGTP Big Dye (Applied Biosystems-Perkin-Elmer, Foster City, Calif.). Reactions were electrophoresed under denaturing conditions and sequence data collected on the Applied Biosystems 377 DNA Automated Sequencer as directed by the manufacturer. Sequences were compiled and edited using Sequencher version 3.0 (Gene Codes Corp., Ann Arbor, Mich.) and analyzed using the programs of the Wisconsin Sequence Analysis Package, version 9.0. The genomic sequence TTV-GH1 is SEQ ID NO. 29.

To obtain genome length sequence of TTV, anchored PCR was performed on nucleic acids extracted from the serum of the West African individual (GH1). Amplified genome fragments were generated upstream (1766 bp) and downstream (882 bp) from the N22 region of TTV-TA278 (Nishizawa et al., *Biochem Biophys Res Commun* 241:92–97 (1997)). Assuming that the TTV genome was circular, inverted PCR utilizing upstream anti-sense primers and downstream sense primers was performed, generating a 1300 bp product representing the remainder of the genome. The circular structure of the viral genome was reproducibly confirmed by nested genome-length PCR originating from the N22 region that produced the expected product of approximately 3700 bp. The genomic sequence of this isolate (designated GH1) comprises 3852 nucleotides (FIG. 2), 113 nucleotides longer than that of TTV-TA278 (Okamoto et al., *Hepatol. Res.* 10:1–16 (1998)). This additional sequence, located at the extreme 3'-end of the linear TA278 sequence (positions 3740–3852, SEQ ID NO. 29), consists of 89% G or C residues and possesses multiple inverted repeats. Alignment of TTV-GH1 and TTV-TA278 reveals 93% identity across the entire genome. The region with the lowest degree of conservation lies between bases 1440–1827, SEQ ID NO. 29 and exhibits only 73.6% identity. The region of highest identity lies between bases 2240–2911, SEQ ID NO. 29, exhibiting 99.5% identity. Both TTV-TA278 (Okamoto et al., *Hepatol. Res.* 10:1–16 (1998)) (GenBank accession no. AB008394) and TTV-GH1 (SEQ ID NO. 29) encode two large open reading frames of 203 (SEQ ID NO. 30) and 770 amino acids (SEQ ID NO. 31) (FIG. 2) exhibiting 95 and 96% identity between the isolates. The ORF1 protein of both isolates possesses an arginine-rich region at its amino terminus (44 of first 82 amino acids, SEQ ID NO. 31). The ORF1 regions from amino acids 1–274 exhibit 100% identity, but positions 275–405 exhibit only 69% identity. The remainder of the ORF1 protein is 100% conserved between the two isolates. No significant identity with non-TTV sequences was obtained upon BLAST analysis of TTV-GH1 against the GenBank or SWISPROT databases.

Figure 2A:
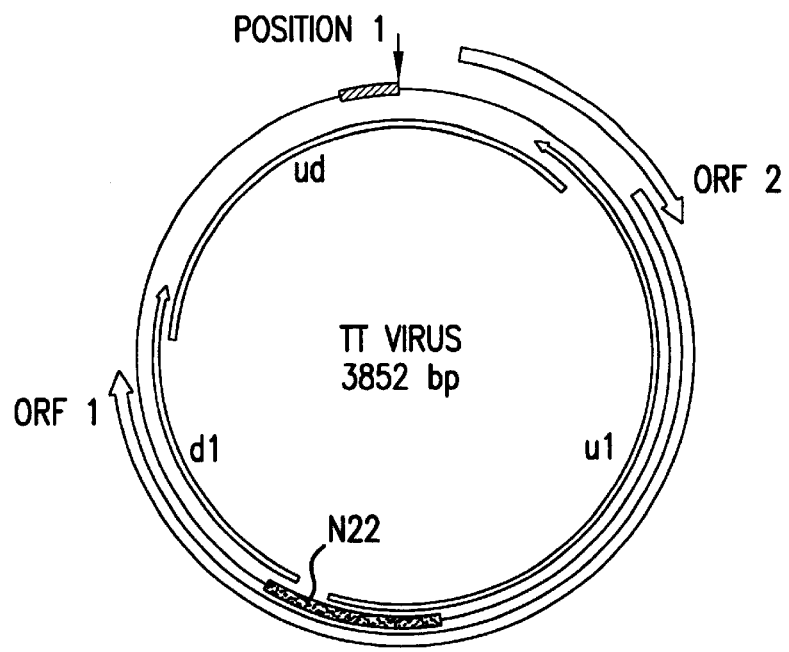
FIG. 2 shows TTV circular genome, where (A) displays the N22 clone sequence (gray box) described by Nishizawa et al., the anchored PCR extension clones extending upstream (u1) and downstream (d1) from N22, the inverse PCR product (ud) that overlaps the anchored PCR products, and the 113 nucleotide sequence identified in the GH1 (crosshatched box), and where (B) displays the initial 260 base region analyzed (Example 5), the amplicons obtained during genomic extension (thin lines), and the approximate position and orientation of conserved ORFs.
Figure 2B:
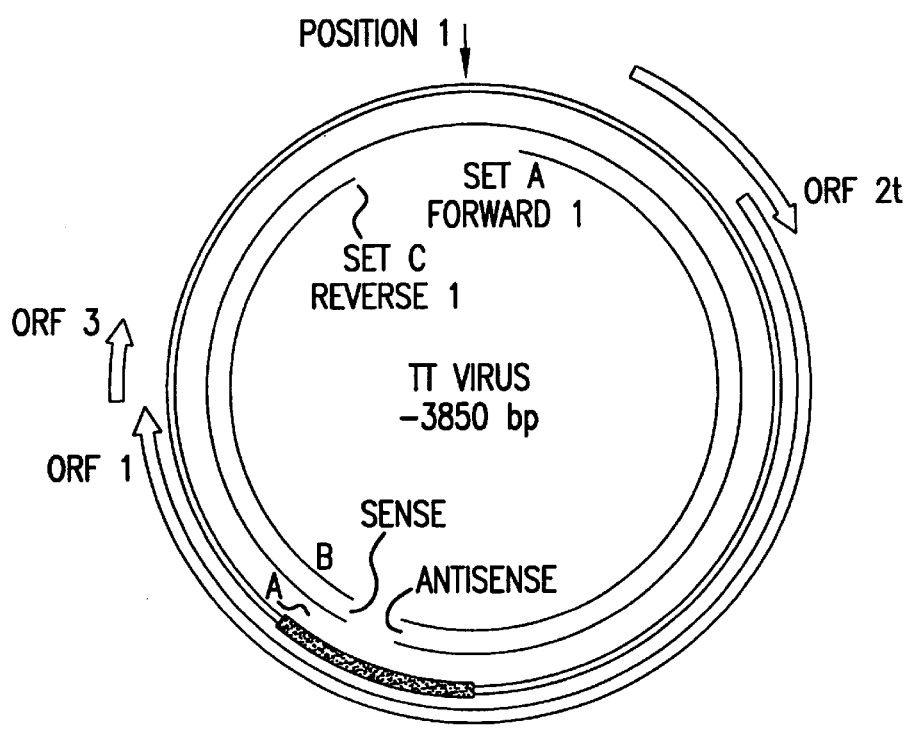

Previous interpretation of biophysical and molecular data suggested that TT virus resembled members of the Parvoviridae (Okamoto et al., *J. of Med. Virol.* 56:128–132 (1998); Okamoto et al., *Hepatol. Res.* 10:1–16 (1998)). In Example 2, we confirmed that TTV possesses a single-stranded DNA genome, consistent with the Parvoviridae. However, the buoyant density in CsCl of TT virus (1.31–1.34 $g/cm^3$) and its particle size determined by filtration (30–50 nm) are not like other parvoviruses (1.39–1.42 $g/cm^3$ and 18–22 nm). Most notably, the TT virus genome was found to be circular, not linear as previously reported (Okamoto et al., *Hepatol. Res.* 10:1–16 (1998)). This was demonstrated using inverse PCR and primers located at the termini of anchored PCR products located up- and downstream of the original N22 sequence to generate an amplicon of about 1300 bp (FIG. 2). Had the genome been linear, no amplicon would have been produced. Furthermore, inverse PCR using primers derived from the N22 region were able to produce a 3700 bp product encompassing nearly the entire genome, including those sequences originally believed to be at the 5' and 3' termini. Similar products have been generated from several other TTV positive samples (data not shown). The genome sequence of this TTV isolate, designated GH1 (SEQ ID NO. 29), was found to be 3852 nucleotides in length, 113 nucleotides longer than previously reported (Okamoto et al., *Hepatol. Res.* 10:1–16 (1998)). The newly discovered region is GC rich (89%) and contains several potential stem-loop structures. Amplification of this region was possible only when contained within PCR products greater than 700 bp. These findings may explain the failure of previous attempts to demonstrate the circular nature of the genome that used inverse PCR with primers located near the presumed termini (Okamoto et al., *Hepatol. Res.* 10:1–16 (1998)).

Other than its single-stranded genome and lack of an envelope, TTV does not share any other characteristics of the Parvoviridae. TT virus does share some attributes of the Circoviridae. Members of this family include chicken anemia virus (CAV), psittacine beak and feather disease virus and porcine circovirus (PCV) (Lukert et al., *Virus Taxonomy: The Classification and Nomenclature of Viruses. The Sixth Report of the International Committee on Taxonomy of Viruses* (1995)). Circoviruses are nonenveloped, 15–22 nm in diameter, and band in CsCl at 1.33–1.37 g/ml. Their genomes comprise a single molecule of circular, single-stranded DNA 1.7–2.3 kb in length and with either positive or ambisense polarity (Lukert et al., *Virus Taxonomy: The Classification and Nomenclature of Viruses. The Sixth Report of the International Committee on Taxonomy of Viruses* (1995; Niagro et al., *Archives of Virology* 143:1723–1744 (1998)). The TT virus genome is nearly 4 kbp in length and, based upon nuclease/hybridization protection assays, appears to encapsidate the negative-strand, with respect to the ORF1 gene encoded on the complementary, or positive strand (FIG. 2). Though the particle size and circular DNA genome of TTV are larger than that reported for the Circoviridae, TT virus and circoviruses possess similar densities in CsCl, suggesting a similar protein to DNA ratio.

Nucleotide and amino acid sequence database searches failed to identify significant sequence similarity between TTV-GH1 and other viruses as has been reported previously (Okamoto et al., *Hepatol. Res.* 10:1–16 (1998)). The similarities in genome structure and composition between TTV and the Circoviridae prompted a more detailed comparison. Circoviruses contain stem-loop structures essential for DNA replication in which the loop possesses a nonanucleotide motif conserved among plant and animal circoviruses. However, CAV is an exception in that the nonanucleotide motif is semi-conserved but is not associated with a stem-loop structure (Niagro et al., *Archives of Virology* 143:1723–1744 (1998)). This motif was not identified in TT virus. In TTV, the three largest stem-loop structures identified lie outside the ORF1 and ORF2 coding regions and two of these stem-loops are located within the 113 nucleotide region cloned from TTV-GH1.

TTV encodes two large (203 and 770 amino acids, SEQ ID NOS. 30 and 31, respectively) and several small ORFs (33–105 amino acids). The circoviruses encode up to seven ORFs (Bassami et al., *Virology* 249:435–459 (1998)), including the Rep protein, involved in rolling circle replication (Niagro et al., *Archives of Virology* 143:1723–1744 (1998)). The Rep protein possesses up to four amino acid sequence motifs conserved among many plant and animal circoviruses and bacteriophage ΦX-174 (Niagro et al., *Archives of Virology* 143:1723–1744 (1998)). Conserved motifs 1 (FTL) and 3 (YXXK) were identified in ORF1 of TTV-GH1. The active site tyrosine in motif 3 was conserved in the ORF1 proteins of TTV-GH1 and TTV-TA278. Motif 4, or the P-loop (putative ATP/GTP binding motif), was not found. This motif is also absent in the putative Rep protein (encoded by ORF1) of CAV. The capsid or coat proteins of most circoviruses are encoded by separate genes and are highly basic (rich in arginine or lysine) (Niagro et al., *Archives of Virology* 143:1723–1744 (1998)). CAV is the exception, however, in that its ORF1 protein contains a highly basic amino-terminus and also possesses three of the four conserved Rep protein motifs closer to the carboxyl-end. ORF1 of TTV encodes 44 arginine residues of the first 100 amino acids and, towards the carboxyl-end of ORF1, possesses two of the four conserved Rep protein motifs. Thus, TTV ORF1 appears to resemble the CAV ORF1 protein (Niagro et al., *Archives of Virology* 143:1723–1744 (1998)) and the presence of these conserved features in TTV ORF1 suggests that TTV may replicate by a rolling circle mechanism. However, until viral transcripts and their encoded gene products are identified, the actual coding regions of TTV and their function will be difficult to determine with certainty.

From the data presented here and in Example 2 (above), it is clear that TT virus cannot be classified within an existing virus family. The circular nature of the genomic DNA, in addition to the virion size, buoyant density and lack of sequence identity preclude its membership among the Parvoviridae. However, by virtue of its negative-stranded, circular DNA genome, TT virus is most closely related to the Circoviridae, although TTV possesses a larger genome and viral particle relative to members of this family. Furthermore, the absence of significant sequence similarities between TTV and circoviruses, beyond the possible conservation of motifs involved in rolling circle replication, do not support inclusion of TTV in the Circoviridae. Therefore, it is proposed that TTV is a member of a new virus family that infects humans, tentatively named the Circinoviridae, derived from the Latin circinatio meaning 'the describing of a circle'.

Example 4

Dectection of TTV with Published Primer Sets

Serum panels from a broad spectrum of diseased and normal individuals were studied for TTV presence. These included normal volunteer donors (Southeastern Wisconsin, USA), commercial blood donors (Central and Southern USA), intravenous drug abusers (IVDA; Chicago, Ill., USA), blood donors with elevated serum alanine aminotransferase levels (Eastern USA), hemophiliacs (Netherlands), and randomly selected Japanese sera, some of which were seropositive for HTLV-I. Additionally, sera from Ghanaian children (Martinson et al., *J. of Med. Virol.* 48:278–283 (1996)) and individuals diagnosed with non-A-E hepatitis (Dawson et al., *J. of Med. Virol.* 50:97–103 (1996); Rochling et al., *Hepatoloqy* 25:478–483 (1997)) were tested.

Detection of TTV DNA Sequences by PCR

Total nucleic acids were extracted from 25 μl of serum using the DNA/RNA Extraction kit (Amersham Life Science Inc., Arlington Heights, Ill.). Nucleic acids were dissolved in 25 μl of nuclease-free water and 4 μl used as template in the amplification reactions. Oligonucleotide primers used were those described by Nishizawa (Nishizawa et al., *Biochem Biophys Res Commun* 241:92–97 (1997)) (RD037 and RD038, SEQ ID NOS. 32 and 33, respectively) followed by RD051 and RD052, SEQ ID NOS. 34 and 35, respectively) or Simmonds (Simmonds et al., *The Lancet* 352:191–194 (1998)) (SEQ ID NOS. 1 and 2 followed by SEQ ID NOS. 3 and 4), hereinafter referred to as "Set 1" or "Set 2", respectively.

Amplification reactions (20 μl) were performed for thirty-five cycles (94° C. for 20 seconds, 55° C. for 30 seconds, and 72° C. for 30 seconds) and contained 1.0 μM final concentration each primer and 1.5 units of Taq DNA polymerase (Perkin-Elmer, Foster City, Calif.). Nested PCR reactions were performed on 1.0 μl of the primary PCR reaction using the same amplification conditions as above. PCR products were analyzed by 2% agarose gel electrophoresis with visualization via ethidium bromide fluorescence. The identity of the amplified product was confirmed by Southern hybridization to sequence confirmed probe (nested or heminested PCR product).

Results

TV viremia was detected in approximately 10% of volunteer donors in the United States with or without elevated transaminase levels (Table 3), and was slightly more prevalent in commercial blood donors (13%).

TABLE 3

Prevalence of TTV in Blood Donors

| Group | No. Positive | Percent Positive |
|---|---|---|
| Volunteer Donors (High ALT) (n = 165) | 15 | 9.1% |
| Volunteer Donors (n = 150) | 16 | 10.7% |
| Commercial Donors (n = 148) | 19 | 12.8% |
| HCV NS5-only positive Donors, US (n = 41) | 2 | 4.9% |
| Japanese Individuals (n = 61) | 32 | 52.5% |

In a small panel of volunteer donors previously shown to have antibodies only to the NS5 antigen of HCV (Learyetal., *Journal of Virological Methods* 56:119–121 (1996)), approximately 5% were TTV DNA positive. Thus, the overall prevalence rate among US blood donors was 10.3%. These results differ from recently reported prevalence rates of 1.9% (19 of 1000) and 1% (1 of 100) in normal blood donors from the UK and the U.S., respectively (Charlton et al., *Hepatology* 28:839–842 (1998; Simmonds et al., *The Lancet* 352:191–194 (1998)). However, Nauomov et al., (Naoumov et al., *The Lancet* 352:195–197 (1998)) reported a rate of 10% (3 of 30) in UK normal blood donors. Each of these studies utilized different nucleic acid extraction methods as well as PCR conditions and primers. In addition, Southern hybridization was not performed to possibly identify positive samples not visualized via ethidium bromide fluorescence; thus, the true prevalence may have been underestimated. Although each sample in the current study was tested with two distinct primer sets, not all positive samples were identified by primer set 2 (Table 4).

TABLE 4

Number of samples testing positive for TTV DNA: Comparison of two PCR primer sets

| Group | Set 1 Only | Set 2 Only | Both Sets | Total |
|---|---|---|---|---|
| Volunteer Donors (High ALT) (n = 165) | 6 | 7 | 2 | 15 |
| Volunteer Donors (n = 150) | 3 | 9 | 4 | 16 |
| Commercial Donors (n = 148) | 1 | 13 | 5 | 19 |
| IVDA (n = 87) | 0 | 7 | 8 | 15 |
| Hemophiliacs (n = 169) | 1 | 80 | 14 | 95 |
| TOTAL | 11 | 116 | 33 | 160 |

Set 2 detected more samples within each group, but primer set 1 detected additional samples that were negative with set 2 primers. Set 1 alone underestimated the prevalence of TTV infection by 200–600%, while set 2 alone underestimated the prevalence by 1–40%. These data clearly indicate that while PCR primer set 2 possesses superior sensitivity, it does not identify all TTV DNA positive sera. This result, combined with the observation that TTV DNA sequences demonstrate as much as 40% divergence, suggests that studies utilizing the currently described primer sets may significantly underestimate the true prevalence of TTV. These results also illustrate the need to develop optimal oligonucleotide primers in order to detect all TTV variants. Full length genomic sequences from multiple variants are required for the identification of conserved regions for optimal primer design.

Sera from individuals considered to be "at risk" for acquiring parenterally transmitted viral agents were also tested. TTV DNA was found in 17% (15/87) of intravenous drug abusers in the USA and 56% (95/169) of hemophiliacs from the Netherlands (Table 5).

TABLE 5

Prevalence of TTV in At-Risk Individuals

| Group | No. Positive | Percent Positive |
|---|---|---|
| IVDAs, USA (n = 87) | 15 | 17.2% |
| Hemophiliacs, Netherlands (n = 169) | 95 | 56.2% |
| Ghana, West Africa (n = 24) | 14 | 58.3% |
| Non-A-E Hepatitis, USA (n = 48) | 1 | 2.1% |

In contrast, patients diagnosed with non-A-E hepatitis revealed very low prevalence in US patients (2.1%). The reason for the discrepancy between the TTV infection rate among blood donors (Table 3) and non-A-E hepatitis patients in the US is unclear, though it may reflect the small sample size of the non-A-E hepatitis patients. However, the high rate of infection among IVDAs and hemophiliacs indicates an association between increased infection risk and high rates of exposure to blood or blood products.

Among randomly selected Japanese sera tested, 32 of 61 (52%) were found to be TTV positive. This rate is higher than originally reported for blood donors in Japan (Okamoto et al., *Hepatol. Res.* 10:1–16 (1998)), however, this panel included some individuals who were HTLV-I positive, and thus, may be at higher risk for infection with blood-borne viruses. Among Ghanaian children ages 6–18, TTV was detected in 58of individuals tested (Table 5). This group has very low rates of parenteral exposure, no history of tattooing, ear piercing, or needle sharing during vaccination, and are not sexually active. This population exhibited an overall seroprevalence rate of 61% for at least one marker of HBV infection, 16% for HBsAg, 5.4% for HCV (Martinson et al., *J. of Med. Virol.* 48:278–283 (1996)), and 15% GBV-C RNA (Dawson et al., *J. of Med. Virol.* 50:97–103 (1996)). The relatively high rate of TTV infection in Ghana, compared to that of HCV or GBV-C, may indicate that TTV is more virulent upon parenteral exposure (similar to HBV) or that TTV is also transmitted by other means.

The occurrence of GBV-C and TTV coinfection in commercial blood donors and intravenous drug abusers (IVDAs) is quite low at 0.7–3.6%, despite nearly equivalent infection rates for the two viruses in these populations, i.e. 13–18% (Table 6).

TABLE 6

TTV and GBV-C coinfection rates in various populations.

|  | TTV DNA+ | GBV-C RNA+ | GBVC+ and TTV+ |
|---|---|---|---|
| Volunteer Donors (n = 99) | 14 (14%) | 2 (2.0%) | 1 (1.0%) |
| Commercial Donors (n = 148) | 19 (13%) | 22 (15%) | 1 (0.7%) |
| IVDA (n = 84) | 15 (18%) | 12 (14%) | 3 (3.6%) |

This suggests that GBV-C and TTV infection may occur via different transmission routes. While GBV-C has been shown to be exclusively transmitted parenterally (Dawson et al., *J. of Med. Virol.* 50:97–103 (1996)), it is possible that TTV infection occurs through exposure to infected blood or blood products and may also be community acquired, i.e. transmitted via the fecal-oral route. This mode of transmission could explain the relatively high prevalence of TTV infection in Japan ((Okamoto et al., *Hepatol. Res.* 10:1–16 (1998)), and this study), the US and Ghana (Tables 3 and 5). Indeed, TTV viremia in underdeveloped nations has been shown to be 7–74w in the indigenous rural people of Nigeria, Gambia, Brazil, and Ecuador (Prescott and Simmonds, *New England Journal of Medicine* 339:777 (1998)) and a recent study has demonstrated the presence of TTV DNA in human fecal material (Okamoto et al., *J. of Med. Virol.* 56:128–132 (1998)). Thus, the very high incidence of TTV infection in developing regions may be due to poor sanitary conditions resulting in the fecal-oral transmission of the agent.

The causal role of TTV in hepatitis is questionable given the low prevalence among non-A-E hepatitis patients and the relatively high rate in volunteer donors with or without elevated transaminase levels. The association between TTV infection and post-transfusion hepatitis indicated by Nishizawa et al (Nishizawa et al., *Biochem Biophys Res Commun* 241:92–97 (1997)) was concluded from the presence of TTV viremia in 3 of 5 selected patients who exhibited elevated transaminase levels following transfusion. It should be noted that these patients did not have clinically apparent hepatitis and that TTV was found in two of three patients diagnosed with carcinoma of the esophagus or gall bladder. Thus, while current studies of populations from developed countries (i.e. US, UK, and Japan) have demonstrated that TTV prevalence is higher in individuals at risk for acquiring parenterally transmitted diseases (Charlton et al., *Hepatology* 28:839–842 (1998); Okamoto et al., *Hepatol. Res.* 10:1–16 (1998); Simmonds et al., *The Lancet* 352:191–194 (1998)), its association with disease, especially post-transfusion hepatitis, is questionable.

Based upon the data presented, it is apparent that the primers currently in use do not detect all viremic samples and, as a result, underestimate the true prevalence of TT virus infection. The cloning and sequencing of TTV genomes from around the world will allow the identification of conserved regions from which universal PCR primers can be designed as has been done for HCV (Bukh et al., *Proc. Natl. Acad. Sci. USA* 89:187–191 (1992)) and GBV-C (Leary et al., *J. of Virol. Methods* 56:119–121 (1996); Muerhoff et al., *J. of Virol. Methods* 62:55–62 (1996)). Such studies will further our understanding of the genomic organization of the virus and lead to the elucidation of its encoded proteins. The identification of immunogenic proteins is necessary for the development of serologic screening assays for TTV detection, thereby providing another tool for examination of the natural history of TTV infection, its epidemiology and disease association, if any.

Example 5

Phyloqenetic Analysis of TTV Sequences

To determine the degree of sequence variability of TTV we examined a 260 bp region of the genome (not including primer sequences used during PCR) amplified from 151 globally distributed individuals. PCR products were generated using primers described in Example 1 by a hemi-nested PCR method: primers A5430 and A5427m (SEQ ID NOS. 1 and 2) were used for first round amplification followed by A8761 and A5427m (SEQ ID NOS. 3 and 2) for second round amplification, using the cycling method described in Example 4 (above). Products were separated by agarose gel electrophoresis and gel purified using the Qiaex II Gel Extraction Kit (Qiagen, Chatsworth, Calif.). Purified products were sequenced directly. Those products which yielded uninterpretable sequence (significant degree of ambiguities) were cloned into pGEM-T EASY (Promega, Madison, Wis.) and at least six clones of each PCR product were sequenced.

The TTV sequences determined in this study and those deposited in GenBank that overlapped the amplified region were aligned using the program PILEUP (Wisconsin Package, version 9.0). PCR primer sequences were not included in the sequence alignment. The final alignment of 163 sequences (260 nucleotides in length) was utilized to determine the evolutionary relationship between isolates by using the programs of the PHYLIP package, version 3.5c (Felsenstein, (1993)). Nucleotide sequence distances were determined using DNADIST. Amino acid sequence distances were determined using PROTDIST; calculated distances were then used by NEIGHBOR to generate unrooted trees. The program RETREE with the midpoint rooting option was used to plot the trees. Bootstrap values were determined on 100 resamplings of amino acid sequences and 1000 resamplings of nucleotide sequences using SEQBOOT, DNADIST for nucleotide sequences or PROTDIST for amino acid sequences, NEIGHBOR, and finally CONSENSE to generate the majority rule consensus tree. Bootstrap values greater than 70% were considered supportive of the observed groupings. The final trees were visualized with TREEVIEW (Page, *Computer Applications in the Biosciences* 12:357 (1996)).

Figure 3:
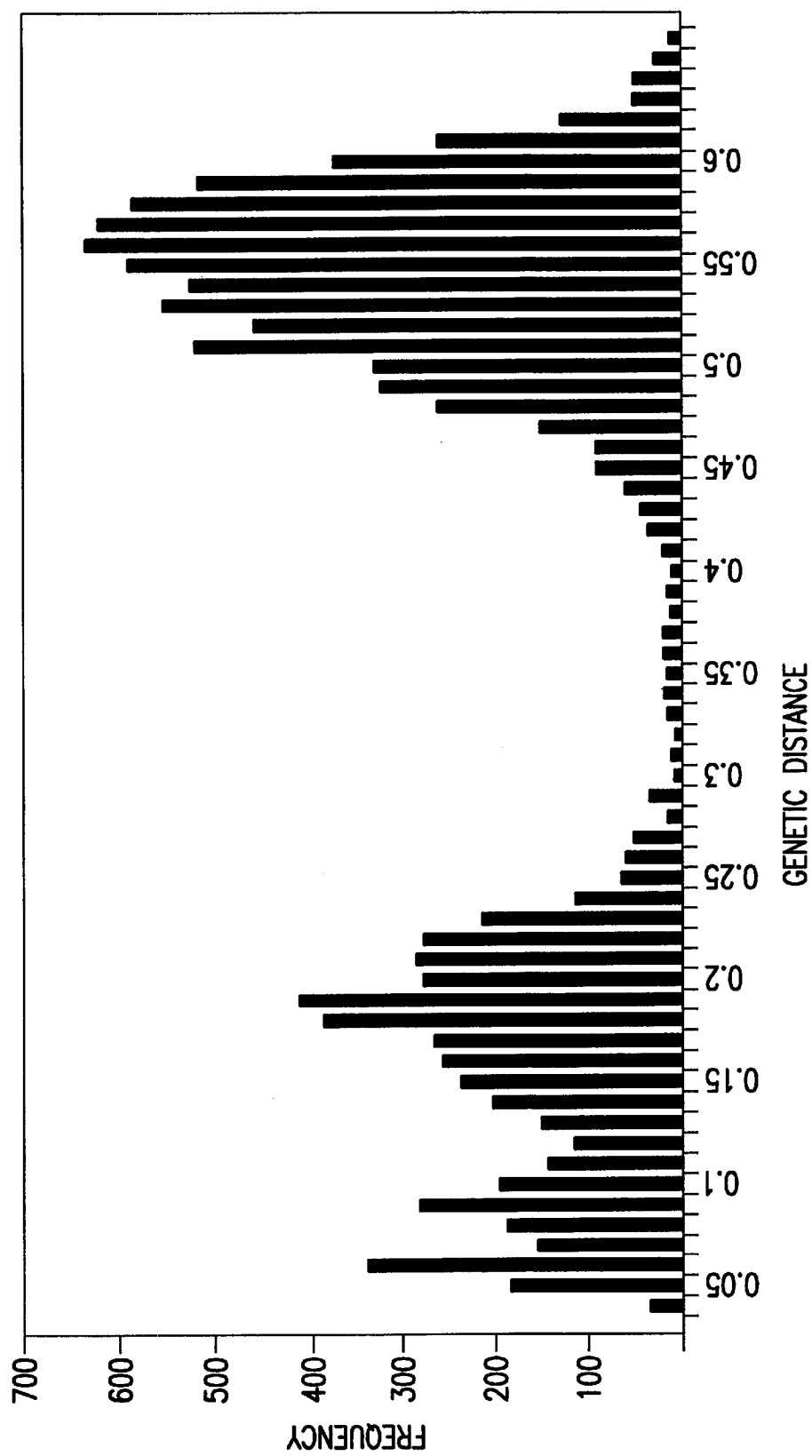
FIG. 3 shows the distribution of the pairwise genetic distances observed between 157 TTV nucleotide sequences.
Figure 4A:
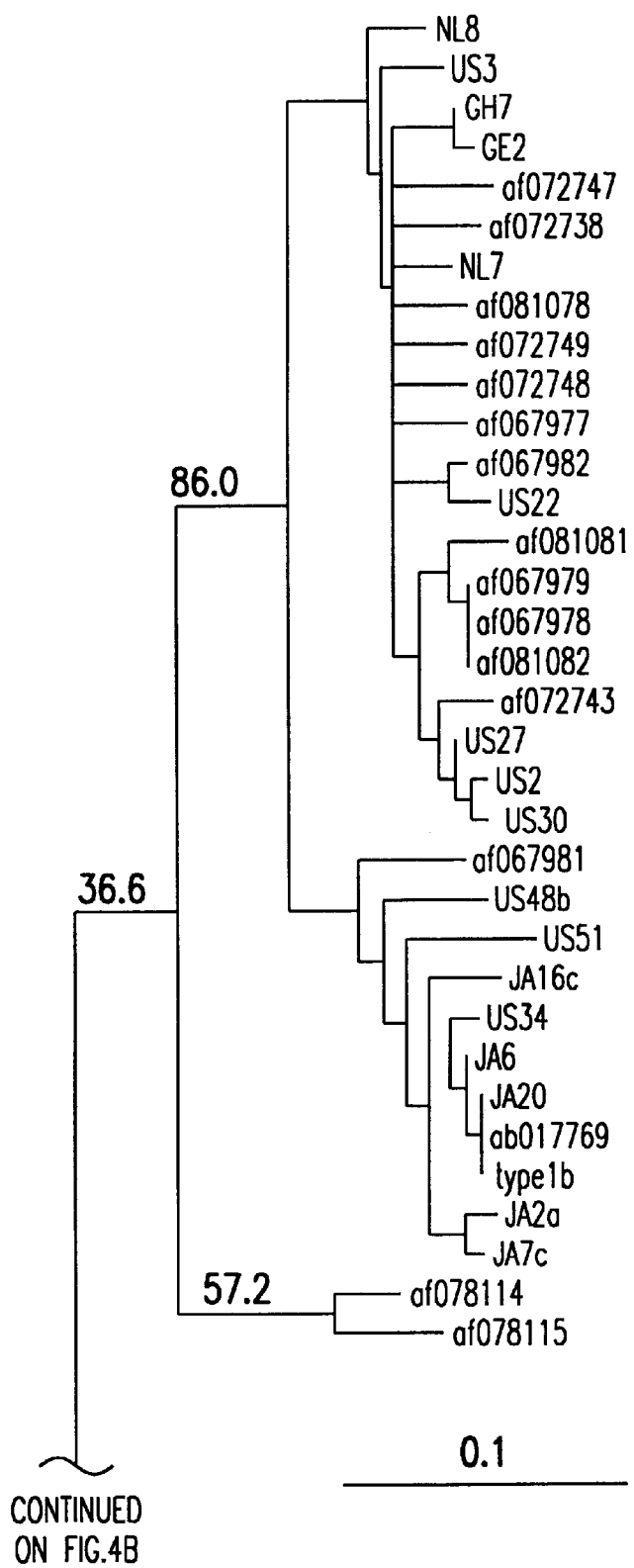
FIG. 4 shows a consensus phylogenetic tree (unrooted) of 260 nucleotides from 163 TTV isolates where genetic groups are indicated as genotypes 1, 2, and 3 and subtypes 2.1 and 2.2; sequences isolated from a single individual are designated with the isolate number followed by the lower case letters a, b, or c; and geographical designations (AR, Argentina; EG, Egypt; GE, Greece; GH, Ghana; JA, Japan; NL, Netherlands; NZ, New Zealand; US, United States), and bootstrap values at the nodes for 1000 resamplings of the data are displayed.
Figure 4B:
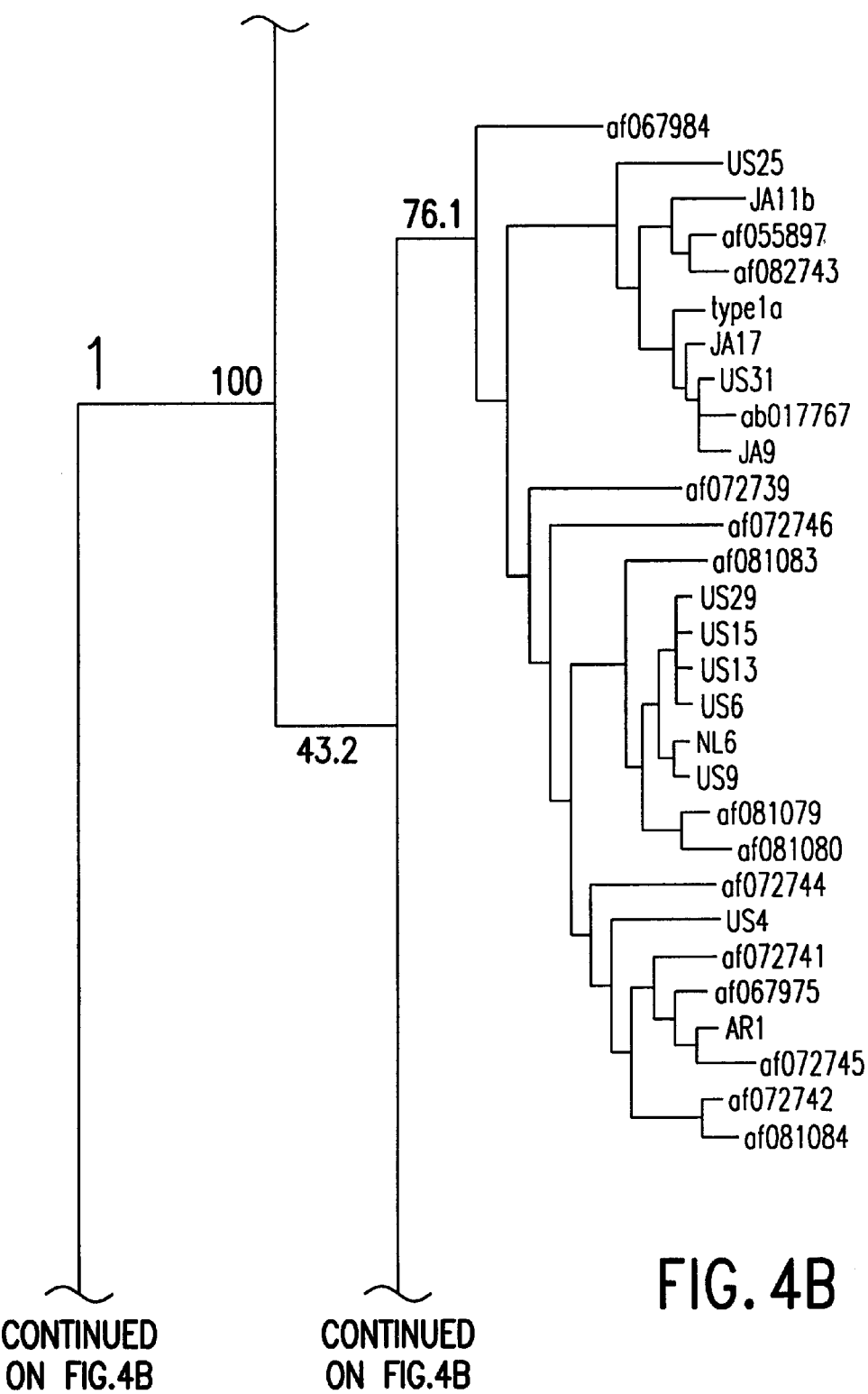
Figure 4C:
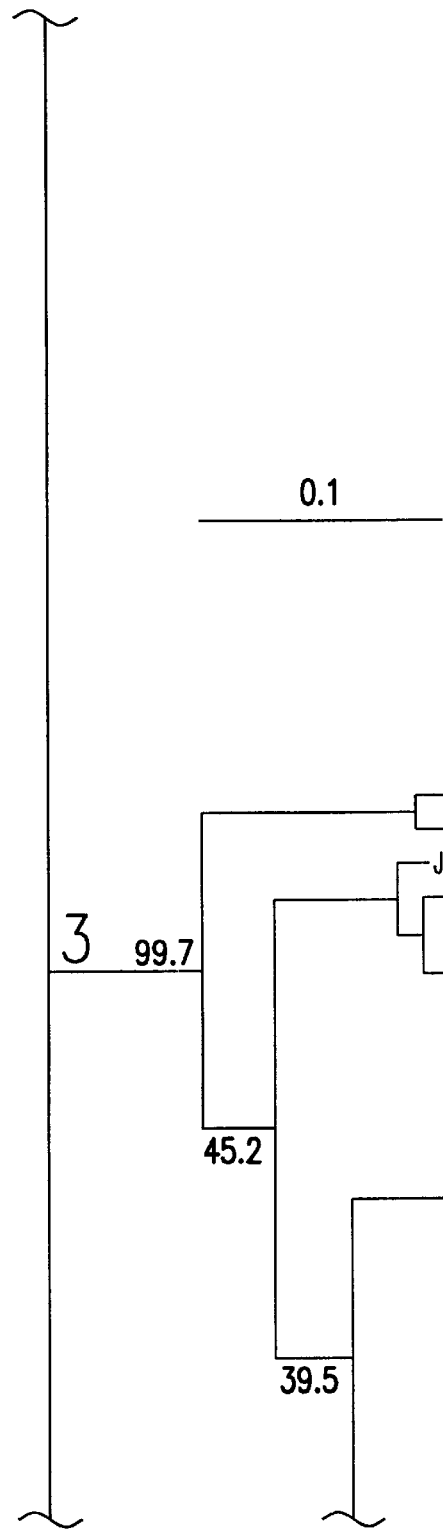
Figure 4C:
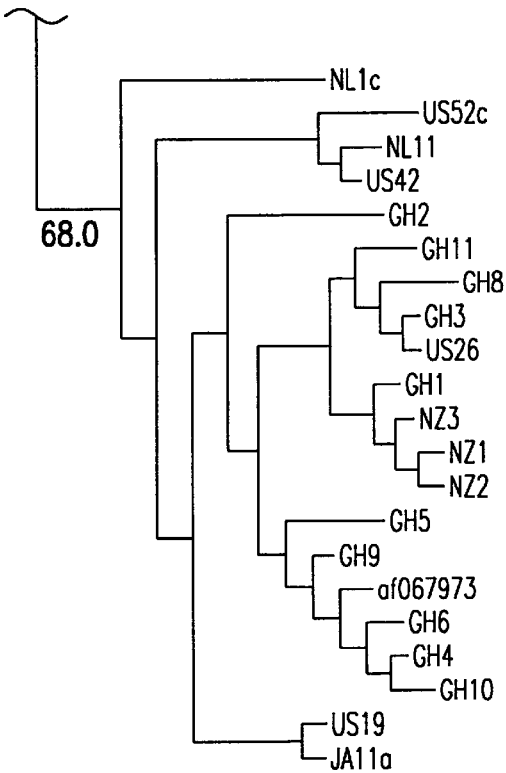
Figure 4D:
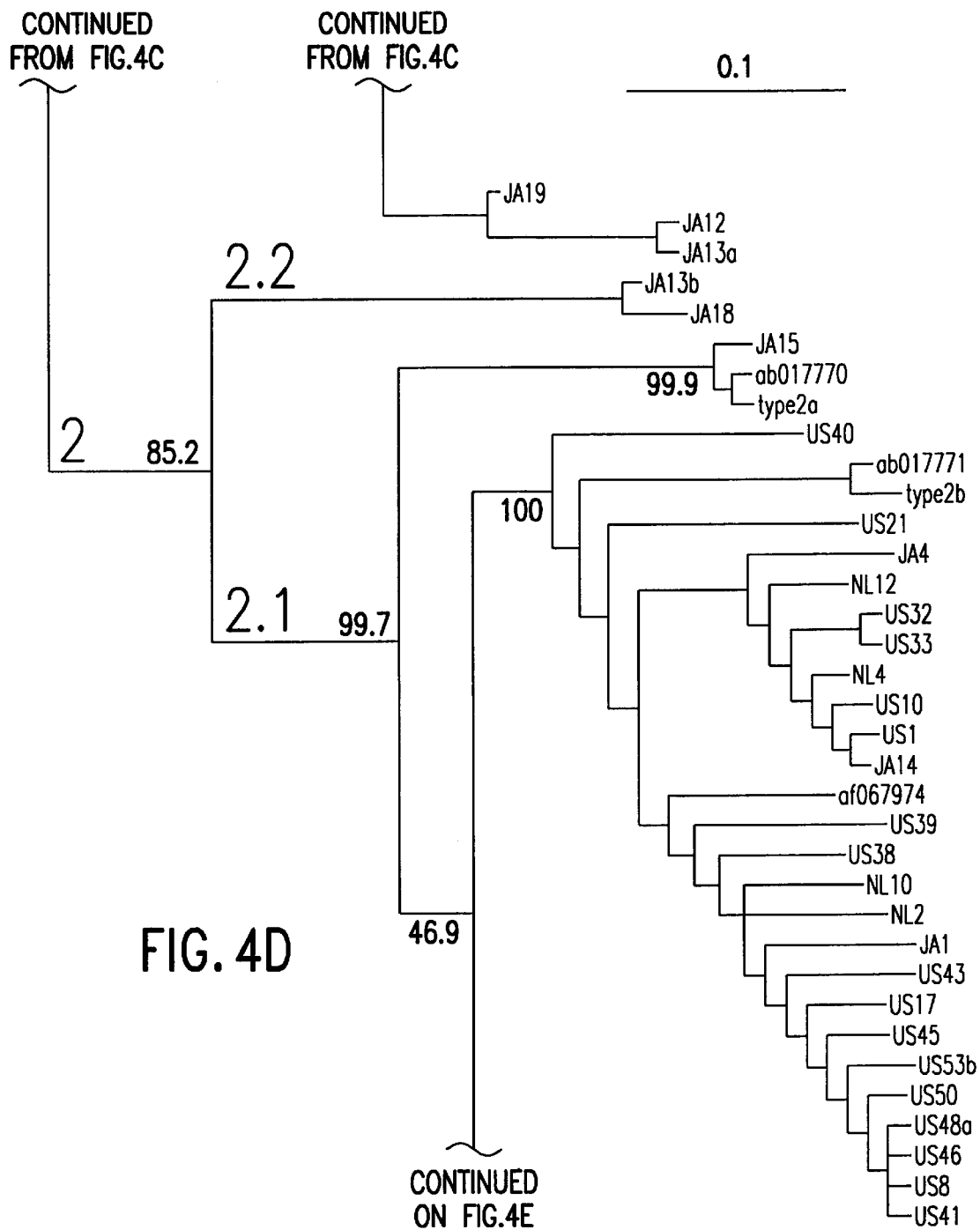
Figure 4E:
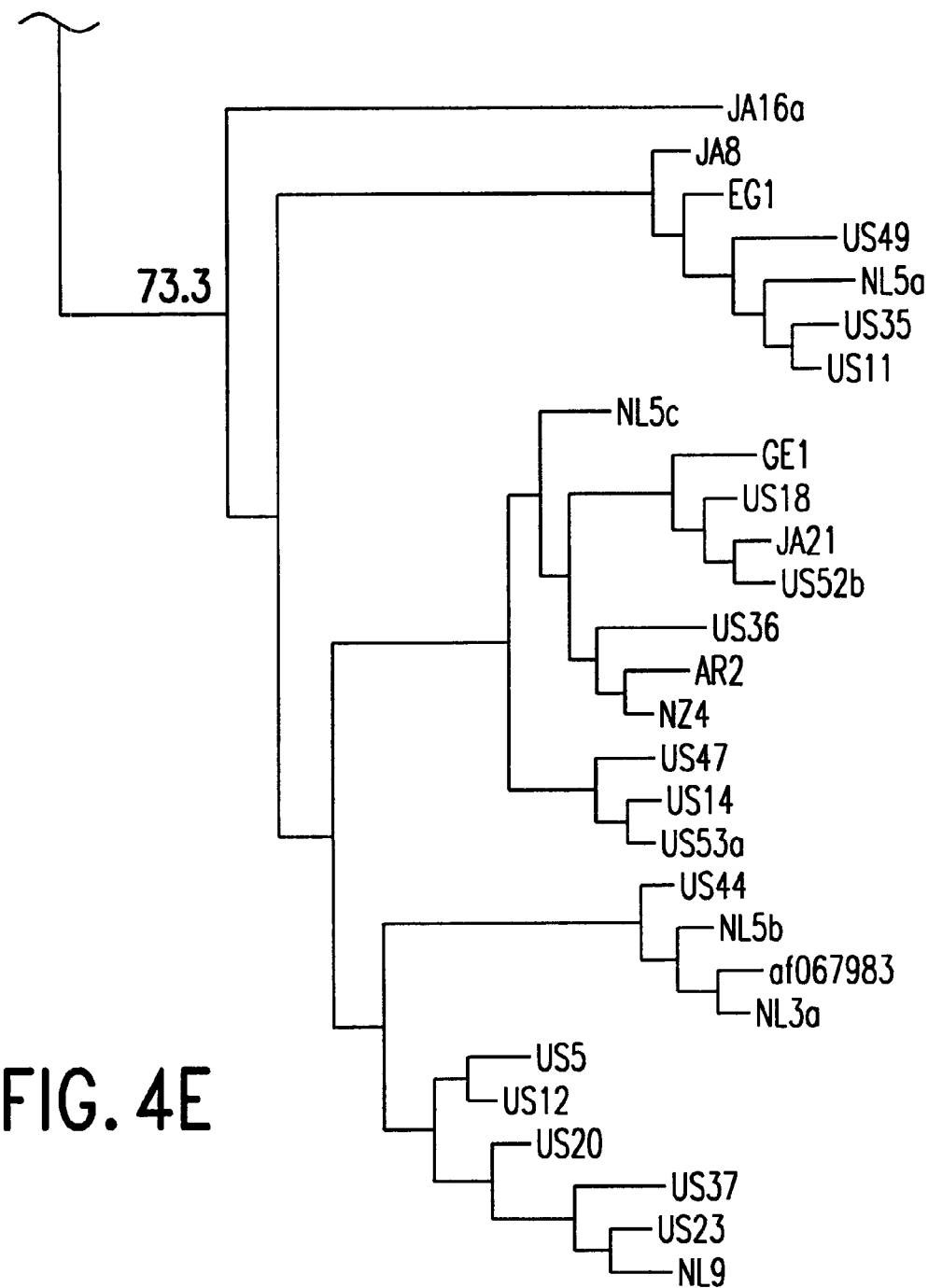

Of the 151 PCR products sequenced, 54 yielded over 10% nucleotide sequence ambiguities, suggesting the presence of mixed infections. This was confirmed by cloning and sequencing of 12 of 54 products which revealed up to 36% DNA sequence variability between sequences cloned from a single individual. The sequences we determined were aligned with 36 TTV sequences obtained from GenBank, including representatives of the putative genotypes (1a, 1b, 2a, 2b) previously characterized (Okamoto et al., *Hepatol. Res.* 10:1–16 (1998); Simmonds et al., *The Lancet* 352:191–194 (1998)). The pairwise genetic distances calculated for all 163 aligned sequences clearly shows two tiers of sequence diversity (FIG. 3), suggesting the existence of distinct genetic groups or genotypes. There was a high degree of variability, up to 0.62 substitutions per position, (or an uncorrected distance of 44) within this putative coding region of the virus. In general, pairwise distances lower than 0.26 represent intragroup distances and values higher than 0.34 represent intergroup distances.

These pairwise distances were used to generate an unrooted phylogenetic tree (FIG. 4). Three major groups were observed with approximately equally divergence from each other. These major groups were strongly supported by bootstrap analysis: groups 1 or 3 sequences associated in 100% of the trees while group 2 sequences grouped in 85% of the trees. Although subgroups 1a and 1b have been described previously (Okamoto et al., *Hepatol. Res.* 10:1–16 (1998; Simmonds et al., *The Lancet* 352:191–194 (1998)), and the branching order of group 1 sequences suggests the presence of two subgroups, the associated bootstrap values are less than 44%. Thus, we found no support for group 1 subtypes. Based upon pairwise distances, the two sequences constituting subtype 2.2 (FIG. 4), both from Japan, are more closely related to subtype 2.1 isolates than those in groups 1 or 3 (table 7); and thus have been segregated into a group 2 subtype rather into their own major group.

TABLE 7

| | Amino acid sequence distances | | | DNA Distances | |
|---|---|---|---|---|---|
| | | 1 | 2.1 | 2.2 | 3 |
| 1 | 0–0.18 | | 0–0.18 | 0.41–0.62 | 0.42–0.52 | 0.39–0.55 |
| 2.1 | 0.46–0.61 | 0–0.17 | | 0–0.23 | 0.26–0.36 | 0.34–0.54 |
| 2.2 | 0.35–0.48 | 0.16–0.25 | 0.06 | | 0.03 | 0.36–0.47 |

TABLE 7-continued

Phylogenetic Distances

| | Amino acid sequence distances | | | DNA Distances | |
|---|---|---|---|---|---|
| | | 1 | 2.1 | 2.2 | 3 |
| 3 | 0.43–0.63 | 0.33–0.52 | 0.34–0.41 | 0–0.22 | | 0.02–0.26 |
| | 1 | 2 | 2' | 3 | | |

There is strong bootstrap support for the existence of these subgroups within group 2, each with at least 85% support. Subtypes 2.1 and 2.2 do not correspond with the previously purported 2a and 2b subgroups (Okamoto et al., *Hepatol. Res.* 10:1–16 (1998); Simmonds et al., *The Lancet* 352:191–194 (1998)), the latter of which, based upon bootstrap analysis, did not segregate. Support for subgroups among genotype 3 sequences was not obtained. In addition, each of the three groups contained isolates from around the world, demonstrating no clear correlation between genotype and country of origin.

Given the high degree of nucleotide sequence variability within the TTV genome region analyzed, and inability to obtain bootstrap support for subtypes, it is possible that the true phylogenetic relationships are obscured by a high rate of synonymous substitutions. To examine this possibility, phylogenetic analysis was performed on the deduced amino acid sequences of the TTV isolates. The segregation of amino acid sequences into three major groups was supported in 96% of the trees by bootstrap analysis (data not shown). As with nucleotide sequence analysis, there was no significant bootstrap support for group 1 or 3 subtypes, although support was obtained for two group 2 subtypes in 89of the trees. As shown for the nucleotide sequences, pairwise amino acid sequence indicate that the two subtype 2.2 sequences are more closely related to subtype 2.1 isolates than those in groups 1 or 3 (table 7).

Phylogenetic analysis with bootstrapping provided strong support for the existence of three major groups of TTV sequences exhibiting approximately equal divergence. Others have suggested the presence of TTV subtypes (Okamoto et al., *Hepatol. Res.* 10:1–16 (1998); Simmonds et al., *The Lancet* 352:191–194 (1998)), but we did not obtain bootstrap support for segregation of the previously reported 1a and 1b sequences, or any of the other group 1 sequences we determined, into subgroups. This was also true for the purported 2a and 2b genotypes. Attempts to eliminate the potential obfuscation of subtypes due to the high rate of synonymous substitutions through analysis of only first and second codon positions or deduced amino acid sequences were not successful in obtaining support for subtypes. It remains possible, however, that the region analyzed is insufficient for subtype identification due to its short length (260 nucleotides) and/or high variability. Verification of our results will require the analysis of longer genomic segment, or ideally, full-length genome sequences.

Sequence analysis performed on 30 cloned TTV sequences from 12 individuals demonstrated that ten individuals were infected with two different TTV genotypes and two individuals were infected with representatives of all three genotypes (FIG. 4). These mixed infections occurred in individuals at high risk for infection with parenterally transmitted viruses, such as intravenous drug users, hemophiliacs, and nonA-E hepatitis patients. In contrast, only 1 of 36 TTV positive US donors was coinfected. It remains to be determined whether this observation is due to repeated infection with variant genotypes, rapid mutation of the virus within the individual, or some other mechanism.

TTV-GH1 and TA278 are 93% identical across the entire genome, but local regions of lower or higher identity exist. These two isolates exhibit 92% identity within the 260 base region analyzed for phylogenetic relationships. Genetic divergence in this region among the globally distributed isolates examined was up to 44% at the nucleotide level and 36% at the amino acid level. This degree of variability among geographically remote isolates has not been previously observed for circoviruses. Comparison of the four CAV genome sequences present in GenBank revealed 4% maximum diversity. Analysis of eleven CAV VP1 sequences from GenBank revealed only 1.5% sequence divergence (data not shown). Similar results are obtained upon comparison of PCV sequences (Meehan et al., *J. Gen. Virol.* 79:2171–2179 (1998)). A recent report described a hypervariable region within ORF1 of CAV spanning 13 amino acids (up to 38% divergence) based upon comparison of eight isolates (Renshaw et al., *J. of Virol.* 70:8872–8878 (1996)). In contrast, the ORF1 proteins of TTV-GH1 and TA278 exhibit 5% divergence but also contain a hypervariable region spanning 126 amino acids with 31% divergence. Thus, TTV exhibits much greater variability than CAV or PCV.

Example 6

Analysis of several full length TTV genomes

Hundreds of TT virus isolates have been identified using PCR assays which amplify less than 400 nucleotides of sequence, though only one full length (isolate GH1, 3852 nucleotides, SEQ ID NO. 29) and two near full length (isolates TA278 and TTVCHN1, 3739 nucleotides, GenBank accession nos. AB008394 and AF079173, respectively) sequences have been reported. These three sequences all represent a single and subtype of the virus (1a). To more fully understand the TT virus genome, several divergent isolates have been extended to full or near full length. These sequences reveal up to 30% nucleotide divergence, three conserved ORFs, a lack of identifiable regulatory elements, and the presence of distinct genotypes and subtypes.

Example 6.1

Genome Extensions

Previously, the present inventors described the isolation of a 260 nucleotide region from 151 globally distributed TT isolates and demonstrated the existence of at least three major virus genotypes (see Example 5). Several of the most divergent sequences from this group have been extended to genome or near genome length (Table 8).

TABLE 8

Full or near full length TTV genomes.

| Designation | SEQ ID No./ GenBank Accession No. | GENOTYPE | Genome length | ORF1 | ORF2 | ORF3 |
|---|---|---|---|---|---|---|
| GH1 | 29 | 1a | 3852 | 770 | 150 | 57 |
| JA9 | 52 | 1a | 3852 | 770 | 150 | 57 |
| JA20 | 53 | 1b | 3853 | 769 | 150 | 57 |
| JA1 | 54 | 2 | 3839 | 767 | 149 | 57 |
| JA4 | 55 | 2 | 3840 | 767 | 149 | 57 |
| US32 | 56 | 2 | 3839 | 228/530 | 149 | 57 |
| US35 | 57 | 2 | 3839 | 767 | 149 | 57 |
| JA2B | 58 | 3 | 3537* | 765 | 151 | 57 |
| JA10 | 59 | 3 | 3539* | 765 | 151 | 57 |
| TA278 | AB008394 | 1a | 3739* | 770 | 150 | 57 |
| TTVCHN1 | AF079173 | 1a | 3739* | 770 | 150 | 57 |

Isolate specific nested pairs of upstream antisense and downstream sense primers were utilized in an inverted PCR assay that exploited the circular nature of the viral genome (FIG. 2). Briefly, total nucleic acids were extracted from 25 μl of serum using the RNA/DNA Isolation Kit (Amersham Life Science Inc., Arlington Heights, Ill.) as directed by the manufacturer. Nucleic acid pellets were resuspended in 25 μl water. First round PCR reactions (20 μl volume) utilized isolate specific primers (see table 9), 4 l of total nucleic acids and Takara LA Taq (PanVera Corporation, Madison, Wis.) as specified by the manufacturer.

TABLE 9

Primers used for the construction of full length TTV genomes

| | | First Round | | Second Round | |
|---|---|---|---|---|---|
| Genotype | Isolates | Sense | Antisense | Sense | Antisense |
| 1a | GH1, JA9 | SEQ ID NO. 36 | SEQ ID NO. 37 | SEQ ID NO. 38 | SEQ ID NO. 39 |
| 1b | JA20 | SEQ ID NO. 36 | SEQ ID NO. 40 | SEQ ID NO. 38 | SEQ ID NO. 39 |
| 2b | JA1, JA4, US32 | SEQ ID NO. 41 | SEQ ID NO. 42 | SEQ ID NO. 43 | SEQ ID NO. 44 |
| 2c | US35 | SEQ ID NO. 45 | SEQ ID NO. 42 | SEQ ID NO. 46 | SEQ ID NO. 47 |

Nested PCR reactions (100 μl) were also used to isolate specific primers, Takara LA Taq and 5 μl of the first round PCR product as template. Near full length genomes were obtained for several additional isolates using a combination of specific and consensus primers to extend 5' and 3' of the 260 base region (FIG. 2 and Table 10).

TABLE 10

Primers used for the construction of partial TTV genomes

| Genotype | Isolates | Upstream product | | | Downstream product | | |
|---|---|---|---|---|---|---|---|
| | | sense | antisense1 | antisense2 | sense 1 | sense 2 | antisense |
| 3 | JA2B, JA10 | SEQ ID NO. 60 | SEQ ID NO. 48 | SEQ ID NO. 49 | SEQ ID NO. 50 | SEQ ID NO. 51 | SEQ ID NO. 69 |

Amplification products were separated by electrophoresis through a 0.8% agarose gel, then excised and purified with Geneclean II (Bio101, Vista, Calif.). Purified products were ligated into pGEM-T Easy (Promega, Madison, Wis.) and each strand was sequenced with ABI Big Dye and analyzed on the Applied Biosystems model 377 DNA sequencer.

Analysis of the full-length genomic sequences revealed that the TT virus genome ranged from 3839 to 3853 nucleotides in length. We were unable to generate full-length genotype 3 sequences. Therefore, the partial genomic sequences of 3537 to 3539 nucleotides in length were generated. These sequences started at position 94 of the full length TT virus sequence (SEQ ID NO. 29) and ending approximately 210 bases short of the full-length sequences. BLAST searches of the GenBank database utilizing these nine distinct isolates did not reveal significant similarities to any other known sequence.

Example 6.2

Nucleotide Analysis

Nucleotide sequence comparisons were performed as described in Examples 3 and 5. The seven full-length TTV genomes were between 73.8% and 96.5% identical to one another (Table 11).

TABLE 11

Pair wise comparison of amino acid sequences of ORF1, ORF2t, and ORF3 and the nucleotide sequences of the full and near full length genomes.

| | SUZ11 | AB008394* | AF079173* | A1-16 | SUZ36 | WD77 | HTLV11 | HTLV21 | TTVsA4 | HTLV12 | Suz12 |
|---|---|---|---|---|---|---|---|---|---|---|---|
| | | | | | Genome per cent identity | | | | | | |
| SUZ11-ORF1 | | 97.7 | 95.7 | 92.6 | 84.1 | 73.9 | 73.9 | 73.8 | 74.0 | 73.1 | 72.5 |
| ORF2t | | | | | | | | | | | |
| ORF3 | | | | | | | | | | | |
| AB008394*-ORF1 | 93.4 | | 96.5 | 93.0 | 84.3 | 73.4 | 73.4 | 73.4 | 73.4 | 73.4 | 72.7 |
| ORF2t | 96.7 | | | | | | | | | | |
| ORf3 | 100.0 | | | | | | | | | | |
| AF079173*-ORF1 | 92.9 | 94.0 | | 92.1 | 84.3 | 73.1 | 72.7 | 72.8 | 73.0 | 72.8 | 72.2 |
| ORF2t | 96.7 | 96.0 | | | | | | | | | |
| ORF3 | 100.0 | 100.0 | | | | | | | | | |
| A1-16-ORF1 | 92.9 | 94.0 | 93.5 | | 85.6 | 74.1 | 74.0 | 74.1 | 74.4 | 73.6 | 73.3 |
| ORF2t | 96.0 | 96.0 | 94.7 | | | | | | | | |
| ORF3 | 94.8 | 94.8 | 94.8 | | | | | | | | |
| SUZ36-ORF1 | 86.2 | 87.4 | 86.1 | 89.1 | | 74.2 | 74.0 | 74.2 | 74.1 | 74.1 | 73.0 |
| ORF2t | 77.5 | 76.8 | 75.5 | 78.1 | | | | | | | |
| ORF3 | 79.3 | 79.3 | 79.3 | 81.0 | | | | | | | |
| WD77-ORF1 | 67.2 | 68.4 | 66.8 | 66.5 | 68.6 | | 95.7 | 96.5 | 92.6 | 73.5 | 73.2 |
| ORF2t | 51.0 | 51.7 | 49.7 | 53.0 | 52.3 | | | | | | |
| ORF3 | 74.1 | 74.1 | 74.1 | 75.9 | 74.1 | | | | | | |
| HTLV11-ORF1 | 66.3 | 67.7 | 65.9 | 65.6 | 67.8 | 94.3 | | 95.7 | 91.7 | 73.3 | 72.9 |
| ORF2t | 51.0 | 51.7 | 49.7 | 53.7 | 51.7 | 94.0 | | | | | |
| ORF3 | 79.3 | 79.3 | 79.3 | 79.3 | 74.1 | 89.7 | | | | | |
| HTLV21-ORF1 | 66.7 | 68.1 | 66.1 | 65.9 | 67.8 | 95.4 | 93.5 | | 92.4 | 73.8 | 73.2 |
| ORF2t | 51.0 | 51.7 | 49.7 | 53.7 | 53.0 | 97.3 | 94.7 | | | | |
| ORF3 | 70.7 | 70.7 | 70.7 | 70.7 | 72.4 | 93.1 | 86.2 | | | | |
| TTVsA4-ORF1 | 66.8 | 68.5 | 67.9 | 65.1 | 68.9 | 91.5 | 90.2 | 91.7 | | 73.7 | 73.2 |
| ORF2t | 47.7 | 48.3 | 47.0 | 50.3 | 51.0 | 90.1 | 88.7 | 90.0 | | | |
| ORF3 | 72.4 | 72.4 | 72.4 | 74.1 | 72.4 | 98.3 | 87.9 | 91.4 | | | |
| HTLV12-ORF1 | 67.2 | 67.6 | 66.4 | 67.0 | 68.4 | 66.2 | 66.2 | 66.4 | 67.0 | | 95.3 |
| ORF2t | 49.3 | 50.7 | 49.3 | 52.0 | 52.0 | 53.0 | 52.5 | 53.0 | 50.3 | | |
| ORF3 | 82.8 | 82.8 | 82.8 | 84.5 | 81.0 | 77.6 | 74.1 | 75.9 | 75.9 | | |
| Suz12-ORF1 | 67.1 | 67.2 | 66.2 | 66.6 | 68.1 | 67.3 | 66.6 | 67.8 | 67.4 | 93.7 | |
| ORF2t | 48.0 | 49.3 | 48.0 | 50.7 | 51.3 | 52.3 | 51.7 | 51.7 | 49.7 | 96.7 | |
| ORF3 | 81.0 | 81.0 | 81.0 | 82.8 | 79.3 | 79.3 | 72.4 | 77.6 | 77.6 | 94.8 | |
| | | | | | Amino acid per cent identity | | | | | | |

Figure 5:
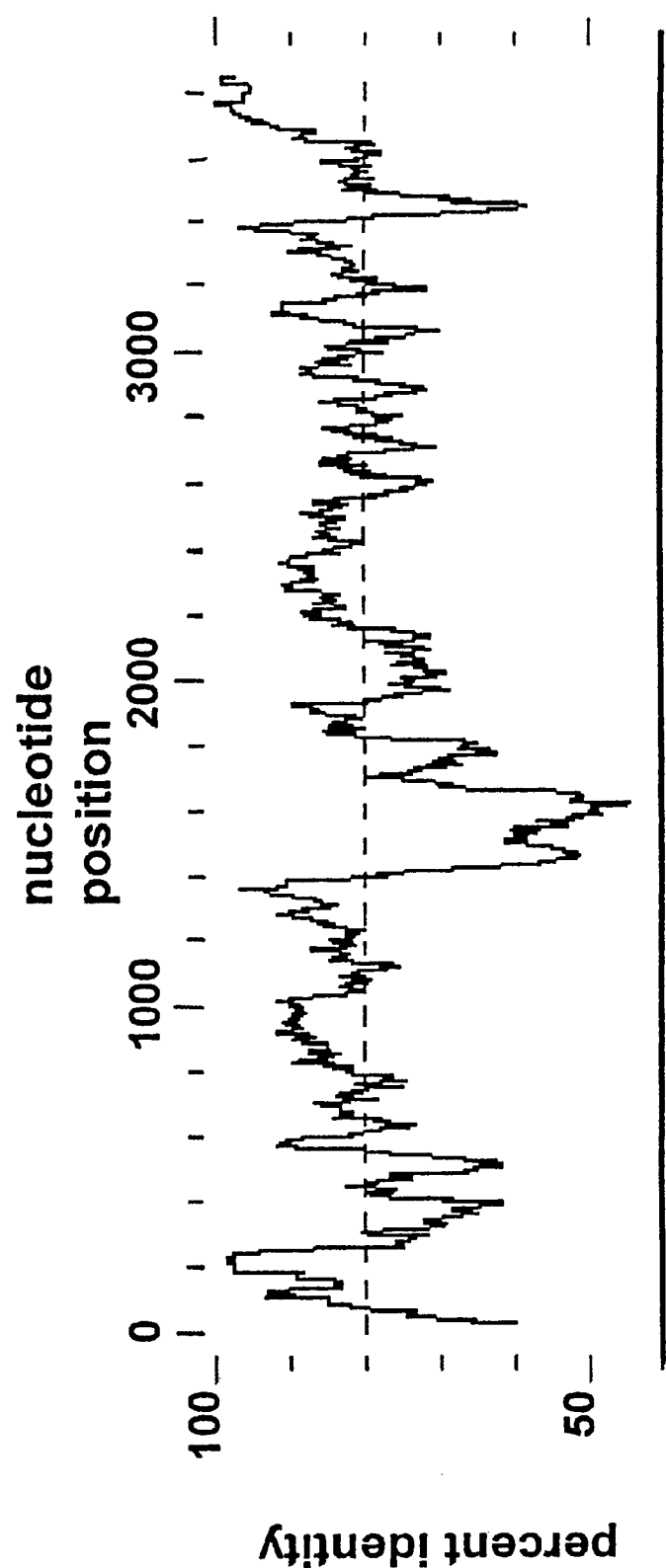
FIG. 5 shows the percent identity plotted across the alignments of seven full length TT virus nucleotide sequences within a sliding window of analysis of 50 positions where the dashed lines represent the mean identity across the entire length analyzed.

The partial genomes were 72.2% to 97.7% identical across the regions of overlap. Detailed regional comparisons performed by aligning the seven full length genomes and then plotting the percent identity within a sliding window of comparison, demonstrated approximately 80% identity across the entire length (FIG. 5). Within these genomes, multiple regions of very high similarity (>90%), as well as several regions of extreme variability (<70%), were present. Inclusion of the four partial sequences did not dramatically alter these results.

Phylogenetic analysis was performed to determine the genetic relationship of the 7 full length and 4 near-full length genome sequences. Sequences were aligned and analysis performed across the region of overlap. Genetic distances suggested the presence of four distinct groups. Isolates TA278 (GenBank accession No. AB008394), TTVCHN1 (GenBank accession No. AF079173), GH1 (SEQ ID NO. 29), and JA9 (SEQ ID NO. 52) grouped closely to one another with distances of 0.0239 to 0.0805 substitutions per position. Isolates JA1 (SEQ ID NO. 54), JA4 (SEQ ID NO. 55), US32 (SEQ ID NO. 56) and US35 (SEQ ID NO. 57) grouped together with distances of 0.0352 to 0.0950 substitutions per position, however, these sequences segregate from the previous group with distances greater than 0.3879. Isolates JA2b (SEQ ID NO. 58) and JA10 (SEQ ID NO. 59) grouped independently from the above sequences with distances greater than 0.3919 substitutions. These two isolates had a pairwise distance of 0.0491. The final isolate, JA20, formed a unique group with genetic distances between 0.1635 and 0.3941 to all other isolates.

Figure 6:
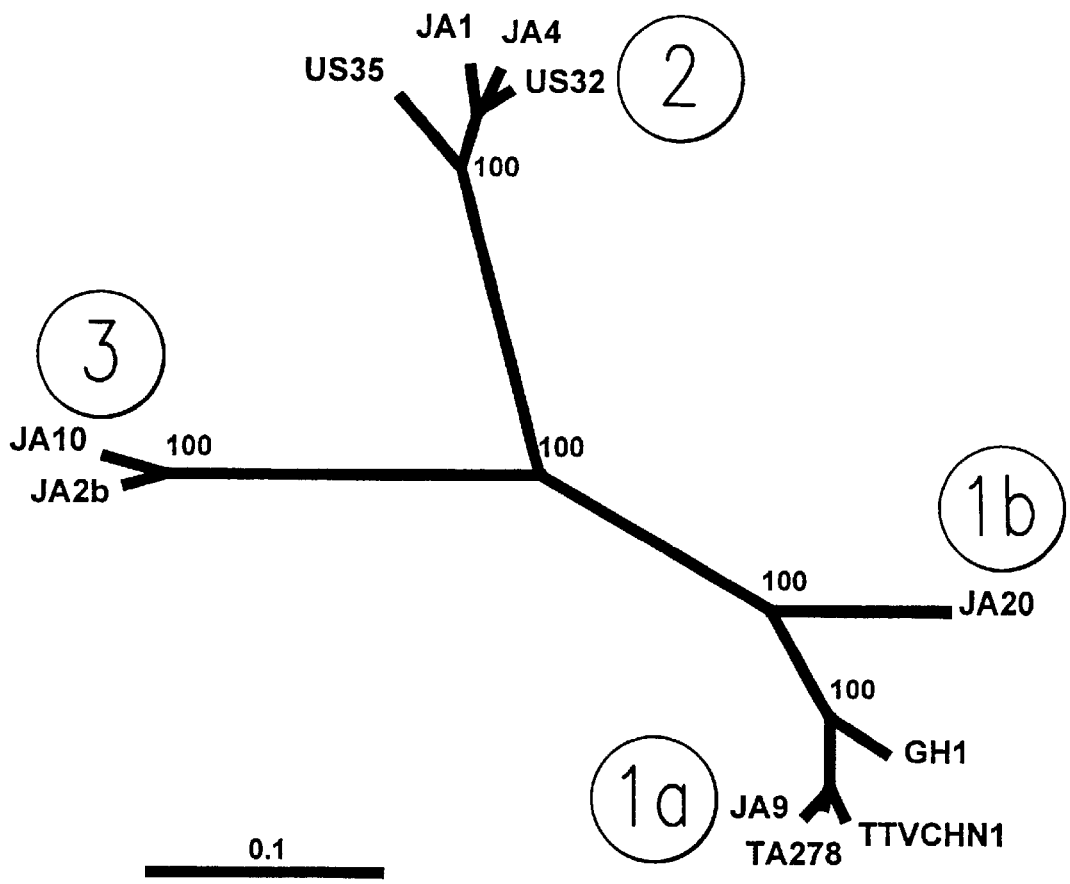
FIG. 6 shows the unrooted phylogenetic tree generated from an alignment of seven full length and four near full length TT virus nucleotide sequences where bootstrap values are shown near the appropriate nodes for 1000 resamplings of the data and genotypes 1a, 1b, 2, and 3 are indicated.

An unrooted phylogenetic tree clearly demonstrated the relationship of these sequences to one another, forming four clusters, all supported by bootstrap values greater than 89% (FIG. 6). The first of these (TA278, GenBank accession No. AB008394; TTVCHN1, GenBank accession No. AF079173; GH1, SEQ ID NO. 29; and JA9, SEQ ID NO. 52) represented isolates which have previously been characterized as genotype 1. Comparison with reported partial TT virus sequences suggested that these may be members of subtype 1a. The second cluster (JA1, SEQ ID NO. 54; JA4, SEQ ID NO. 55; US32, SEQ ID NO. 56; and US35, SEQ ID NO. 57) represented sequences of genotype 2, most similar to subtype 2b. The sequences of isolates JA2b (SEQ ID NO. 58) and JA10 (SEQ ID NO. 59) represented genotype 3 as defined in Example 5. The final isolate, JA20 (SEQ ID NO. 53), was most closely related to the genotype 1 sequences, yet grouped independently of these sequences. Comparisons to partial sequences demonstrated that this isolate represented subtype 1b. The presence of the 4 near full-length genomes did not alter these results, as the observed groupings were identical in their absence.

Example 6.3

Analysis of Open Reading Frames

The availability of multiple diverse isolates also allowed the identification of conserved ORFs. Barring the isolation of viral proteins, the presence of a highly conserved ORF lends support to the possibility of an actual viral protein being synthesized from an ORF. The large open reading frame (SEQ ID NO. 29, residues 589–2898, encoding a 770 amino acid protein, see Example 3) was conserved in all but one of 19 isolates, ranging from 765 to 770 amino acids in length (Table 8). The US32 ORF1 was interrupted by an in-frame stop codon. While it is possible that this was an artifact, analysis of multiple clones revealed identical sequence. A methionine was present immediately following the stop codon. Thus, it is possible that this isolate might produce two distinct proteins. Further experiments are necessary to address this issue. Among the full-length isolates, the amino acid sequences of ORF1 exhibited 65.1% to 95.6% identity (TABLE 11). The conserved initiating methionine codon (position 589 of GH1, SEQ ID NO. 29) resided within a Kozak motif for the efficient initiation of eucaryotic protein synthesis (Kozak, *J. of Cell. Biol.* 108:229–241 (1989)). Additionally, there was a conserved eucaryotic polyadenylation signal (AATAAA) located 177 nucleotides downstream from the ORF1 termination codon (position 2899 of GH1, SEQ ID NO. 29). This was the only polyadenylation signal conserved in all TT sequences.

The second ORF (nts 107–712 of SEQ ID NO. 29, encoding a 202 amino acids protein) was not conserved in all of the eleven TTV isolates examined. Though ORF2 was present in all genotype 1 sequences, nucleotide deletions were present in all genotype 2 and 3 sequences that resulted in a frameshift. A smaller version of ORF2 (SEQ ID NO. 29, nts 263–712, encoding a 149 to 151 amino acid protein) was conserved in all of the eleven isolates. Comparisons of this truncated ORF, ORF2t, demonstrated extreme sequence divergence, with as little as 47.0% amino acid sequence identity (Table 11). Contrary to ORF1, the conserved methionine codon did not lie within an optimal Kozak sequence (Kozak, *J. of Cell. Biol.* 108:229–241 (1989)). However, residues incompatible with eucaryotic translation initiation at this site were not found.

A third open reading frame of 57 amino acids (nucleotides 2904–3074, SEQ ID NO. 29) was found in all eleven isolates. This ORF, ORF3, was located immediately downstream of ORF1, terminating at the to conserved polyadenylation signal. Amino acid sequence comparisons demonstrated that ORF3 was greater than 70.7% conserved, the least variable of the three conserved ORFs (Table 11). There appeared to be no other ORFs longer than 30 nucleotides conserved in any of the six reading frames of all eleven full length and near full length sequences.

Example 6.4

Primer Design

As TT virus isolates have continued to be identified, researchers have attempted to design new PCR primers in an effort to improve PCR assay sensitivity. The majority of these utilize primers located within ORF1. Even though these primers have been successful at identifying multiple genotypes and subtypes of TT virus, the high degree of variability within the primer regions of ORF1 (greater than 10% divergence) may result in a large number of undetected positive samples. In fact, using first or second generation PCRs it is necessary to perform several distinct assays to estimate the prevalence of TT virus ((Simmonds et al., *The Lancet* 352:191–194 (1998)) and Example 4). Recently, a PCR assay employing primers designed within the first 200 nucleotides of the genome has demonstrated that 92% of healthy Japanese individuals are TT virus positive (Takahashi et al., *Hepatol. Res.* 12:233–239 (1998)). While these primers exhibited much greater sensitivity compared to previous sets, they are designed solely to genotype 1 isolates and will not amplify genotype 2 specific sequences (data not shown). As genotype 2 and 3 isolates are also prevalent in Japan, it is possible that additional TT virus positive individuals would be identified with consensus primers designed from alignments of sequences representing all three genotypes. Utilizing full length and partial genome alignments from this study (FIG. 5), three sets of consensus oligonucleotide primers have been designed which are able to detect genotype 1, 2, and 3 sequences. These primers and their use are described in Example 7.

Example 7

Third-generation TTV PCR Primers

TT virus prevalence determined using first and second generation primers are thought to underestimate the true prevalence of TT virus in the populations examined to date (see Example 4). Recently, oligonucleotide primers have been described by Takahashi et al. (Takahashi et al., *Hepatol. Res.* 12:233–239 (1998)) that are 10–100 times more sensitive than those described by Okamoto et al. (Okamoto et al., *Hepatol. Res.* 10:1–16 (1998)) and Simmonds et al. (Simmonds et al., *The Lancet* 352:191–194 (1998)). Although these primers will only detect genotype 1 sequences (Leary and Erker, unpublished observations), 92% of healthy individuals in Japan were positive by this assay. Here, we present three nested PCR assays capable of detecting the most divergent isolates of TT virus known. These third-generation assays have superior sensitivity to all PCR assays previously described. Additionally, we have used these assays to demonstrate that TT virus is present in the serum of a variety of distinct animal species, eliminating TT virus as an exclusively human virus and questioning its role as a causal agent in human liver disease.

Primer Design

Nucleotide sequence alignments were performed using the genome length sequences (SEQ ID NOS. 29, 52–57) from Example 6 to identify regions of conservation among the distinct isolates. Nested pairs of oligonucleotide primers were designed to three regions of the virus genome and examined for identity against partial TT virus sequences present in existing databases. Selected primers were tested by PCR for utility and sensitivity utilizing several previously identified serum samples known to be of high titer. Three sets of PCR primers were PCR primers were subjected to extensive testing: Set A forward 1 (SEQ ID NO. 60); Set A reverse 1 (SEQ ID NO. 61); Set A forward 2 (SEQ ID NO. 62); Set A reverse 2 (SEQ ID NO. 63); Set B forward 1 (SEQ ID NO. 64); Set B reverse 1 (SEQ ID NO. 65); Set B forward 2 (SEQ ID NO. 66); Set B reverse 2 (SEQ ID NO. 67); Set C forward 1 (SEQ ID NO. 68); Set C reverse 1 (SEQ ID NO. 69); Set C forward 2 (SEQ ID NO. 70); Set C reverse 2 (SEQ ID NO. 71).

PCR Assays

Total nucleic acids were extracted from 25 or 50 $\mu$l of serum using the RNA/DNA Isolation Kit (Amersham Life Science Inc., Arlington Heights, IL) as directed by the manufacturer. Dried nucleic acid pellets were then dissolved in 25 or 50 $\mu$l of water corresponding to the initial serum volume.

First round PCR reactions (10 $\mu$l volume) utilized 1.0 $\mu$M final concentration of each primer, 2 $\mu$l of total nucleic acids and the GeneAmp PCR Reagent Kit (Perkin Elmer, Foster City, Calif.) as specified by the manufacturer with a final $MgCl_2$ concentration of 2.0 mM. Nested PCR reactions (25 $\mu$l) utilized 0.5 $\mu$M final concentration of each primer, 1 $\mu$l of the first round PCR product as template and the conditions described above. Amplification was for 35 cycles (20 seconds at 940; 30 seconds at 55°C.; 30 seconds at 72° C.) followed by a 10 minute extension at 72° C. Nested PCR products were separated by electrophoresis through a 1.2% agarose gel, blotted onto a nylon membrane and analyzed by Southern hybridization to score positive results.

Phylogenetic Analysis

Nested PCR products were gel isolated, then excised and purified with Geneclean II (Bio101, Vista, Calif.). Purified products were ligated into pGEM-T Easy (Promega, Madison, Wis.) and each strand was sequenced with ABI Big Dye and analyzed on the Applied Biosystems model 377 DNA sequencer. Sequences were edited and assembled utilizing Sequencher version 3.0 (Gene Codes Corp., Ann Arbor, Mich.) and analyzed using the programs of the Wisconsin Sequence Analysis Package (Version 9.0, Genetics Computer Group, Madison, Wis.). Sequence alignments were performed utilizing the GAP program with the default settings in place for gap creation and extension. Phylogenetic distances between pairs of nucleotides were determined using DNADIST, and the distances between pairs of the amino acids were determined by the PRODIST program (Felsenstein, (1993)) of the PHYLIP package (version 3.5c). These computed distances were utilized for the construction of phylogenetic trees using the programs NEIGHBOR and RETREE. The final output was generated with the use of TREEVIEW (Page, *Computer Applications in the Biosciences* 12:357 (1996)). Bootstrap values were determined on 100 resamplings of the nucleotide or amino acids sequences, respectively, using SEQBOOT, DNADIST or PROTDIST, NEIGHBOR and CONSENSE. Values greater than 70% were considered supportive of the observed groupings.

Performance of the Third Generation PCR Assays

The present inventors compared the primer sets against previously reported PCR assays for the detection of TT virus by testing a serum panel of 48 normal donors of which approximately 25% had been previous shown to be TT virus positive by first- and second-generation TTV PCR says. As shown in Table 12, 38 (79.2%) of the samples were found to be positive by at least one of the third-generation assays and 24 (50.0%) were positive by 2 or more assays.

TABLE 12

| Sample | Nishizawa | Okamoto | Simmonds | Set A | Set B | Set C |
|---|---|---|---|---|---|---|
| 1 | | | | | | + |
| 2 | | + | | | + | |
| 3 | | | | + | + | |
| 4 | | + | + | | | |
| 5 | + | | | | + | |
| 6 | | | + | | | |
| 7 | | | | | + | + |
| 8 | | + | | | | + |
| 9 | | | | | + | + |
| 10 | | | | + | + | + |
| 11 | | | | | | + |
| 12 | | | | | | |
| 13 | | | | | + | + |
| 14 | | | | | + | |
| 15 | | | | | | + |
| 16 | | | | | | |
| 17 | | | | | | + |
| 18 | | | | | | |
| 19 | | + | + | + | + | + |
| 20 | | + | + | + | + | + |
| 21 | | | | | | |
| 22 | | | | | + | |
| 23 | | | | | | |
| 24 | | | | + | + | |
| 25 | | | | + | + | + |
| 26 | | | | | + | |
| 27 | | | | | | + |
| 28 | | | | + | + | + |
| 29 | + | | | + | + | + |
| 30 | | | | | | |
| 31 | | | | | | |
| 32 | | | | | | |
| 33 | | | | | + | |

TABLE 12-continued

| Sample | Nishizawa | Okamoto | Simmonds | Set A | Set B | Set C |
|---|---|---|---|---|---|---|
| 34 | | | | + | + | |
| 35 | | | | + | + | + |
| 36 | | + | | + | + | + |
| 37 | | | | | | |
| 38 | | | | | + | |
| 39 | | | | + | + | |
| 40 | | | | | | |
| 41 | + | | | | + | + |
| 42 | | | | | + | |
| 43 | | | | | | + |
| 44 | | | | + | + | + |
| 45 | | | + | + | + | + |
| 46 | | + | | | + | + |
| 47 | | + | + | + | + | + |
| 48 | | | | | + | |
| Total | 3 | 8 | 9 | 13 | 29 | 23 |

Set A detected 13 (27.1%) samples, Set B, 29 (60.4%) samples, and Set C, 23 (47.9%) samples. Previously described PCR assays for TT virus by Nishizawa, Okamoto and Simmonds detected 3 (6.3%), 8 (16.7%), and 9 (18.8%) samples, respectively. Though none of the samples are positive in all assays, Set B and Set C assays are clearly superior to any of the others. Set B detected 76.3% of the positive samples while Set C detected 60.5. In combination, Set B and Set C detect 36 of the 38 (94.7%) of the positive samples though only 42.1% are detected by both assays. These results are not surprising as TT virus has been previously shown to have significant divergence at the nucleic acid level, finding which can have dramatic effects on molecular based assays. In addition, it is possible to use different combinations of the primers described above. Specifically, we have used the forward primers from set A and the reverse primers form set B in nested PCR (SEQ ID NO:64 and SEQ ID NO:69, followed by SEQ ID NO:66 and SEQ ID NO:71) to detect 14 of 38 (36.8%) of the TTV-positive samples detected in table 12 (data not shown).

Because the new primer pairs described above appear to be superior to those previously reported, a number of populations previously evaluated for the presence of TT virus (Example 4) were reexamined utilizing Set B primers (Table 13).

TABLE 13

| Population | Set B Positive | Percent Positive | Previously Positive* |
|---|---|---|---|
| Volunteer Blood Donors (n = 91) | 31 | 34.1 | 10.7 |
| Volunteer Blood Donors (High ALT n = 69) | 11 | 15.9 | 9.1 |
| Commercial Blood Donors (n = 48) | 19 | 39.6 | 12.8 |
| Injectable Drug Users (n = 82) | 67 | 81.7 | 17.2 |
| Hemophiliacs (n = 73) | 70 | 95.9 | 56.2 |
| New Zealand Children (n = 36) | 8 | 22.2 | 11.1 |
| Non A-E Hepatitis Cases (n = 47) | 28 | 59.6 | 2.1 |
| Japanese Individuals (n = 20) | 20 | 100.0 | 35.0 |

*See Example 5

Among volunteer blood donors with normal ALT levels, (34.1%) were found to be positive for TT virus. This is as compared to 10.7% previously found to be positive with two distinct primer pairs. When volunteer blood donors with elevated ALT values were examined, 11 (15.9%) were positive as compared to the 9.1% determined previously for this population. Commercial blood donors that were 12.8% positive by the two primer pairs are currently 39.6% positive utilizing Set B primers. Further, injectable drug users that were 17.2% positive in the previous study were 81.7% positive with Set B primers. Finally, among 48 non A-E hepatitis samples tested, only 1 was positive utilizing the two primer pairs while 59.6% were positive in the existing assay.

Additionally, the present inventors have tested a number of other populations and have compared the results to the previous standard of the sum of two distinct primer pairs (data not shown). Hemophiliacs, which were 56.2% positive by the combination of two previous assays, were 95.9% positive with the Set B primer assay. Japanese blood donors that were previously 35.0% positive were now 100% positive, and the rate was double (22.2% as compared to 11.1%) in a panel of New Zealand children utilizing the Set B primer assay. Most remarkable in these comparisons is that virtually all samples previously determined to be TT virus positive were detected with the Set B primer assay. This was not the case in the limited study initially conducted with these primers (Table 12). Also examined were limited samples from several species of non-human primates. TT virus was detected in tamarins (23.5%), owl monkeys (20.0%) and chimpanzees (50.0%), while virus sequences were not detected in calithrix, mystax or macaques. Caution must be used in evaluating these data for a number of reasons: 1.) the number of samples tested from each species was very limited; 2.) the possibility that the animals being tested were at one time inoculated with human materials can not be eliminated, and; 3.) it is conceivable that these samples were infected with a related virus that is being detected as a result of a highly conserved region present in the two viruses. Though the products amplified from these animals are very similar by sequence analysis to the human isolates detected, it is not possible eliminate this final point as these sequences have not been extended beyond the amplified region.

As a result of the high viral prevalence, the present inventors were interested in determining the source of human infection. Because the rate of infection between volunteer blood donors and patients with non A-E hepatitis was not substantially different, it was surmised that the source would be common regardless of geographic location. Therefore, it was decided to test for the presence of TT virus in the serum of domesticated food animals utilizing the Set B primer assay. As demonstrated in Table 14, 20% of pigs, 25% of cows, 30% of sheep and 19% of chickens were positive for the presence of TT virus. Sequence determination and

TABLE 14

The presence of TTV in farm animals.

Figure 7:
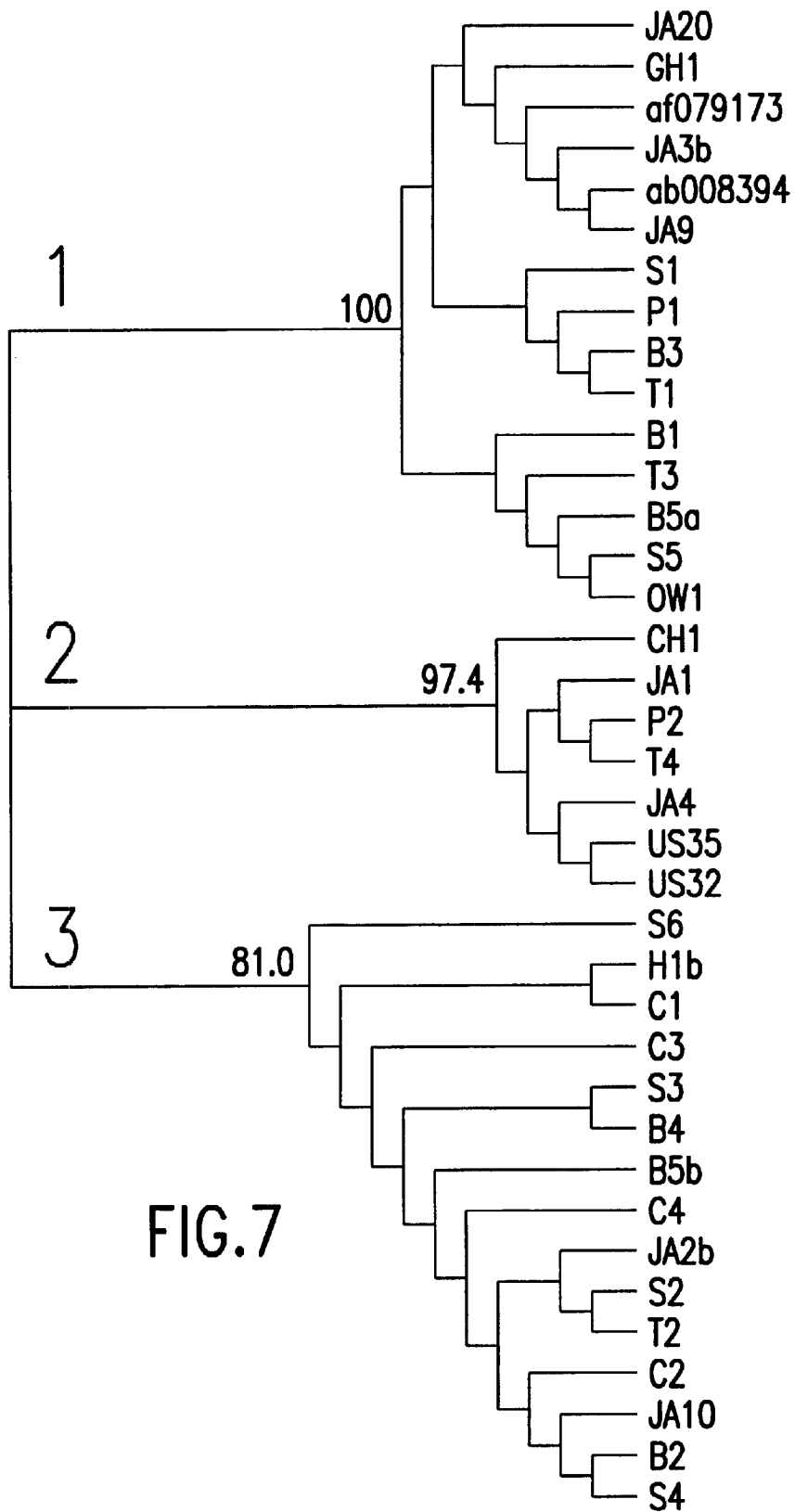
FIG. 7 shows a phylogenetic tree representing the genetic groupings of TT virus sequences generated with a conserved set of TT virus primersdescribed in example 7 where human isolates (Ghana, GH; Japan, JA; H, hemophiliac; United States, US), non-human isolates (Bovine, B; Chicken, C; Pan troglodytes, CH; Porcine, P; Aotus trivirgatus, OW; Ovine, S; Saguinus labiatus, T), and boot strap values are displayed.

| Group | Set B Positive | Percent Positive |
|---|---|---|
| Porcine (n = 20) | 4 | 20.0% |
| Bovine (n = 20) | 5 | 25.0% |
| Ovine (n = 20) | 6 | 30.0% |
| Chicken (n = 21) | 4 | 19.0% | phylogenetic analyses demonstrate that these sequences are similar to others detected with Set B primers, though the sequences do not cluster independently from the human isolates within this region (FIG. 7). In fact, the animal isolates are much more closely related to the human sequences than the human sequences are to one another. Of significance is the fact that only three of these animals are positive when tested with three previously described PCR assays (Nishizawa et al., *Biochem Biophys Res Commun* 241:92–97 (1997; Okamoto et al., *Hepatol. Res.* 10:1–16 (1998; Simmonds et al., *The Lancet* 352:191–194 (1998)).

Example 8

Use of TTV Sequence Diversity to Track Transmission of the Virus

An actual application of this method is presented in Example 1. The infectious nature of human TTV and the parenteral transmissibility of the virus to chimpanzees was demonstrated by the complete conservation of TTV sequences between source and recipient indicating that TTV infection was derived from its corresponding inoculum. In the following prophetic example, transmission of TTV between individuals is monitored by comparison of TTV DNA sequences obtained from the individuals involved.

Serum total nucleic acids (25 μl) are extracted from 2 or more individuals of interest using the DNA/RNA Extraction kit (Amersham Life Science Inc., Arlington Heights, Ill.). Nucleic acids are dissolved in 25 μl of nuclease-free water and 4 μl are used as template in the amplification reactions. oligonucleotide primers can be, but are not limited to, those described by Nishizawa (Nishizawa et al., *Biochem Biophys Res Commun* 241:92–97 (1997)) (SEQ ID NOS. 32 and 33 followed by SEQ ID NOS. 34 and 35) or Simmonds (Simmonds et al., *The Lancet* 352:191–194 (1998)) (SEQ ID NOS. 1 and 2 followed by SEQ ID NOS.3 and 4) or those described in example 7 (SEQ ID NOS. 60 and 61 followed by SEQ ID NOS. 62 and 63, or SEQ ID NOS. 64 and 65 followed by SEQ ID NOS. 66 and 67, or SEQ ID NOS. 68 and 69 followed by SEQ ID NOS. 70 and 71). Amplification reactions (20 μl) are performed for thirty-five cycles (94° C. for 20 seconds, 55° C. for 30 seconds, and 72° C. for 30 seconds) and contain 1.0 μM final concentration each primer and 1.5 units of Taq DNA polymerase (Perkin-Elmer, Foster City, Calif.). Nested PCR reactions are performed on 1.0 μl of the primary PCR reaction using the same amplification conditions as above. PCR products are purified by 2% agarose gel electrophoresis with visualization via ethidium bromide fluorescence, and are subsequently purified by excision and extraction of DNA. The amplification products encompass a region of known high variability and are sufficiently large such that the chance of two isolates having the exact, or nearly exact, nucleic acid sequence is minimized. Amplification products are sequenced, either partially or in full, and sequences are aligned using the program PILEUP (Wisconsin Package, version 9.0). PCR primer sequences are not included in the sequence alignment which is utilized to determine the percent identity between isolates. The more similar the TTV sequences are to one another, the more likely it is that the individuals involved were infected from a common source or that one individual infected the other.

This example also has applications to fields such as forensics. In this embodiment, comparison of TTV genomic sequences is used to establish previous contact between individuals and, depending on the mode of transmission, what the nature of the contact might be.

Example 9

Use of TTV as a Vector

In this example, construction of a TTV-based vector is described, along with its use in expressing foreign nucleic acids and/or proteins in eucaryotic cells. Other means of construction and applications of the TTV vector will be apparent to those of ordinary skill of the art when considering this disclosure.

An entire TTV genome is cloned in double stranded form, either as a single piece or in multiple fragments, as described in example 3 for isolate GH1 using anchored PCR. If obtained as multiple clones, the TTV genome is re-assembled into a single clone containing a plasmid-based replicon capable of propagation and selection in bacteria. The positions within the TTV genome sequence of the plasmid replicon and of a polylinker region containing multiple cloning sites are determined by the biology of TTV. For example, the sites should not interfere with desired properties of the vector, such as the ability to infect cells, replication, virion formation and propagation of infection. Other sequences are also required for vector function, and are derived either from TTV or other sources. These can include transcriptional controls (e.g. promoter, stop, polyadenylation and enhancer sequences) and expressions controls (e.g. Kozak sequences). The capacity of TTV to carry these additional sequences and remain functional, is evaluated by transfection of experimental vector constructs into a permissive eucaryotic cell line. Similarly, TTV sequences, non-essential to vector function, can be eliminated in order to increase the amount of foreign DNA the vector can accommodate.

A DNA fragment of interest (e.g. containing a protein binding site or encoding a RNA or protein) is inserted into the TTV vector cloning site and the ligated product is amplified in bacteria and then introduced into cell culture. The effect that the cloned insert has on the cells is studied, or the expressed product (e.g. any protein of interest such as an enzyme, antigen or recombinant vaccine protein) is isolated.

Alternatively, gene therapy of a host such a domesticated animal (e.g. cat, dog, pig, chicken, sheep or cow), primate or human can be performed using virions isolated from cell culture and used to infect the host. Infection of the host may also be possible by direct injection of the purified DNA vector into the animal. The infected host is monitored for effects of the vector insert (e.g. appearance of antibodies to an expressed vaccine antigen, compensation for a genetic defect by expression of a corrective gene, suppression of a harmful host gene by production of antisense RNA, production of medically or commercially useful products).

In other embodiments of this example:

(a) Portions of the TTV genome such as origin of replication, transcriptional controls, genes, packaging signals etc., are used as components of other eucaryotic vectors.

(b) A TTV-based episomal vector is constructed which contains deletions making it unable to infectious virions, and therefore not transmissible.

(c) A TTV-based helper virus system is constructed in which one or both members are derived from TTV, and in which one vector provides function(s) necessary for the production of virions from the other vector.

(d) A family of closely related TTV vectors is constructed as described above. Members of the family vary in those regions of the TTV genome that encode epitopes recognized by the immune system of a host, resulting in clearance of the vector. The epitope-encoding region for each vector is derived from a TTV isolate that does not show shared immunity with any of the other members of the vector family. Existence of such non-cross reactive TTV isolates is strongly suggested by the demonstration of co-infections and the high prevalence level in humans. An individual who has developed immunity to the initial vector, is treated with another member of the vector family to which immunity has not developed. Sequential treatment with different members of the vector panel described above is used to maintain or repeat therapy, a common problem with DNA virus-based gene therapy.

The primers of the present invention described herein thus are useful for detecting TTV in individuals. Other uses or variations of the present invention will be apparent to those of ordinary skill of the art when considering this disclosure.

| Sequence | Name |
|---|---|
| CAGACAGAGGAGAAGGCAACATG ; | A5430 |
| TACCAYTTAGCTCTCATTCTWA ; | A5427m |
| GGMAAYATGYTRTGGATAGACTGG ; | A8761 |
| CTACCTCCTGGCATTTTACCA ; | A5432 |
| GATGGTGCAAACYTTTGCCTCC ; | B19-FORWARD |
| GCATGACTTCAGTTAATTCTGCA ; | B19-REVERSE |
| AGACAGAGGAGAAGGCAACA ; | TTVjs-s1 |
| GACCAAAACATACACATGAA ; | TTVjs-a1 |
| GTAAGCGGGAACACTACAAC ; | B19.1699-s1 |
| CGGAGGAAACTGGGCTTCCG ; | B19.2119-a1 |
| CTAGCTGCACTTCCGAATGGCTG ; | TTV-JIM1? |
| GGTACTGTTGGTCATTGCGAGGTGG ; | TTV-JIM2? |
| GTGAAGCCACGGAGGGAGATCAG ; | TTV-jim3? |
| CCTGGCATCTTTCCATTTCCAAAG ; | A1 |
| GACTGGCTAACTAAAGATACCTCAG ; | S2 |
| TCCAAAGTTAAAACTGTAGGGTACG ; | A2 |
| GGGTCTGTGTGTACTAAGAGTTGG ; | N22-A1 |
| AAAGTCTGGCATTCATGTGTATG ; | N22-A2 |
| GCCAGGAGGTAGCAGCAATGTGC ; | N22-S1 |
| CTATTAGAATGAGAGCTAAGTGGTACC ; | N22-S2 |
| GCTAAGTACACTTGAGTACCATTGC ; | UFGH1-A1 |
| GGTACTGTTGGTCATTGCGAGGTGG ; | UFGH1-A2 |
| CTGGAAGGAAGAGTATGAGGCCTG ; | DFGH1-S1 |
| CCCTAGAGGCAATCTAAGAGACACC ; | DFGH1-S2 |
| AGCCTTTTGTGGGGTCTGTGTGTACTA ; | UFTTV1 |
| TGGAAATGGTAAAATGCCAGGAGGTAG ; | DFTTV1 |
| GTCTGGCATTCATGTGTATGTTTTGGTC ; | UFTTV2 |
| GCAGCAATGTGCCTATTAGAATGAGAGC ; | DFTTV2 |

TTTGTGCTACGTCACTAACCACGTGACGCCCACAGGCCAACCGAATGCTATGTC    TTV-GH1

GTGCACTTCCTGGGCCGGGTCTACGTCCTGATATAACTAGCTGCACTTCCGAAT

GGCTGAGTTTTCCACGCCCGTCCGCAGCGGTGAAGCCACGGAGGGAGATCAGCG

CGTCCCGAGGGCGGGTGCCGGAGGTGAGTTTACACACCGGAGTCAAGGGGCAAT

TCGGGCTCGGGACTGGCCGGGCTATGGGCAAGGCTCTGAAAAAAGCATGTTTAT

CGGCAGGCATTACAGAAAGAAAAGGGCGCTGTCACTGCTTGCTGTGCGAACAAC

ACAGAAGGCTCGCAAACTACTAATAGTGATGTGGACCCCACCTCGCAATGACCA

ACAGTACCTCAACTGGCAATGGTACTCAAGTGTACTTAGCTCCCACGCTGCTAT

GTGCGGGTGTCCCGACGCTGTCGCTCATTTTAATCATCTTGCTTCTGTGCTTCG

```
CGCCCCGCAAAATCCACCCCCGCCCGGTCCCCAGCGAAACCTGCCCCTCCGACG
GCTGCCAGCTCTCCCGGCTGCGCCAGAGGCGCCCGGAGATAGAGCACCATGGCC
TATGGCTGGTGGCGCCGAAGGAGAAGAAGGTGGCGCAGGTGGCGACGCAGACCA
TGGAGGCGCCGCTGGAGGACCCGAAGACGCAGACCTGCTAGACGCCGTGGCCGC
CGCAGAAACGTAAGGAGACGGCGCCGAGGAGGAGGTGGAGGAGGAGGTACAGG
AGATGGAAAAGAAAGGGCAGGCGGAGAAAGAAAGCTAAAATAATAATAAGACAA
TGGCAACCAAACTACAGGAGGAGATGTAACATAGTGGGCTACATTCCCGTACTG
ATATGTGGCGAAAATACTGTCAGCAGAAACTATGCCACACACTCAGACGATACC
AACTACCCAGGACCCTTTGGGGGGGTATGACTACAGACAAATTTACTCTAAGA
ATCCTGTATGGTGAGTACAAGAGGTTTATGAACTACTGGACAGCATCTAACGAA
GATCTAGACCTCTGTAGATATCTGGGAGTAAACCTGTACTTTTTCAGACACCCA
GATGTAGACTTTATCATAAAGATAAATACTATGCCTCCTTTCTTAGACACAGAA
CTCACAGCCCCTAGCATACACCCAGGCATGCTAGCCTTAGACAAGAGAGCAAGG
TGGATACCCAGCTTAAAATCTAGACCGGGAAAAAAGCACTATATTAAGATAAGA
GTAGGGGCACCTAAAATGTTCACAGATAAGTGGTACCCCCAAACAGACCTCTGT
GACATGGTGCTGCTAACCGTCTATGCGACCGCAGCGGATATGCAATATCCGTTC
GGCTCACCACTAACTGACTCTGTGGTTGTGAACTTCCAGGTTCTGCAATCCATG
TATGATGAAAAAATTAGCATATTACCAGACGAAAAAATCCAAAGACAAAACCTA
TTAACTAGTATATCAAACTATATTCCTTTCTATAATACCACACAGACAATAGCT
CAGCTAAAACCATTTGTAGATGCAGGCAATGCAATATCAGGAACAACCACAACA
ACATGGGGATCACTAQTAAACACAACCAAATTCACAACTACAACTACCACCACA
TACACTTACCCAGGTACAACAAACACAACAGTAACTTTTATAACAGCTAATGAC
AGCTGGTACAGAGGCACAGTATACAACCAAAACATAAAAGACGTAGCAAAAAAA
GCAGCAGAACTATACTCAAAAGCAACAAAAGCTGTACTAGGAAACACATTCACT
ACAGAAGATTATACACTAGGATACCACGGAGGCCTATATAGCTCCATATGGCTA
TCCCCCGGTAGATCTTACTTTGAAACACCAGGAGCATACACAGACATAAAATAT
AATCCTTTTACAGACAGAGGAGAAGGAAACATGCTGTGGATAGACTGGCTAAGC
AAAAAAAATATGAACTATGACAAAGTACAAAGTAAATGCCTAATATCAGACCTA
CCTCTGTGGGCAGCAGCATATGGCTATGTAGAATTCTGTGCAAAAAGCACAGGA
GACCAAAACATACACATGAATGCCAGACTTTTAATAAGAAGTCCCTTTACAGAC
CCCCAACTCTTAGTACACACAGACCCCACCAAAGGCTTTGTTCCTTACTCCCTA
AATTTTGGAAATGGTAAAATGCCAGGAGGTAGCAGCAATGTGCCTATTAGAATG
AGAGCTAAGTGGTACCCCACACTACTTCACCAGCAAGAAGTACTAGAGGCCTTA
GCACAGTCAGGCCCCTTTGCATACCACGCAGACATTAAAAAAGTATCTCTGGGT
ATGAAATACCGTTTTAAGTGGATCTGGGTGGAAACCCCGTTCGCCAACAGGTT
GTTAGAAATCCCTGCAAAGAAACCCACTCCTCGGGCAATAGAGTCCCTAGAAGC
TTACAAATCGTTGACCCGAAATACAACTCACCGGAACTCACTTTCCATACCTGG
GACTTCAAACGTGGCCTCTTTGGCCCGAAAGCTATTCAGAGAATGCAACAACAA
CCAACAACTACTGACATTTTTTCAGCAGGCCGCAAGAGACCCAGGAGGGACACC
GAGGTGTACCACTCCAGCCAAGAAGGGGAGCAAAAAGAAAGCTTACTTTTCCCC
```

-continued

```
CCAGTCAAGCTCCTCAGACGAGTCCCCCCGTGGGAAGACTCGCAGCAGGAGGAA
AGCGGGTCGCAAAGCTCAGAGGAAGAGACGCAGACCGTCTCCCAGCAGCTCAAG
CAGCAGCTGCAGCAACAGCGAATCCTGGGAGTCAAACTCAGACTCCTGTTCAAC
CAAGTCCAAAAAATCCAACAAAATCAAGATATCAACCCTACCTTGTTACCAAGG
GGGGGGGATCTAGCATCCTTATTTCAAATAGCACCATAAACATGTTTGGAGACC
CCAAACCCTACAACCCTTCCAGTAATGACTGGAAGGAAGAGTATGAGGCCTGTA
ARTACTGGGACAGACCCCCTAGAGGCAATCTAAGAGACACCCCCTACTACCCCT
GGGCCCCCAAGGAGAACCAGTACCGTGTAAACTTTAAGCTTGGATTTCAATAAA
GCTAGGCCGTGGGACTTTCACTTGTCGGTGTCTGCTTATAAAGGTCACCAAGCA
CTCCGAGCGGAGCGAGGAGTGCGACCCTTGGGGGCTCAACGCCTTCGGAGCCGC
GCGCTACGCCTTCGGCTGCGCGCGGCACCTCAGACCCCCGCTCGTGCTGACGCG
CTCGCGCGCGTCAGACCACTTCGGGCTTGCGGGGGTCGGGAAATTTGCTAAACA
GACTCCGAGTTGCCATTGGACACTGGAGCTGTGAATCAGTAACGAAAGTGAGTG
GGGCCAGACTTCGCCATAAGGCCTTTATCTTCTCGCCATTTGTCAGTGTCGGGG
GTCGCCGTAGGCTTCGGCCTCCATTTTAGGGCCTAAAAACTACCAAAATGGCCG
TTCCAGTGACGTCACAGCCGCCATTTTAAGTAGCTGACGTCAAGGATTGACGTG
AAGGTTAAAGGTCATCCTCGGCGGAAGCTACACAAAATGGTGGACAACATCTTC
CGGGTCAAAGGTCGTGCACACGTCATAAGTCACGTGGTGGGGACCCGCTGTAAC
CCGGAAGTAGGCCCCGTCACGTGATTTGTCACGTGTGTACACGTCACCGCCGCC
ATTTTGTTTTACAAAATGGCCGACTTCCTTCCTCTTTTTTAAAAAAAGGCGCCA
AAAAACCGTCGGCGGGGGGCCGCGCGCTGCGCGCGCGGCCCCCGGGGAGGCA
TTGCCTCCCCCCCCGCGCGCATGCGCGCGGGTCCCCCCCCCTCCGGGGGCTC
CGCCCCCCGGCCCCCCCC
;

MAEFSTPVRSGEATEGDQRVPRAGAGGEFTHRSQGAIRARDWPGYGQGSEKSMF    GH-1-orf2
IGRHYRKKRALSLLAVRTTQKARKLLIVMWTPPRNDQQYLNWQWYSSVLSSHAA
MCGCPDAVAHFNHLASVLRAPQNPPPPGPQRNLPLRRLPALPAAPEAPGDRAPW
PMAGGAEGEEGGAGGDADHGGAAGGPEDADLLDAVAAAET
;

MAYGWWRRRRRRWRRRWRRRPWRRRWRTRRRRPARRRGRRRNVRRRRRGGRWRRR    GH1-orf1
YRRWKRKGRRRKKAKIIIRQWQPNYRRRCNIVGYIPVLICGENTVSRNYATHSD
DTNYPGPFGGGMTTDKFTLRILYGEYKRFMNYWTASNEDLDLCRYLGVNLYFFR
HPDVDFIIKINTMPPFLDTELTAPSIHPGMLALDKRARWIPSLKSRPGKKHYIK
IRVGAPKMFTDKWYPQTDLCDMVLLTVYATAADMQYPFGSPLTDSVVVNFQVLQ
SMYDEKISILPDEKIQRQNLLTSISNYIPFYNTTQTIAQLKPFVDAGNAISGTT
TTTWGSLLNTTKFTTTTTTYTYPGTTNTTVTFITANDSWYRGTVYNQNIKDVA
KKAAELYSKATKAVLGNTFTTEDYTLGYHGGLYSSIWLSPGRSYFETPGAYTDI
KYNPFTDRGEGNMLWIDWLSKKNMNYDKVQSKCLISDLPLWAAAYGYVEFCAKS
TGDQNIHMNARLLIRSPFTDPQLLVHTDPTKGFVPYSLNFGNGKMPGGSSNVPI
RMRAKWYPTLLHQQEVLEALAQSGPFAYHADIKKVSLGMKYRFKWIWGGNPVRQ
QVVRNPCKETHSSGNRVPRSLQIVDPKYNSPELTFHTWDFKRGLFGPKAIQRMQ
```

QQPTTTDIFSAGRKRPRRDTEVYHSSQEGEQKESLLFPPVKLLRRVPPWEDSQQ

EESGSQSSEEETQTVSQQLKQQLQQQRILGVKLRLLFNQVQKIQQNQDINPTLL

PRGGDLASLFQIAP

| | | |
|---|---|---|
| GCAGCAGCATATGGATATGT | RD037 | ; |
| TGACTGTGCTAAAGCCTCTA | RD038 | ; |
| CATACACATGAATGCCAGGC | RD051 | ; |
| GTACTTCTTGCTGGTGAAAT | RD052 | ; |
| CTCTTTAAACTTTGGAAATGGTAAAATGCC | dfttv0.5 | ; |
| GTCTGGCATTCATGTGTATGTTTTGGTC | ufttv1 | ; |
| TGGAAATGGTAAAATGCCAGGAGGTAG | dfttv2-2 | ; |
| AGCCTTTTGTGGGGTCTGTGTGTACTA | ufttv2-2 | ; |
| GTCTGGCATTCATGTGTATGTTTGTGTC | ufttv1b | ; |
| CAGTTTTAACTTTGGAAATGGAAAGATGCC | dfttv2b | ; |
| ATCTACAGTTGTGTTCTATGTTTGTGTC | ufttv2a | ; |
| TGGAAATGGAAAGATGCCAGGCGGCAG | dfttv2b-2 | ; |
| ATCCCCTGAGGGGGTTGTTGTGATCTA | ufttv2b-2 | ; |
| TAGCCTCAACTTTGGAAATGGTAAAATGCC | dfttv2c | ; |
| TGGAAATGGTAAAATGCCAGGCGGTAG | dfttv2c-2 | ; |
| ATCCTCTGAGGGGATTGTTGTGGTCTA | ufttv2c-2 | ; |
| TACTACTCTGGCGTTCATGTCTATG | uftype3-a1 | ; |
| CAGTATTCTGCGTACCCGTATACTG | uftype3-a2 | ; |
| CAGGAGACTCTAACATAGACATGAACG | dfttv1-3con | ; |
| TAACATAGACATGAACGCCAGAGTAG | dfttv2-3con | ; |

ATTTTGCTACGTCACTAACCGCGTGACACCCACAGGCCAACCGAATGCTATGTC    JA9

ATCCATTTCCTGGGCCGGGTTTACGTCCTCATATAAGTAAGCGCACTTCCGAAT

GGCTGAGTTTTCCACGCCCGTCCGCAGCGGTGAAGCCACGGAGGGAGATCTCCG

CGTCCCGAGGGCGGGTGCCGAAGGTGAGTTTACACACCGAAGTCAAGGGGCAAT

TCGGGCTCGGGACTGGCCGGGCTATGGGCAAGGCTCTGAAAAAAGCATGTTTAT

TGGCAGGCATTACAGAAAGAAAAGGGCGCTGTCACTGTATGCTGTGCGAACAAC

AAAGAAGGCTTGCAAACTACTAATAGTAATGTGGACCCCACCTCGCAATGATCA

ACAGTACCTTAACTGGCAATGGTACTCAAGTGTACTTAGCTCCCACGCTGCTAT

GTGCGGGTGTCCCGACGCTGCTGCTCATTTTAATCATCTTGCTTCTGTGCTTCG

TGCCCCGCAAAACCCACCCCCTCCCGGTCCCCAGCGAAACCTGCCCCTCCGACG

GCTGCCGGCTCTCCCGGCTGCGCCAGAGGCGCCCGGAGATAGAGCACCATGGCC

TATGGCTGGTGGCGCCGAAGGAGAAGACGGTGGCGCAGGTGGAGACGCAGACCA

TGGAGGCGCCGCTGGAGGACCCGAAGACGCAGACCTGCTAGACGCCGTGGCCAC

CGCAGAAACGTAAGGAGACGCCGCAGAGGAGGGAGGTGGAGGAGGAGATATAGG

AGATGGAAAAGAAAGGGCAGGCGCAGAAAAAAAGCTAAAATAATAATAAGACAA

TGGCAACCAAACTACAGAAGGAGATGTAACATAGTAGGCTACATCCCTGTACTA

-continued
ATATGTGGCGAAAATACTGTCAGCAGAAACTATGCCACACACTCAGACGGTACC
AACTACCCAGGACCCTTCGGGGGGGTATGACTACAGACAAATTTACTTTAAGA
ATTTTGTATGATGAGTACAAAAGGTTTATGAACTACTGGACAGCATCTAACGAA
GACCTAGACCTTTGTAGATATCTAGGAGTAAACATGTACCTTTTCAGACACCCA
GATGTAGATTTTATCATAAAAATTAATACCATGCCTCCTTTTCTAGACACAGAA
CTCACAGCCCCTAGCATACACCCAGGCATGCTAGCCCTAGACAAAAGAGCAAGA
TGGATACCTAGCTTAAAATCTAGACCGGGAAAAAAACACTATATTAAAATAAGA
GTAGGGGCACCAAAAATGTTCACTGATAAATGGTACCCCCAAACAGATCTTTGT
GACATGGTGCTTCTAACTGTCTATGCAACCGCAGCGGATATGCAATATCCGTTC
GGCTCACCACTAACTGACTCTGTGGTTGTGAACTTCCAGGTTCTGCAATCCATG
TATGATGAACATATTAGCATATTACCAGACCAACAAACACACAGAGAAAATTTA
CTTAGTAACATAACAAAATACATTCCCTTTTATAATACCACACAAACTATAGCC
CAATTAAAGCCATTTATAGATGCAGGCAATGTAACAACAAGCACAACACCACTA
ACATGGGATCATGCATAAACACAACCAAGTTTACTACAGCAACCACAGTAACT
TATACATATCCAGGCACCACCACAACCACAGTAACTATGTTAAGCTGTAATGAC
TCCTGGTACAGAGGAACAGTATATAACAATAAAATTACAGAAGTACCAATAAAA
GCAGCTACATTATACTCAAAGGCAACAAAAACCTTGCTAGGAAACACCTTCACA
ACTGAGGACTACACACTAGAATATCATGGAGGACTGTACAGCTCAATATGGCTA
TCCGCTGGTAGATCTTACTTTGAAACACCAGGAGCATATACAGACATAAAGTAC
AATCCATTCACAGACAGAGGAGAAGGCAACATGTTATGGATAGACTGGGTAAGC
AAAAAAAACATGAACTATGACAAAGTACAAAGTAAATGCTTAATATCAGACATA
CCTCTATGGGCAGCAGCATATGGATATGTAGAATTTTGTGCAAAAAGTACAGGA
GACCAAAACATACACATGAATGCCAGGCTACTAATAAGAAGTCCCTTTACAGAC
CCACAACTACTAGTACACACAGACCCCACAAAAGGCTTTGTTCCTTACTCTTTA
AACTTTGGAAATGGTAAAATGCCAGGAGGTAGTAGTAATGTGCCTATTAGAATG
AGAGCTAAATGGTATCCAACATTATTTCACCAGCAAGAGGTACTAGAGGCCTTA
GCACAGTCAGGCCCCTTTGCATACCACTCAGACATTAAAAAAGTATCTCTGGGT
ATGAAATACCGTTTTAAGTGGATCTGGGGTGGAAACCCCGTTCGCCAACAGGTT
GCTAGAAATCCCTGCAAAGAAACCCACTCCTCGGTCAATAGAGTCCCTAGAAGC
TTACAAATCGTTGACCCGAAATACAACTCACCGGAACTCACATTCCATACCTGG
GACTTCAGACGTGGCCTATTTGGCCCGAAAGCTATACAGAGAATGCAACAACAA
CCAACAACTACTGACATTTTTTCAGCAGGCCGCAAGAGACCCAGGAGGGACACC
GAGGTGTACCACTCCAGCCAAGAAAGGGAGCAAAAAGAAAGCTTACTTTTCCCC
CCAGTCAAGCTCCTCAGACGAGTCCCCCCGTGGGAAGACTCGCAGCAGGAGGAA
AGCGGGTCACAAAGCTCAGAGGAAGAGACGCAGACACTCTCCCAGCAGCTCAAG
CAGCAGCTGCCGCAACAGCGAATCCTGGGACTCAAACTCAGACTCCTATCCAAC
CAAATCCAAAAAATCCAACAAAATCAAGATATCAACCCTACCTTGTTACCAAGG
GGGGGGGATCTAGCATCCTTATTTCAAATAGCACCATAAACATGTTTGGTGACC
CCAAACCTTACAACCCTTCCAGTAATGACTGGAAAGAGGAGTACGAGGCCTGTA
GAATATGGGACAGACCCCCCAGAGGCAACCTAAGAGATACCCCTTTCTACCCCT -continued

```
GGGCCCCCAAGGAAAACCAGTACCGTGTAAACTTTAAACTTGGATTTCAATAAA
GCTAGGCCGTGGGACTTTCACTTGTCGGTGTCTACTTATAAAAGTAACTAAGCA
CTCCGAGCGAAGCGAGGAGTGCGACCCTTGGGGGCTCAACGCCTTCGGAGCCGC
GCGCTACGCCTTCGGCTGCGCGCGGCACCTCAGACCCCCGCTCGTGCTGACACG
CTCGCGCGTGTCAGACCACTTCGGGCTCGCGGGGGTCGGGAAATTTACTAAACA
GACTCCGAGTTGCCATTGGACTCAGGAGCTATGAATCAGTAACGAAAGTGAGTG
AGGCCAGACTTCGCCATAAGGCCTTTATCTTCTTGCCATTTGTCAGTAACAGGG
GTCGCCATAGACTTCGGCCTCCATTTTACCTTGTAAAAACTACCAAAATGGCCG
TTCCAGTGACGTCACAGCCGCCATTTTAAGTAGCTGACGTCAAGGATTGACGTA
AAGGTTAAAGGTCATCCTCGGCGGAAGCTACACAAAATGGTGGACAACATCTTC
CGGGTCAAAGGTTGTGCATACGTCACAAGTCACGTGGAGGGGACACGCTGTAAC
CCGGAAGTAGGCCCCGTCACGTGACTTACCACGTGTGTACACGTCACCGCCGCC
ATTTTGTTTAACAAAATGGCTGACTTCCTTCCTCTTTTTTGAAAAAAGGCGCCA
AAAACCGTCGGCGGGGGGCCGCGCGCTGCGCGCGGCCCCCGGGGGAGGCA
TTGCCTCCCCCCCCGCGCGCACGCGCGCGGGTCCCCCCCCCTCCGGGGGGCTC
CGCCCCCCGGCCCCCCCC
;

GGCTTAGTGCGTCACCACCCACGTGACCCGCCTCCGCCAATTAACAGGTACTTC       JA20
GTACACTTCCTGGGCGGGCTTATAAGACTAATATAAGTAGCTGCACTTCCGAAT
GGCTGAGTTTTCCACGCCCGTCCGCAGCGGTGAAGCCACGGAGGGAGCTCAGCG
CGTCCCGAGGGCGGGTGCCGGAGGTGAGTTTACACACCGCAGTCAAGGGGCAAT
TCGGGCTCGGGACTGGCCGGGCTTTGGGCAAGGCTCTTAAAAAAGCTATGTTTA
TTGGCAGGCACTACCGAAAGAAAAGGGCGCTGCTACTGCTATCTGTGCATTCTA
CAAAGACAAAAGGGAAACTTCTAATAGCTATGTGGACTCCCCCACGCAATGATC
AACAATACCTTAACTGGCAATGGTACACTTCTGTACTTAGCTCCCACTCTGCTA
TGTGCGGGTGTTCCGACGCTATCGCTCATCTTAATCATCTTGCTAATCTGCTTC
GTGCCCCGCAAAATCCGCCCCCGCCTGATAATCCAAGACCCCTACCCGTGCGAG
CACTGCCTGCTCCCCCGGCTGCCCACGAGGCAGCCGGTGATCGAGCACCATGGC
CTATGGGTGGTGGAGGAGACGCCGGAGGCGCTGGCGCAGGTGGAGACGCCGACC
ATGGAGGCGCCGCTGGAGGACCCGCAGACGCAGACCTGCTAGACGCCGTGGCCG
CCGCAGAAACGTAAGGAGACGGCGCAGAGGGAGGTGGAGAAGGAGGTACAGGAG
GTGGAAAAGAAAGGGCAGACGTAGAAGAAAAGCAAAAATAATAATAAGACAGTG
GCAGCCAAACTACAGAAGAAGATGTAATATAGTGGGCTACCTCCCTATACTTAT
CTGTGGTGGAAATACTGTTTCTAGAAACTATGCCACACACTCAGACGATACTAA
CTATCCAGGACCCTTTGGGGGAGGCATGACCACAGACAAATTCAGCCTTAGAAT
ACTATATGATGAATACAAAAGATTTATGAACTACTGGACAGCCTCAAATGAGGA
CCTAGATCTCTGTAGATATCTAGGATGCACTTTTTACTTCTTTAGACACCCTGA
AGTAGACTTTATTATAAAAATAAACACCATGCCCCCATTCTTAGATACAACCAT
AACAGCACCTAGCATACACCCAGGCCTCATGGCCCTAGACAAAAGAGCCAGATG
GATTCCTTCTCTTAAAAATAGACCAGGTAAAAAACACTATATAAAAATTAGAGT
AGGGGCTCCTAAAATGTTCACAGATAAATGGTACCCTCAAACAGACCTCTGTGA
```

-continued

```
CATGACACTGCTAACTATCTATGCAACCGCAGCGGATATGCAATATCCGTTCGG

CTCACCACTAACTGACACTGTGGTTGTTAACTCCCAAGTTCTGCAATCCATGTA

TGATGAAACAATTAGCATATTACCTGATGAAAAAACTAAAAGAAATAGCCTTCT

TACTTCTATAAGAAGCTACATACCTTTTTATAATACTACACAAACAATAGCTCA

ATTAAAACCATTTGTAGATGCAGGAGGACACACAACAGGCTCAACAACAACTAC

ATGGGACAACTATTAAACACAACTAAATTTACCACTACCACAACAACCACATA

CACATACCCTGGCACCACAAATACAGCAGTAACATTTATAACAGCCAATGATAC

CTGGTACAGGGGAACAGCATATAAAGATAACATTAAAGATGTACCACAAAAAGC

AGCACAATTATACTTTCAAACAACACAAAAACTACTAGGAAACACATTCCATGG

CTCAGATGAAACACTTGAATACCATGCAGGCCTATACAGCTCTATCTGGCTATC

ACCAGGTAGATCCTACTTTGAAACACCAGGTGCATACACAGACATTAAATATAA

CCCTTTTACAGACAGAGGAGAAGGCAACATGCTGTGGATAGACTGGCTAAGTAA

AAAAAACATGAAATATGACAAAGTGCAAAGTAAGTGCCTAGTAGCAGACCTACC

ACTGTGGGCAGCAGCATATGGTTATGTAGAATTCTGCTCTAAAAGCACAGGAGA

CACAAACATACACATGAATGCCAGACTACTAATAAGAAGTCCTTTTACAGACCC

CCAGCTAATAGTACACACAGACCCCACTAAAGGCTTTGTACCCTATTCTTTAAA

CTTTGGAAATGGTAAAATGCCAGGAGGTAGCAGCAATGTTCCCATAAGAATGAG

AGCTAAGTGGTACCCCACTTTATCCCACCAACAAGAAGTTCTAGAGGCCTTAGC

ACAGTCAGGACCCTTTGCTTATCACTCAGACATTAAAAAAGTATCTCTAGGCAT

AAAATACCGTTTTAAGTGGATCTGGGGTGGAAACCCCGTTCGCCAACAGGTTGT

TAGAAATCCCTGCAAGGAACCCCACTCCTCGGGCAATAGAGTCCCTAGAAGCAT

ACAAATCGTTGACCCGAGATACAACTCACCGGAACTTACCATCCATGCCTGGGA

CTTCAGACGTGGCTTCTTTGGCCCGAAAGCTATTCAAAGAATGCAACAACAACC

AACTGCTACTGAATTTTTTTCAGCAGGCCGCAAGAGACCCAGAAGGGACACAGA

AGTGTATCAGTCCGACCAAGAAAAGGAGCAAAAAGAAAGCTCGCTTTTCCCCCC

AGTCAAGCTCCTCCGAAGAGTCCCCCCGTGGGAGGACTCGGAACAGGAGCAAAG

CGGGTCGCAAAGCTCAGAGGAAGAGACGGCGACCCTCTCCCAGCAGCTCAAACA

GCAGCTGCAGCAGCAGCGAGTCTTGGGAGTCAAACTCAGACTCCTGTTCAACCA

AGTCCAAAAAATCCAACAAAATCAAGATATCAACCCTACCTTGTTACCAAGGGG

GGGGGATCTAGTATCCTTCTTTCAGGCTGTACCATAAATATGTTTCCAGACCCT

AAACCTTACTGCCCCTCCAGCAATGACTGGAAAGAAGAGTATGAGGCCTGTAAA

TATTGGGATAGACCTCCCAGACACAACCTTAGAGACCCCCCCTTTTACCCCTGG

GCCCCTAAAAACAATCCTTGCAATGTAAGCTTTAAACTTGGCTTCAAATAAACT

AGGCCGTGGGAGTTTCACTTGTCGGTGTCTACCTCTATAAGTCACTAAGCACTC

CGAGCGCAGCGAGGAGTGCGACCCTTCCCCCTGGTGCAACGCCCTCGGCGGCCG

CGCGCTACGCCTTCGGCTGCGCGCGGCACCTCGGACCCCCGCTCGTGCTGACAC

GCTTGCGCGTGTCAGACCACTTCGGGCTCGCGGGGGTCGGGAAATTTGCTAAAC

AGACTCCGAGTTGCCATTGGACACTGTAGCTATGAATCAGTAACGAAAGTGAGT

GGGGCCAGACTTCGCCATAAGGCCTTTATCTTCTTGCCATTTGTCAGTATTGGG

GGTCGCCATAAACTTTGGGCTCCATTTTAGGCCTTCCGGACTACAAAAATCGCC
```

-continued

```
ATATTTGTGACGTCAGAGCCGCCATTTTAAGTCAGCTCTGGGGAGGCGTGACTT
CCAGTTCAAAGGTCATCCTCACCATAACTGGCACAAAATGGCCGCCAACTTCTT
CCGGGTCAAAGGTCACTGCTACGTCATAGGTGACGTGGGGGGGACCTACTTAA
ACACGGAAGTAGGCCCCGACACGTCACTGTCACGTGACAGTACGTCACAGCCGC
CATTTTGTTTTACAAAATAGCCGACTTCCTTCCTCTTTTTTAAAAAAAGGCGCC
AAAAAACCGTCGGCGGGGGGCCGCGCGCTGCGCGCGCGGCCCCGGGGAGGC
ACAGCCTCCCCCCCCGCGCGCATGCGCGCGGGTCCCCCCCCCTCCGGGGGGCT
CCGCCCCCCGGCCCCCCC
;
GCTACGTCACTAACCTACGTGTCCGTCTCCTATAGGCCGGACACCGTCTACGTC    JA1
ATACACCTCCTGGGCATGGTCTACGTGATAATATAAGTGGCAGCACTTCCGAAT
GGCTGAGTTTTCCACGCCCGTCCGCGGAGAGGGAGCCACGGAGGTGATCCCGAA
CGTCCCGAGGGCGGGTGCCGGAGGTGAGTTTACACACCGGAGTCAAGGGGCAAT
TCGGGCTCGGGACTGGCCGGGCTATGGGCAAGACTCTGAAAAATGCACTTTTCT
AGGTGTAGCAGAAAGAAAAGGACACTGTCACTGCTACCACTGCACCCTTCACAG
AAAGCTAGGCCATCTGTGAGAGGTATGTGGAGACCCCCAGGCGAAATGAATTC
ACTATTCAACGTGACTGGTTCTACAGTTGCTTTCACTCCCACTCTTCTATGTGT
GGCTGTGCTGATTTTATTAATCATCTCAATCATATCGCTGCTATGCTCGGCCGT
CCGGAAGACCAGAACCCTCCTCCGCCACCCGGGGCTCTAAGACCCCTACCTGCT
CTCCCGGCCGCCCCGAGGCGCCCGGTGATCGAGCACCATGGCCTATGGGTGGT
GGCGCAAGCGGCGAAGGCGCCCGTGGTGGAGGAGGAGATGGCGCCGCTGGAGAC
GCCGTCGGAGACCCCGCAGACGCCGACCTCGTCGCCGCTATCGACGCCGCAGAA
CAGTAAGGAGACGCGGCAGGGGAGGTGGACTAAGAGATATAGACGATGGCGCC
GCAAAGGCAAACGCAGAGGCAAAAAAAAAATTATTATAAAACAATGGCAGCCCA
ACTACAGACGCAGATGCAACATAGTGGGCTACATGCCTCTACTTATATGTGGGG
AAAATACTGTTGCCAGAAACTATGCCACCCACTCAGACGACAGCTACTACCCTG
GACCCTTTGGGGGGGAATGACCACAGACAAATTTACTCTAAGAATTCTATATG
ATGAATACAAGAGATTTATGAATTACTGGACAGCCTCAAACGAGGACCTAGACT
TGTGTAGATACCTAGGATGTACTCTATATGTATTTAGACACCCAGAAGTAGACT
TTATAATTATAATAAACACATCTCCTCCATTTCTAGACACAGAGATAACAGGCC
CCAGCATACACCCGGGTATGATGGCCCTCAACAAAAGAGCCAGATGGATACCTA
GCATAAAAAACAGACCAGGCAGAAAACACTATGTAAAGATTAAAGTGGGAGCCC
CCCGAATGTTCACAGATAAGTGGTACCCCAGACAGACCTCTGTGACATGACAC
TCCTAACGATCTTTGCCTCTGCGGCGGATATGCAATATCCGTTCGGCTCACCAC
TAACTGACACTATAGTTGTGTCATTCCAAGTTCTGCAATCCATGTTCAACGACT
GCCTGAGTGTACTTCCTACTAACTTTACAGAAACATCAGGCAAAGGCGCACAAT
TACATGATAAAATTATTAACCATTTACCCTACTACAACACCACACAAACACAAG
CACAATTTAAGAGATTTACAGAAAACCAAGAAGCAACAAATGGAAACAATGTAT
GGGCAAACTACGTAAACAGCTGTAAATTTAACAAACAAGAATCACCTAAAAGTG
ACAATGGCATAGGAGGCCCATACTGCTCATACTCAGACACATGGTACAAAGGCA
```

-continued

```
CAGCATACAATAACAAAATTACAACTATACCTGAAAAAGCAAGCAAACTATACT
ATGAGGAGACTAAAAAATTAATAGGAATAACATTTACAGGATCCTCACACAGGT
TGCACTACTGCGGAGGCCTGTACTCCTCAGTATGGCTATCTGCAGGCAGATCAT
ACTTTGAAACCAAGGGTCCCTACACAGACATAACATACAACCCATTCTCAGACA
GAGGCGAAGGCAACATGCTGTGGATAGACTGGCTAACTAAAGACACCTCAGTAT
ATGAGAAAACACAGAGTAAATGTCTTATACAAGACATGCCCTTATGGGCCYCTG
TGTTCGGATTCTCCGAGTACTGCAGTAAAGTAACAGGAGACACAAACATAGAAC
ACRACTCCAGATGTGTTATTAGAAGCCCCTACACAGTGCCACAACTGTTAGATC
ACAACAACCCCCTCAGGGGATACGTGCCCTACAGTTTTAACTTTGGAAATGGAA
AGATGCCAGGCGGCAGCAGCCAGGTACCCATTAGAATGAGAGCAAAGTGGTACC
CTACCCTTTTTCACCAAAAAGAAGTACTAGAAGCCATTGCACAGTCGGGCCCCT
TCGCATATCACTCAGATATTAAAAAAGTGTCACTGGGCTTAAAATACAGATTTA
AGTGGGTGTGGGGTGGCAACCCCGTGTCCCAACAGGTTGTTAGGAACCCCTGCA
AGACCACCCAAGGTTCCTCGGGCAATAGACTCCCTCGATCAATACAAGTCGTTG
ACCCGCGGTACAACACACCAGAACTCACCATTCACGCGTGGGACTTCAGACATG
GGTTCTTTGGCAGAAAAGCTATTAAGAGAATGCAAGAACAACCAATACCTCATG
ACACTTTTTCAGCAGGGTACAAACGCAGCCGCCGAGATACAGAAGCACTCCAAT
CCAGCCAAGAAGAGCAACAAAAAGAAAACTTACTTTTCCCAGTCCAGCAGCTCA
AGCGAGTCCCCCCGTGGGAGACGTCGCAAGAGAGCCAAAGCGAGGAAGAAACCT
CGCAAAAACAGGAGACCCTCTCCCAGCAACTCAGAGACCAGCTGCACAAGCAGC
GGGTCATGGGAGACCAACTCAGGTCACTCATCTACCAAATGCAGAGGGTCCAAC
AAAATCAACACATAAACCCTATGTTATTGCCAAAGGGTCTGGCATTAACTTCTA
TTTCTCGCAGTGTAACATAGATATGTTCGGGGACCCCAAACCCTACAACCCCTC
CTCCAATGACTGGAAGGAGGAGTACGAGGCCTGCAGGTACTGGGACAGACCCCC
CAGACACAACCTGAGGAGCACCCCCCACTATCCCTGGGCCCCCACCCCCAAACC
ATACCGTGTCAACTTTGCCCTCAACTACAAATAAACGGTGGCCGTGGGAGCTTC
ACTTGTCGGTGTCTACCTCTTAAGGTCACTAAGCACTCCGAGCGTCAGCGAGGA
GTGCGACCCTTAACCAAGGGGCAACTCCCTCGAAGTCCGGCGCTACGCGCTTCG
CGCTGCGCCGGACATCTCGGACCCCCCCTCGACCCGAATCGCTTGCGCGATTCG
GACCTGCGGCCTCGGGGGGTCGGGGCTTTACTAAACAGACTCCGAGGTGCCA
TTGGACACTGAGGGGCAAACAGCAACGAAAGTGAGTGGGCCAGGCTTTGCCA
TAAGGCCTTTATCTTCTTGCCATTTGTCCGCGACCGGGGTCGCTCCTAGACGC
GGACCCCGTTTCGGGGTCCTTCCGGATTCCTCGGCGCCGTTCCAGTGACGTCAC
GGGCGCCATGTTAAGTGGCTGTCGCCGAGGATTGACGTCACAGTTCAAAGGTCA
TCCTCGACGGTAACCGCAAACATGGCGGACAATCTCTTCCGGGTCAAAGGTCGT
GCATGCGTCATAAGTCACATGACAGGGGTCCACTTAAACACGGAAGTAGGCCCC
GACATGTGACTCGTCACGTGTGTACACGTCACGACCGCCATTTTGTATAACAAA
ATGGCCGACTTCCTTCCTCTTTTTTGAAAAAAGGCGCGAAAAAACCGTCGGCGG
GGGGGCCGCGCGCTGCGCGCGCGGCCCCCGGGGAGGCAACGCCTCCCCCCCCC
GCGCGCATGCGCGCGGGTCCCCCCCCCTCCGGGGGGCTCCGCCCCCCGGCCCCC
```

-continued

CCCGT
;

GCTACGTCACTAACCTACGTGTCCGTCTCCTATAGGCCAGACACCGTCTACGTC    JA4
ATACACTTCCTGGGCATGGTCTACGTGATAATATAAGTGGCAGCACTTCCGAAT
GGCTGAGTTTTCCACGCCCGTCCGCGGAGAGGGAGCCACGGAGGGGATCCCGAA
CGTCCCGAGGGCGGGTGCCGAAGGTGAGTTTACACACCGCAGTCAAGGGGCAAT
TCGGGCTCGGGACTGGCCGGGCTATGGGCAAGGCTCTGAAAAATGCACTTTTCT
AGGTGTAGCAGAAAGAAAAGGACACTGTCACTGCTACCAGTGCACCCTTCACAG
AAAGCTAGGCCATCTGTGAGAGGTATGTGGAGACCCCCCAGGCGAAATGAATTC
ACTATTCAACGTAACTGGTTCTACAGTTGCTTTCACTCCCACTCTTCTATGTGT
GGCTGTACTGATTTTATTGGTCATTTCAATCACATCGCTGCTATGCTCGGCCGT
CCGGAAGACCAGAACCCTCCTCCGCCACCCGGGGCTGTGAGACCCCTACCTGCT
CTCCCGGCCGCCCCCGAGGCGCCCGGTGATCGAGCACCATGGCCTATGGGTGGT
GGCGCAGGCGACGAAGGCGCCCGTGGTGGAGGAGGAGATGGCGCCGCTGGAGAC
GCCGTCGGAGACCCCGCAGACGCCGACCTCGTCGCCGCTATCGACGCCGCAGAA
CAGTAAGGAGCGCGGCAGGGGGAGGTGGACTAAGAGATATAGACGATGGCGCC
GCAAAGGCAAACGCAAAGGCAAAAAAAAAATTATTATAAAACAATGGCAGCCCA
ACTACAGACGCAGATGCAACATAGTGGGCTACATGCCTCTACTTATATGTGGGG
AGAATACTGTTGCCAGAAACTATGCCACCCACTCAGACGACAGCTACTACCCTG
GACCCTTTGGGGGGGAATGACCGCAGACAAATTTACTCTAAGAATTCTATATG
ATGAATACAAGAGATTTATGAATTACTGGACAGCCTCAAACGAGGACCTAGACC
TGTGTAGATACCTAGGATGTACTTTATATGTATTTAGACACCCAGAAGTAGACT
TTATAATTATAATTAACACATCACCTCCATTTCTAGACACCGAGATAACAGGCC
CTAGCATACACCCGGGTATGATGGCCCTCAACAAACGAGTCAGATGGATACCTA
GCATAAAGAACAGACCAGGCAAAAAACACTATGTAAAGATTAAAGTGGGAGCCC
CCCGAATGTTCACAGATAAGTGGTACCCCCAGACAGACCTCTGTGACATGACAC
TCCTAACGATCTTTGCCTCTGCGGCGGATATGCAATATCCGTTCGGCTCACCAC
TAACTGACACTATAGTTGTGTCACTCCAAGTTCTGCAATCCATGTTCAACGACT
GCCTGAGTGTACTTCCTACTAACTTTGTAGAAACAACAGGCAAAGGCACACAAT
TACATAAGAAAATTATAAATCATTTACCGTACTACAACACCACACAAACACAAG
CACAATTTAAGAGATTTATAGAAAACAAAACTGCAACAAATGGAGACAATATAT
GGGCAAACTACATCAACACCGAAAAATTTAACAAAGAACAGTCACCTAAAAATG
ACAATGGCATAGGAGGTCCATACTGCACCTACTCAGACACATGGTACAAAGGCA
CAGCATACAACGAGAAAATTAAAAAGATACCTGAGGAGGCAAGCAAGCTATACT
ATGAAGAGACTAAACAATTAATAGGAATAACATTTACAGGATCCTCACACAGGT
TGCACTACTGCGGAGGCCTGTACTCCTCAGTATGGCTATCTGCAGGCAGATCGT
ACTTTGAAACCAAGGGTCCCTACACAGACATAACATACAACCCATTCTCAGACA
GAGGCGAAGGCAACATGCTGTGGATAGACTGGCTAACTAAAGRTACCTCAGTAT
ATGACAAAACACAGAGTAAATGTCTTATAGAAAACATGCCCTTGTGGGCGTCTG
TGTACGGATTCTCCGAGTACTGCAGTAAAGTAACAGGAGACACAAACATAGATC
ACAACTGCAGATGTGTTATTAGAAGCCCCTACACAGTGCCACAACTGTTAGATC

-continued

ACAACAACCCCCTSAGGGGATACGTACCGTACAGTTTTAACTTTGGAAATGGAA
AGATGCCAGGCGGCAGCAGCCAGGTACCCATTAGAATGAGAGCAAAGTGGTACC
CTACCCTCTTTCACCAAAAAGAAGTACTAGAAGCCTTAGCACAGTCGGGCCCCT
TTGCATATCACTCAGATATTAAAAAAGTGTCACTGGGCTTAAAATACAGATTTA
AGTGGGTGTGGGGTGGCAACCCCGTGTCCCAACAGGTTGTTAGGAACCCCTGCA
AGACCACCCAAGGTTCCTCGGGCAGTAGAGTGCCTCGATCAATACAAGTCGTTG
ACCCGCGGTACAACACACCAGAACTCACCATTCACGCGTGGGACTTCAGACATG
GGTTCTTTGGCAAAAAAGCTATTAAGCGAATGCAGGAGCAACCAATACCTCATG
ACACTTTTTCAGCAGGGTTCAAGCGCAGTCGCCGAGATACAGAAGCACTCCAAT
CCAGCCAAGAAGAGCACGAAAAAGAAAACTTACTTTTCCCAGTCCAGCAGCTCA
AGCGAGTCCCCCGTGGGAGACCTCGCAAGAGAGCCAAAGCGAGGAAGAAAACT
CGCAAAAACAGGAGACCCTCTCCCAGCAACTCAGAGACCAGCTGCACAAGCAGC
GGCTCATGGGAGAGCAACTCCGATCGCTCCTCTACCAAATGCAGAGGGTCCAAC
AAAATCAACACATAAACCCTATGTTATTGCCAAAGGGTCTGGCATTAACGTCTA
TTTCTCACAATGTAATATAGATATGTTTGGTGACCCCAAACCCTACAAGCCCTC
CTCCAATGACTGGGAGGAGGAGTACGAGGCCGCAAAGCACTGGGACAGACCCCC
CAGACACGACCTCAGAAGCACCCCCTTCTACCCCTGGGCCCCACCCCTAAACC
ATACAATGTCAACTTTGCCCTTAACTACAAATAAACGGTGGCCGTGGGAGTTTC
ACTTGTCGGTGTCTACCTCTTAAGGTCACTAAGCACTCCGAGCGTAAGCGAGGA
GTGCGACCCTCTACCAAGGGGCAACTCCCTCGAAGTCCGGCGCTACGCGCTTCG
CGCTGCGCCGGACATCTCGGACCCCCCCTCGACCCGAATCGCTTGCGCGATTCG
GACCTGCGGCCTCGGGGGGTCGGGGCTTTATTAAACAGACTCCGAGATGCCA
TTGGACACTGAGGGGGTGAACAGCAACGAAAGTGAGTGGGGCCAGACTTCGCCA
TAGGGCCTTTATCTTCTTGCCATTTGTCCGCGACCGGGGTCGCTCCTAGGCGC
GGACCCCGTTTCCGGGTCCTTCCGGGTTCCTCGGCGCCGTTCCAGTGACGTCAC
GGGCGCCATCTTAAGTGGCTGTCGCCGAGGATTGACGTCACAGTTCAAAGGTCA
TCCTCGGCGGTAACCGCAAAGATGGCGGTCAATCTCTTTCGGGTCAAAGGTCGC
GCATACGTCATAAGTCACATGTCTAGGGGTCCACTTAAACACGGAAGTAGGCCC
CGACATGTGACTCGTCACGTGTGTGCACGTCACGGCCGCCATTTTGTTTTACAA
AATGGCCGACTTCCTTCCTCTTTTTTAAAAAAAGGCGCCAAAAAACCGTCGGCG
GGGGGGCCGCGCGCTGCGCGCGCGGCCCCGGGGAGGCACAGCCTCCCCCCCC
CGCGCGCATGCGCGCGGGTCCCCCCCCCTCCGGGGGGCTCCGCCCCCCGGCCCC
CCCCGT
;

GCTACGTCACTAACCTACGTGTCCGTCTCCCATAGGCCGGACACTGTCTACGTC    US32
ATACACTTCCTGGGCATGGTCTACGTGATAATATAAGTAGCAGCACTTCCGAAT
GGCTGAGTTTTCTACGCCCGTCCGCGGAGAGGGAGCCACGGAGAGGATCCCGAA
CGTCCCGAGGGCGGGTGCCGGAGGTGAGTTTACACACCGGAGTCAAGGGGCAAT
TCGGGCTCGGGACTGGCCGGGCTATGGGCAAGGCTCTGAAAAATGCACTTTTCT
AGGTGTAGCAGAAAGAAAAGGACACTGTCACTGCTACCTCTGCACCCTTCACAG

-continued

```
AAAGCTAAGCCATCTGTGAGAGGTATGTGGAGACCCCCCAGGCGAAATGAATTC
ACTATTCAACGTAACTGGTTCTACAGTTGCTTTTACTCCCACTCTTCTATGTGT
GGCTGTCCTGATTTTATTGGTCATTTCAATCACATCGCTGCTATGCTCGGCCGT
CCGGAAGACCAGAACCCTCCTCCGCCACCCGGGGCTGTGAGACCCCTACCCGCT
CTCCCGGCCGCCCCGAGGCGCCCGGTGATCGAGCACCATGGCCTATGGGTGGT
GGCGCAGGCGACGAAGGCGCCCGTGGTGGAGGAGGAGATGGCGCCGCTGGAGAC
GCCGTCGGAGACCCCGCAGACGCCGACCTCGTCGCCGCTATCGACGCCGCAGAA
CAGTAAGGAGACGCGGCAGGGGAGGTGGACTAAGAGATATAGACGATGGCGCC
GCAAAGGCAAACGCAGAGGCAAAAAAAAAATTATTATAAAACAATGGCAGCCCA
ACTACAGACGCAGATGCAACATAGTGGGCTACATGCCTCTACTTATATGTGGGG
AAAATACTGTTGCCAGAAACTATGCCACCCACTCAGACGACAGCTACTACCCTG
GACCCTTTGGGGGGGAATGACCACAGACAAATTTACTTTAAGAATCCTATATG
ATGAATACAAGAGATTTATGAATTACTGGACAGCCTCAAACGAGGACCTAGACC
TGTGTAGATACCTAGGATGTACTCTATATGTATTTAGACACCCAGAAGTAGACT
TTATAATTATAATAAACACATCTCCTCCATTCCTAGACACAGAGATAACAGGCC
CTAGCATACACCCGGGTATGATGGCCCTCAACAAAAGAGCCAGATGGATACCTA
GCATAAAAACAGACCAGGCAGAAAACACTATGTGAAAATTAAAGTAGGAGCCC
CCCGAATGTTCACAGATAAGTAGTATCCCCAGACAGACCTCTGTGACATGACAC
TCCTAACGATCTTTGCCAGTGCGGCGGATATGCAATATCCGTTCGGCTCACCAC
TAACTGACACTATAGTTGTGTCATTCCAAGTTCTGCAATCCATGTACAACGACT
GCCTCAGTGTACTTCCTACTAACTTTACAGAAGGAACAGGCAAAGGCACACAAT
TACATGATAAAATTATTAATCATTTACCCTACAACACCACACAAACACAAG
CACAATTCAAGAGATTTATAGAAAACAAATCAGCAACAAATGGGACAATGTAT
GGCAAACTACATAAACAGCACAAAATTTAACACACAAGAATCACCTAAAAATG
ACAGTGGCATAGGAGGCCCATACTGCACATACGCAGATACATGGTACAAAGGCA
CAGCATACAATGAGAAAATTAAAAACATACCTAAACAAGCAAGCCAACTATACT
ATGAAGAAACTAAAAAATTAATTGGCATTACATTCACAGGATCCTCACACAGGT
TGCACTACTGCGGAGGCCTGTACTCCTCAGTATGGCTATCTGCAGGCAGATCAT
ACTTTGAAACCAAGGGTCCCTACACAGACATAACATACAACCCATTCTCAGACA
GAGGCGAAGGAAACATGCTGTGGATAGACTGGCTAACTAAAGATACCTCAGTAT
ATGACAAAATACAGAGTAAATGTCTTATACAAGACATGCCCTTATGGGCCTCTG
TATACGGATTCTCCGAGTACTGCAGTAAAGTAACAGGAGACACAAACATAGAAC
ACAACTGYAGATGTGTTATTAGGAGCCCCTACACAGTACCACAACTGTTAGATC
ACAACAACCCCCTCAGGGGATACGTACCCTACAGTTTTAACTTTGGAAATGGAA
AGATGCCGGCGGCAGCAGCCAGGTACCCATTAGAATGAGAGCAAAGTGGTACC
CTACCCTTTTTCACCAAAAAGAAGTACTAGAAGCCTTAGCACAGTCGGGCCCCT
TTGCATATCACTCAGATATTAAAAAAGTTTCACTGGGCTTAAAATACAGATTTA
AGTGGGTGTGGGGTGGCAACCCCGTGTCCCAACAGGTTGTTAGGAACCCCTGCA
AGACCACCCAAGGTTCCTCGGGCAGTAGAGTGCCTCGATCAATACAAGTCGTTG
ACCCGCGATACAACACACCAGAACTCACGATTCACGCGTGGGACTTCAGACATG
```

-continued

GGTTCTTTGGCAGAAAGGCTATTAAGCGAATGCAGGAACAACCAATACCTCATG
ACACTTTTTCAGCAGGGTTCAAGCGCAGTCGCCGAGATACAGAAGCACTCCAAT
GCAGCGAAGAAGACCTCCAAAAAGAAAACTTACTTTTCCCAGTCCAGCAGCTCA
AGCGAGTCCCCCCGTGGGAGACCTCGCAAGAGAGCCAAAGCGAGGAAGAAAACT
CGCAAAAACAGGAGACCCTCTCCCAGCAACTCAGAGACCAQCTGCACAAGCAGC
GGCTCATGGGAGAGCAACTCCGATCGCTCCTCTACCAAATGCAGAGGGTCCAAC
AAAATCAACACATAAACCCTATGTTATTGCCAAAGGGTCTGGCATTAACTTCTA
TTTCTCACAATGTAATATAGATATGTTTGGTGACCCCAAACCCTACAACCCCTC
CTCCAATGACTGGAAGGAGGAGTACGAGGCCGCAAAGTACTGGGACAGACCCCC
CAGACGCGACCTCAGGAGCACCCCTTTTACCCCTGGGCCCCACCCCCAAACC
ATACAATGTCAACTTTGCCCTCAACTACAAATAAACGGTGGCCGTGGGAGTTTC
ACTTGTCGGTGTCTACCTCTTAAGGTCACTAAGCACTCCGAGCGTAAGCGAGGA
GTGCGACCCTCTACCAAGGGGCAACTCCCTCGAAGTCCGGCGCTACGCGCTTCG
CGCTGCGCCGGACATCTCGGACCCCCCCTCGACCCGAATCGCTTGCGCGATTCG
GACCTGCGGCCTCGGGGGGGTCGGGAACTTTATTAAACGGACTCCGAGGTGCCA
TTGGACACTGAGGGGGTGAACAGCAACGAAAGTGAGTGGGGCCAGACTTCGCCA
TAGGGCCTTTATCTTCTTGCCATTTGTTCGCGACCGGGGTCGCTCCTAGGCGC
GGACCCCGTTTCGGGGTCCTTCCGGGTTCATCAGCGCCGTTCCAGTGACGTCAC
GAGCGCCATCTTAAGTGGCTGTCGCCGAGGATTGGCGTCACAGTTCAAAGGTCA
TCCTCGGCGGTAACCGCAAAGATGGCGGTCAATCTCYTTCAGGTCAAAGGTCGT
GCATACGTCATAAGTCACATGACAGGGGTCCACTTAAACACGGAAGTAGGCCCC
GACATGTGACTCGTCACGTGTGTACACGTCACGGCCGCAATTTTGTTTTACAAA
ATGGCCGACTTCCTTCCTCTTTTTTAAAAAAAGGCGCCAAAAAACCGTCGGCGG
GGGGGCCGCGCGCTGCGCGCGCGGCCCCCGGGGAGGCAAGGCCTCCCCCCCCC
GCGCGCATGCGCGCGGGTCCCCCCCCCTCCGGGGGGCTCCGCCCCCCGGCCCCC
CCCGT
;
GCTACGTCACTAACCGACGTGTCCGTCTCCTATAGGCCGGACACCGTCTACGTC    US35
ATACACTTCCTGGGCATGGTCTACGTGATAATATAAGTGGCAGCACTTCCAAAT
GGCTGAGTTTTCCACGCCCGTCCGCAGAGAGGGAGCCACGGAGGGGATCCCGAA
CGTCCCGAGGGCGGGTGCCGGAGGTGAGTTTACACACCGGAGTCAAGGGGCAAT
TCGGGCTCGGGACTGGCCGGGCTATGGGCAAGGCTCTTAAAAATGCACTTTTCT
AGGTGCAGTAGAAAGAAAAGGACACTGTCACTGCTACCACTGCACCATTCACAG
AAAGCTAGGCCATCTGTGAGAGGTATGTGGAGACCCCCGTGCGAAATGACTTC
ACTATTCAACGTAACTGGTTCTACAGTTGCTTTTACTCCCACACTTCTATGTGC
GGGTGTGCTGATTTTATTGGTCATTTCAATCACATCGCTGCTATGCTCGGCCGT
CCGGAAGACCAGAACCCTCCTCCGCCACCCGGGGCTCTGAGACCCCTACCCGCT
CCCCCGGCCGCCGCCGAGGCGCCCGGTGATCGAGCACCATGGCCTATCGGTGGT
GGTGGAGGCGACGGAGGCGCCCGTGGAGGAGGAGGAGATGGCGCCGCTGGAGAC
GTCGCCGGAGACCCCGCAGACGCCGACCTCGTCGCCGCTATCGACGCCGCAGAA
CAGTAAGGAGACGCGGCAGGGGGAGGTGGACTAGGAGATATAGACGATGGCGCC

```
GCAAGGGCAAACGCAGAGGCAAAAAAAAGATTATTATAAAACAGTGGCAGCCCA
ACTACACTCGGAGATGCAACATAGTGGGCTACCTACCTCTGCTAATCTGTGGAG
AAAATACTGTTGCTACAAACTATGCCACCCACTCAGACGACAGCTACTACCCCG
GACCCTTTGGGGGGGAATGACTACAGACAAATTTACTCTAAGAATACTGTATG
ATGAGTACAAGAGGTTTATGAACTACTGGACCGCCTCAAACGAGGACCTAGACC
TCTGTAGATACCTAGGACTTACTCTATATGTGTTTAGACACCCAGAAGTAGACT
TTATACTAACTATAAATACCTCCCCTCCATTTCTAGACACAGAAATAACAGGGC
CTAGCATACATCCAGGTATGATGGCCCTCAACAAAAGAGCCAGGTGGATACCTA
GCTTAAAAAACAGACCAGGCAGAAAGCACTATGTAAAGATTAAAGTGGGAGCCC
CCCGAATGTTCACAGATAAGTGGTACCCCAGACAGACCTCTGTGACATGACAC
TCCTAACGATCTTTGCCAGTGCGGCGGATATQCAATATCCGTTCGGCTCACCAC
TAACTGACACTATAGTTGTGTCATTCCAAGTTCTGCAATCCATGTACAACGACT
GCCTGAGCATACTTCCTGATAATTTTGTAGAACACACAGGCAAAGGCACCCAGC
TACATAAAAAAATAATACAACATTTACCCTACTACAACACCACACAAACACAAG
CACAATTTAAAAGAGTTGTAGAAAACATGTCAGCAACCAATGGAAACAATGTAT
GGGCAAACTACATAAATACTATAAAGTTCACAGACACACAAACTCCTGAAAATG
ATTCAGGCATAGGAGGCCCTTACACCAATTATTCAGACTCATGGTACAAAGGCA
CAGTATACAATAATAAAATTAAAGATATACCTGAAAAAGCAAGTAAATTATACT
ACGACCAAACCAAACAACTAATTGGCATTACATTTACAGGATCCACACACAGAC
TACACTACTGTGGAGGCCTATACTCTTCCGTATGGCTATCAGCAGGTAGATCCT
ACTTTGAAACGAAAGGCCCATACACAGACATCACTTACAACCCCTTTTCAGACA
GAGGAGAGGGTAATATGCTATGGATAGACTGGCTAACTAAAAATGACTCATCCT
ACTCAAAAACAAGTAGCAAGTGCCTCATAGAAAACTTACCCCTGTGGGCCTCAG
TATACGGATACAAAGAGTACTGCAGCAAAGTAACAGGAGATACAAACATAGAAC
ATAACTGCAGATGTGTTATCAGAAGCCCCTACACAGTACCACAGCTGTTAGACC
ACAACAATCCCCTCAGAGGTTACGTGCCTTATAGCCTCAACTTTGGAAATGGTA
AAATGCCAGGCGGTAGCAGCCTAGTACCCATTAGAATGAGAGCCAAGTGGTACC
CCACTCTGTTCCACCAAAAAGAAGTACTAGAGGCCATAGCACAGGCGGGTCCCT
TTGCATACCACTCAGACATTAAGAAAGTATCCCTGGGCATAAAGTACAGATTTA
AGTGGGTGTGGGTGGCAACCCCGTGTCCCAACAGGTTGTTAGAAACCCCTGCA
AGACCACCCAAGGTTCCTCGGGCAATAGAGTGCCTCGATCAATACAAGTCGTTG
ACCCGCGGTACAACACGCCAGAGCTCACCATACACGCGTGGGACTTCAGACATG
GGTTCTTTGGCAGAAAAGCTATTAAGAGAATGCAAGAACAACCAATACCTCATG
ACACTTTTTCAGCAGGGTTCAGGCGCAGTCGCCGAGATACAGAAGCACTCCAAT
GCAGCCAAGAAGAGCAACAAAAAGAAAACTTACTTTTCCCAGTCCAGCAGCTCA
AGCGAGTCCCCCCGTGGGAGACCTCGCAAGAGAGCCAAAGCGAGGAAGAAAACT
CGCAAAAACAGGAGACCCTCTCCCAGCAACTCAGAGACCAGCTGCACAAGCAGC
GGCTCATGGGAGAGCAACTCCGATCGCTCCTCTACCAAATGCAGAGGGTTCAAC
AAAATCAACACATAAACCCTATGTTATTGCCAAAGGGTCTGGCATTAACTTCTA
TTTCTCACAATGTAATATAGATATGTTTGGTGACCCCAAACCCTACAACCCCTC
```

-continued

```
CTCCAATGACTGGAAGGAGGAGTACCAGGCCGCAAAGTACTGGGACAGACCCCC

CAGACGCGACCTGAGGAGCACCCCCTTCTACCCCTGGGCCCCCACCCCCAAACC

ATACAATGTCAACTTTGCCCTCAACTACAAATAAACGGTGGCCGTGGGAGTTTC

ACTTGTCGGTGTCTACCTCTTAAGGTCACTAAGCACTCCGAGCGTAAGCGAGGA

GTGCGACCCTCTACCAAGGGGCAACTCCCTCGAAGTCCGGCGCTACGCGCTTCG

CGCTGCGCCGGACATCTCGGACCCCCCCTCGACCCGAATCGCTTGCGCGATTCG

GACCTGCGGCCTCGGGGGGTCGGGGCTTTATTAAACGGACTCCGAGGTGCCA

TTGGACACTGAGGGGTGGACAGCAACGAAAGTGAGTGGGCCAGACTTCGCCA

TAGGGCCTTTATCTTCTTGCCATTTGTCCGCGACCGGGGTCGCTCCTAGGCGC

GGACCCCGTTTCGGGGTCCTTCCGGGTTCGTCGGCGCCGTTCCAGTGACGTCAC

GGGCGCCATCTTAAGTGGCTGTCGCTGAGGATTGACGTCACAGTTCAAAGGTCA

TCCTCGGCGGTAACCGCAAAGATGGCGGTCAATCTCTTCCGGGTCAAAGGTCGT

GCATACGTCATAAGTCACATGACAGGAGTCCACTTAAACACGGAAGTAGGCCCC

GACATGTGACTCGTCACGTGTGTACACGTCACGGCCGCCATTTTGTTTTACAAA

ATGGCCGACTTCCTTCCTCTTTTTTAAAAAAAGGCGCGAAAAAACCGTCGGCGG

GGGGGCCGCGCGCTGCGCGCGCGGCCCCCGGGGGAGGCCACGCCTCCCCCCCCC

GCGCGCATGCGCGCGGGTCCCCCCCCCTCCGGGGGGCTCCGCCCCCCGGCCCCC

CCCGT
;

GCTGCACTTCCGAATGGCTGAGTTTTCCACGCCCGTCCGCAGCGGTGAAGCCAC   JA2B

GGAGGGAGCTCAGCGCGTCCCGAGGGCGGGTGCCGAAGGTGAGTTTACACACCG

GAGTCAAGGGGCAATTCGGGCTCGGGACTGGCCGGGCTATGGGCAAGGCTCTTA

AAAATGCACTTTTCTAGGATATCCAGGAAGAAAAGGCTACTGCTACTGCACACA

GTGCCAACTCCACAGAAAACTCTCAAACTTTTAAGAGGTATGTGGAGTCCTCCC

ACTGACGATGAACGTGTCCGCGAGCGAAAATGGTTTCTCGCAACTGTCTATTCT

CACTCTGCTTTCTGTGGCTGCAATGATCCTGTCGGTCACCTCTGTCGCCTGGCT

ACTCTCTCTAACCGTCCGGAGAACCCGGGACCCTCCGGGGGACGTCGTGCTCCT

TCGATCGGGGTCCTACCCGCTCTCCCGGCTGCTACCGAGCAGCCAGGTGATCGA

GCACCATGGCCTATGGGTGGTGGAGGAGACGCCGCAGAAGGTGGAAGAGATGGA

GGAGAAGGCCCAGGTGGAGACGCCCATGGAGGACCCGCAGACGCAGACCTGCTA

GACGCCGTGGACGCCGCGGAACAGTAAGGAGACGGAGGCGCGGGAGGTGGAGGA

GGCGCTATAGGAGGTGGAGGAGAAAGGGCAGACGCAGGAGAAAAAAGAAACTTA

TAATAAGACAATGGCAGCCAAACTATACCAGAAAGTGCAACATAGTAGGCTACA

TGCCAGTAATCATGTGTGGAGAAAACACTCTAATAAGAAACTATGCCACACACG

CAGACGACTGCTACTGGCCGGGACCCTTTGGGGGCGGCATGGCCACCCAGAAAT

TCACACCCAGAATCCTGTACGATGACTACAAGAGGTTTATGAACTACTGGACCT

CCTCAAACGAGGACCTAGACCTCTGTAGATACAGGGGAGTCACCCTGTACTTTT

TCAGACACCCAGATGTAGACTTTATCATCTTAATAAACACCACACCTCCATTCG

TAGATACAGAGATCACAGGACCCAGCATACATCCGGGCATGATGGCCCTGAACA

AGAGAGCCAGGTTCATCCCCAGCCTAAAGACTAGACCTGGCAGAAGACACATAG
```

-continued

```
TAAAGATTAGAGTGGGGCCCCCAAACTGTACGAGGACAAGTGGTACCCCCAGT
CAGAACTCTGTGACGTGCCCCTGCTAACCGTCTACGCGACCGCAGCGGATATGC
AATATCCGTTCGGCTCACCACTAACTGACACTCCTGTTGTAACCTTCCAAGTGT
TGCGCAGCATGTACAACGACGCCCTCAGCACACTTCCCTCTAACTTTGAAAACG
CAAGCAGTCCAGGCCAAAAACTTTACAAAGAAATATCTACATATTTACCATACT
ACAACACCACAGAAACAATAGCACAACTAAAGAGATATGTAGAAAATACAGAAA
AAAATGGCACAACGCCAAACCCGTGGCAATCAAAATATGTAAACACTACTGCCT
TCACCACTGCACTAAATGTTACAACTGAAAAACCATACACCACCTTCTCAGACA
GCTGGTACAGGGGCACAGTATACAAAGAAACAATCACTGAAGTGCCACTTGCCG
CAGCAAAACTCTATCAAAACCAAACAAAAAAGCTGCTGTCTACAACATTTACAG
GAGGGTCCGAGTACCTAGAATACCATGGAGGCCTGTACAGCTCCATATGGCTAT
CAGCAGGCCGATCCTACTTTGAAACAAAGGGAGCATACACAGACATCTGCTACA
ACCCCTACACAGACAGAGGAGAGGGCAACATGGTGTGGATAGACTGGCTATCAA
AAACAGACTCCAGATATGACAAAACCCGCAGCAAATGCCTTATAGAAAAGCTAC
CCCTATGGGCAGCAGTATACGGGTACCCAGAATACTGTGCCAAGAGCACCGGAG
ACTCAAACATAGACATGAACGCCAGAGTAGTAATAAGGTGCCCCTACACCGTCC
CCCAGATGATAGACACCAGCGACGAACTAAGGGGCTTCATAGTATACAGCTTTA
ACTTTGGCAGGGGCAAAATGCCCGGAGGCAGCAGCGAGGTACCCATAAGAATGA
GAGCCAAGTGGTACCCCTGCCTGTTTCACCAAAAAGAAGTTCTAGAAGCCTTGG
GACAGTCGGGCCCCTTCGCCTACCACTGCGACCAAAAAAAAGCAGTGCTAGGTC
TAAAATACAGATTTCACTGGATATGGGCGGAAGCCCCGTGTTTCCACAGGTTG
TTAGAAACCCTGCAAAGACACACACGGTTCCTCGGGCCCTAGAAAGCCTCGCT
CAATACAAATCATTGACCCGAAGTACAACACACCAGAGCTCACAATCCACGCGT
GGGATTTCAGACGTGGCTTCTTTGGCTCAAAAGCTATTAAAAGAATGCAACAAC
AACCAACAGATGCTGAACTTCTTCCACCAGGCCGCAAGAGGAGCAGGCGAGACA
CAGAAGCCCTCCAAAGCAGCCAAGAAAAGCAAAAAGAAAGCTTACTTTTCAAAC
ACCTCCAGCTCCAGCGACGAATACCCCCATGGGAAAGCTCGCAGGCCTCGCAGA
CAGAGGCAGAGAGCGAAAAAGAGCAAGAGGGCAGTCTCTCCCAGCAGCTCCGAG
AGCAGCTTTACCAGCAAAAGCTCCTCGGCAAGCAGCTCAGGGAAATGTTCCTAC
AACTCCACAAAATCCAACAAAATCAACACGTCAACCCTACCTTATTGCCAAGGG
ATCAGGCTTTAATCTGCTGGTCTCAGATTCAGTAATTAACATGTTTGGAGACCC
TAAACCATACAAACCCTCCAGCAACGACTGGAAAGAGGAGTACGAGGCCGCTAA
GTATTGGGACAGGCCCCCCAGATCTAACCTTAGAGATAACCCCTTCTATCCCTG
GGCCCCCCAAGCAATCCCTACAAAGTAAACTTTAAACTAGGCTTCCAATAAAG
CTAGGCCGTGGGAGTTTCACTTGTCGGTGTCTGCTTCTTAAGGTCGCCAAGCAC
TCCGAGCGTAAGCGAGGAGTGCGACCCTCCCCCCCGGTAGCAACTTCTTCGGAG
TCCGGCGCTACGCCTTCGGCTGCGCCGGACACCTCAGACCCCCCCTCCACCCGA
AACGCTTGCGCGTTTCGGACCTTCGGCGTCGGGGGGTCGGGAGCTTTATTAAA
CAGACTCCGAGTTGCCATTGGACACTGGAGCTGTGAATCAGTAACGAAAGTGAG
TGGGGCCAGACTTCGCCATAAGGCCTTTATCTTCTTGCCATTGGATGGTGGGA
```

-continued

GGGTCGCCATAGGCTTCAGCCTCGGTTTTAGGCCTTCCGGACTACAAAAATGGC

GGATTTCGTGACGTCACGGCCGCCATTTTAAGTCAGCGCTGGGGAGGCATGACT

GTAAGTTCAAAGGTCATCCTCACCGGAACTGACACAAAATGGCCGCCAATTTCT

TCCGGGTCAAAGGTCACGCCTACGTCATAGATGACGTAGGAGGGCGTACTCTGT

AAACACGGAAGTAGGCCCCGACACGTG
;

GCTGCACTTCCGAATGGCTGAGTTTTCCACGCCCGTCCGCAGCGGTGAAGCCAC    JA10

GGAGGGAGCTCAGCGCGTCCCGAGGGCGGGTGCCGGAGGTGAGTTTACACACCG

GAGTCAAGGGGCAATTCGGGCTCGGGACTGGCCGGGCTATGGGCAAGGCTCTTA

AAAATGCACTTTTCTAGGATATCCAGAAAGAAAAGGCTACTGCTACTGCAAACA

GAGCCAGCTCCACAGAAGACTCTCAAACTTTTAAAAGGTATGTGGAGTCCTCCC

ACTGACGATGAACGTGTCCGCGAGCGAAAATGGTTCCTCGCCACTGTTTATTCT

CACTCTGCTTTCTGTGGCTGCAATGATCCTGTCGGCCACCTCTGTCGCTTGGCT

ACTCTATCTAACCGTCCGGAGAACCCGGGACCCTCCGGGGACGTCGTGCTCCT

TCGATCGGGATCCTACCCGCTCTCCCGGCTGCTACCGAGCAGCCCGGTGATCGA

GCACCATGGCCTATGGGTGGTGGAGGAGACGCCGCAGAAGGTGGAAGAGATGGA

GGAGAAGGCCCAGGTGGAGACGCCCATGGAGGACCCGCAGACGCAGACCTGCTA

GACGCCGTGGACGCCGCAGAACAGTAAGGAGACGGAGGCGCGGGAGGTGGAGGA

GGCGCTATAGGAGGTGGAGGAGAAAGGGCAGACGCGGGAGAAAAAAGAAACTTA

TAATAAAACAATGGCAGCCAAACTATACCAGAGAGTGCAACATAGTAGGCTACA

TGCCAGTAATCATGTGTGGAGAGAACACTCTAATAAGAAACTATGCCACACACG

CAGACGACTGCTACTGGCCGGGACCCTTTGGGGCGGCATGGCCACCCAGAAAT

TCACACTCAGAATCCTGTACGATGACTACAAGAGGTTTATGAACTACTGGACCT

CCTCAAACGAGGACCTAGACCTCTGTAGATACAGGGGAGTCACCCTGTACTTTT

TCAGAAACCCAGATGTAGACTTTATCATCCTCATAAACACCACACCTCCGTTCG

TAGATACAGAGATCACAGGACCCAGCATACATCCGGGCATGATGQCCCTCAACA

AAAGAGCCAGGTTCATCCCCAGCCTAAAAACTAGACCTGGCAGAAGACACATAG

TAAAGATTAAAGTGGGGGCCCCCAAACTGTACGAGGACAAGTGGTACCCCCAGT

CAGAACTCTGTGACATGCCCCTACTAACCGTCTACGCCACCGCAGCGGATATGC

AATATCCGTTCGGCTCACCACTAACTGACACTCCTGTTGTAACCTTCCAAGTGT

TGCGCAGCATGTACAACGACGCCCTTAGCATACTTCCCTCTAACTTTCAAAGCC

CAGACAGTCCAGGCCAAAAACTTTACGAACAAATATCTAAGTATTTACCATACT

ACAACACCACAGAAACAATGGCACAACTAAAGAGATATATAGAAAATACAGAAA

AAAATACCACATCGCCAAACCCATGGCAAACAAAATATGTAAACACTACTGCCT

TCACCACTCCACAAACTGTTACAACTCAACAGCCATACACCAGCTTCTCAGACA

GCTGGTACAGGGCACAGTATACACAAACGAAATCACTAAGGTGCCACTTGCCG

CAGCAAAAGTGTATGAAACTCAAACAAAAAACCTGCTGTCTACAACATTTACAG

GAGGGTCAGAGTACCTAGAATACCATGGAGGCCTGTACAGCTCCATATGGCTAT

CAGCAGGCCGATCCTACTTTGAAACAAAGGGAGCATACACAGACATCTGCTACA

ACCCCTACACAGACAGAGGAGAGGGCAACATGGTGTGGATAGACTGGCTATCAA

AAACAGACTCCAGATATGACAAAACCCGCAGCAAATGCCTTATAGAAAAGCTAC

-continued

```
CCCTATGGGCAGCAGTATACGGGTACGCAGAATACTGTGCCAAGAGCACCGGAG
ACTCAAACATAGACATGAACGCCAGAGTAGTAATTAGGTGCCCCTACACCACCC
CCCAGATGATAGACACCAGCGACGAACTAAGGGGCTTCATAGTATACAGCTTTA
ACTTTGGCAGGGGCAAAATGCCCGGAGGCAGCAGCGAGGTACCCATTAGAATGA
GAGCCAAGTGGTACCCCTGCCTACTTCACCAAAAAGGAGTTCTAGAAGCCTTAG
GACAGTCAGGCCCCTTCGCCTACCACCGCGACCAAAAAAAAGCAGTGCTAGGTC
TAAAATACAGATTTCACTGGATATGGGGCGGAAACCCCGTGTTTCCACAGGTTG
TTAGAAACCCCTGCAAAGACACACACGGTTCCTCGGGCCCTAGAAAGCCTCGCT
CAATACAAATCATTGACCCGAAGTACAACACACCAGAGCTCACAATCCACGCGT
GGGATTTCAGACGTGGCTTCTTTGGCCCAAAAGCTATTAAGAGAATGCAACAAC
AACCAACAGATGCTGAACTTCTTCCACCAGGCCGCAAGAGGAGCAGGCGAGACA
CCGAAGCCCTCCAAAGCAGCCAAGAAAAGCAGAAAGAAAGCTTACTTTTCAAAC
AGCTCCAGCTCCGGCGACGAGTACCCCCGTGGGAAAGCTCGCAGGCCTCGCAGA
CAGAGGCAGAGAGCGAAAAAGAGCAAGAGGACAGTCTCTCCCAGCAGCTCCGAG
AGCAGCTTCACCAGCAAAAGCTCCTCGGCAAGCAGCTCAGGGAAATGTTCCTAC
AACTCCACAAAATCCAACAAAATCAACACGTCAACCCTACCCTATTGCCAAAAG
ATCAGGCTTTAATATGCTGGTCTCAGATTCAGTAATTAACATGTTCGGAGACCC
TAAACCATACAAACCCTCCAGCAACGACTGGAAAGAGGAGTACGAGGCCGCTAA
ATATTGGGACAGGCCCCCAGATTTGACCTTAGAGATAAGCCCTTCTATCCCTG
GGCCCCCCCAAGCAATCCCTACAAAGTAAACTTTAAACTAGGCTTTCAATAAAG
CTAGGCCGTGGGAGTTTCACTTGTCGGTGTCTGCTTCTTAAGGTCGCCAAGCAC
TCCGAGCGTAAGCGAGGAGTGCGACCCTCCCCCCCGGTAGCAACTTCTTCGGAG
TCCGGCGCTACGCCTTCGGCTGCGCCGGACACCTCAGACCCCCCCTCCACCCGA
AACGCTTGCGCGTTTCGGACCTTCGGCGTCGGGGGGTCGGGAGCTTTATTAAA
CAGACTCCGAGTTGCCATTGGACACTGGAGCTGTGAATCAGTAACGAAAGTGAG
TGGGGCCAGACTTCGCCATAAGGCCTTTATCTTCTTGCCATTTGTCAGTGTAGG
GGGTCGCCATAGGCTTCGGCCTCGTTTTTAGGCCTTCCGGACTACAAAAATGGC
AGATTCCGTGACGTCATGGCCGCCATTTTAAGTAAGGCGGAAGCAGCTGTCCCT
GTAACAAAATGGCGGCGACAGCCTTCCGCTTTGCACAAAATGGAGGTGTTTATC
TTCCGGGTCAAAGGTCACGCCTACGTCATAAGTCACGTGGGAGGGACCCGCTGC
GCATACACGGAAGTAGGCCCCGACACGTG
;
        GCTGCACTTCCGAATGGCTGAG      SetAforward1
        ;
        CCACCAGCCATAGGCCATGGTG      SetAreverse1
        ;
        GAGTTTTCCACGCCCGTCCGC       SetAforward2
        ;
        CCAGCCATAGGCCATGGTGCTC      SetAreverse2
        ;
        GTGGGACTTTCACTTGTCGGTGTC    SetBforward1
        ;
        GACAAATGGCAAGAAGATAAAGGCC   SetBreverse1
        ;
        AGGTCACTAAGCACTCCGAGCG      SetBforward2
        ;
        GCGAAGTCTGGCCCCACTCAC       SetBreverse2
        ;
```

-continued

```
CAGACTCCGAGTTGCCATTGGAC    SetCforward1
;
CACGTGTCGGGGCCTACTTCCG     SetCreverse1
;
GCAACGAAAGTGAGTGGGGCCAG    SetCforward2
;
GGTTTCCGCCGAGGATGACCT      SetCreverse2
```

We claim:

1. A probe or primer specific for TT virus selected from the group consisting of SEQ ID NO:29, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70 and SEQ ID NO:71.

2. The probe or primer of claim 1, wherein said probe or primer is selected from the group consisting of SEQ ID NO:60, SEQ ID NO:61, SEQ ID NO:62 and SEQ ID NO:63.

3. The probe or primer of claim 1, wherein said probe or primer is selected from the group consisting of SEQ ID NO:64, SEQ ID NO:65, SEQ ID NO:66, and SEQ ID NO:67.

4. The probe or primer of claim 1, wherein said probe or primer is selected from the group consisting of SEQ ID NO:68, SEQ ID NO:69, SEQ ID NO:70, and SEQ ID NO:71.

5. A method for detecting the presence of target TTV nucleotide sequences which may be present in a test sample comprising the steps of:
(a) contacting nucleic acids extracted from a test sample suspected of containing a target TTV nucleotide sequence with a TTV primer pair consisting of: 1) SEQ ID NO:60 and 2) a primer selected from the group consisting of SEQ ID NO:61, SEQ ID NO:63, SEQ ID NO:65, SEQ ID NO:67, SEQ ID NO:69 and SEQ ID NO:71 and amplifying said target TTV nucleotide sequence thus generating an amplified target TTV nucleotide sequence;
(b) contacting said amplified target TTV nucleotide sequence of step (a) with a TTV primer pair consisting of: 1) SEQ ID NO:62 and 2) a primer selected from the group consisting of SEQ ID NO:61, SEQ ID NO:63, SEQ ID NO:65, SEQ ID NO:67, SEQ ID NO:69 and SEQ ID NO:71, wherein said TTV primer pair hybridizes with said amplified target TTV nucleotide sequence of step (a) to generate an amplified product comprising said target TTV nucleotide sequence; and detecting the presence of said amplified product indicating the presence of the target TTV nucleotide sequence in said test sample.

6. The method of claim 5 wherein said primer pair of step (a) consists of SEQ ID NO:60 and SEQ ID NO:61, and said primer pair of step (b) consists of SEQ ID NO:62 and SEQ ID NO:63.

7. A method for detecting the presence of target TTV nucleotide sequences which may be present in a test sample comprising the steps of:
(a) contacting nucleic acids extracted from a test sample suspected of containing a target TTV nucleotide sequence with a TTV primer pair consisting of: 1) SEQ ID NO:64 and 2) a primer pair selected from the group consisting of SEQ ID NO:61, SEQ ID NO:63, SEQ ID NO:65, SEQ ID NO:67, SEQ ID NO:69 and SEQ ID NO:71 and amplifying said target TTV nucleotide sequence thus generating an amplified target TTV nucleotide sequence;
(b) contacting said amplified target TTV nucleotide sequence of step (a) with a TTV primer pair consisting of: 1) SEQ ID NO:66 and 2) a primer selected from the group consisting of SEQ ID NO:61, SEQ ID NO:63, SEQ ID NO:65, SEQ ID NO:67, SEQ ID NO:69 and SEQ ID NO:71, wherein said TTV primer pair hybridizes with said amplified target TTV nucleotide sequence of step (a) to generate an amplified product comprising said target TTV nucleotide sequence; and
(c) detecting the presence of said amplified product indicating the presence of the target TTV nucleotide sequence in said test sample.

8. The method of claim 7 wherein said primer pair of step (a) consists of SEQ ID NO:64 and SEQ ID NO:65, and said primer pair of step (b) consists of SEQ ID NO:66 and SEQ ID NO:67.

9. A method for detecting the presence of target TTV nucleotide sequences which may be present in a test sample comprising the steps of:
(a) contacting nucleic acids extracted from a test sample suspected of containing a target TTV nucleotide sequence with a TTV primer pair consisting of: 1) SEQ ID NO:68 and 2) a primer selected from the group consisting of SEQ ID NO:61, SEQ ID NO:63, SEQ ID NO:65, SEQ ID NO:67, SEQ ID NO:69 and SEQ ID NO:71 and amplifying said target TTV nucleotide sequence thus generating an amplified target TTV nucleotide sequence;
(b) contacting said amplified target TTV nucleotide sequence of step (a) with a TTV primer pair consisting of: 1) SEQ ID NO:70 and 2) a primer selected from the group consisting of SEQ ID NO:61, SEQ ID NO:63, SEQ ID NO:65, SEQ ID NO:67, SEQ ID NO:69 and SEQ ID NO:71, wherein said TTV primer pair hybridizes with said amplified target TTV nucleotide sequence of step (a) to generate an amplified product comprising said target TTV nucleotide sequence; and detecting the presence of said amplified product indicating the presence of the target TTV nucleotide sequence in said test sample.

10. The method of claim 9 wherein said primer pair of step (a) consists of SEQ ID NO:68 and SEQ ID NO:69, and said primer pair of step (b) consists of SEQ ID NO:70 and SEQ ID NO:71.

11. The method of claim 5, 7 or 9 wherein said test sample is obtained from a human or an animal.

12. A test kit for detecting a target TTV nucleotide sequence in a test sample, comprising:
(a) a container containing a primer pair specific for a target TTV nucleotide sequence, wherein said primer pair consists of: 1) SEQ ID NO:60 and 2) a primer selected from the group consisting of SEQ ID NO:61, SEQ ID NO:63, SEQ ID NO:65, SEQ ID NO:67, SEQ ID NO:69 and SEQ ID NO:71;
(b) a container containing a primer pair specific for a target TTV nucleotide sequence, wherein said primer pair consists of: 1) SEQ ID NO:62 and 2) a primer selected from the group consisting of SEQ ID NO:61, SEQ ID NO:63, SEQ ID NO:65, SEQ ID NO:67, SEQ ID NO:69 and SEQ ID NO:71.

13. The test kit of claim 12 wherein said primer pair of (a) consists of SEQ ID NO:60 and SEQ ID NO:61, and said primer pair of (b) consists of SEQ ID NO:62 and SEQ ID NO:63.

14. A test kit for detecting a target TTV nucleotide sequence in a test sample, comprising:
(a) a container containing a primer pair specific for a target TTV nucleotide sequence, wherein said primer pair consists of: 1) SEQ ID NO:64 and 2) a primer selected from the group consisting of SEQ ID NO:61, SEQ ID NO:63, SEQ ID NO:65, SEQ ID NO:67, SEQ ID NO:69 and SEQ ID NO:71;
(b) a container containing a primer pair specific for a target TTV nucleotide sequence, wherein said primer pair consists of: 1) SEQ ID NO:66 and 2) a primer selected from the group consisting of SEQ ID NO:61, SEQ ID NO:63, SEQ ID NO:65, SEQ ID NO:67, SEQ ID NO:69 and SEQ ID NO:71.

15. The test kit of claim 14 wherein said primer pair of (a) consists of SEQ ID NO:64 and SEQ ID NO:65, and said primer pair of (b) consists of SEQ ID NO:66 and SEQ ID NO:67.

16. A test kit for detecting a target TTV nucleotide sequence in a test sample, comprising:
   (a) a container containing a primer pair specific for a target TTV nucleotide sequence, wherein said primer pair consists of: 1) SEQ ID NO:68 and 2) a primer selected from the group consisting of SEQ ID NO:61, SEQ ID NO:63, SEQ ID NO:65, SEQ ID NO:67, SEQ ID NO:69 and SEQ ID NO:71;
   (b) a container containing a primer pair specific for a target TTV nucleotide sequence, wherein said primer pair consists of: 1) SEQ ID NO:70 and 2) a primer selected from the group consisting of SEQ ID NO:61, SEQ ID NO:63, SEQ ID NO:65, SEQ ID NO:67, SEQ ID NO:69 and SEQ ID NO:71.

17. The test kit of claim 16 wherein said primer pair of (a) consists of SEQ ID NO:68 and SEQ ID NO:69, and said primer pair of (b) consists of SEQ ID NO:70 and SEQ ID NO:71.

18. The test kit of claim 12, 14 or 16 wherein said test sample is obtained from a human or an animal.

19. A method of detecting TTV-infection in a tissue or organ prior to transplantation or xenotransplantation of said tissue or organ comprising the steps of:
   (a) contacting nucleic acids extracted from a biological sample from a tissue or organ suspected of containing a target TTV nucleotide sequence, from a potential donor human or animal, with a TTV primer pair represented by SEQ ID NO:60 and SEQ ID NO:61 and amplifying said target TTV nucleotide sequence thus generating an amplified target TTV nucleotide sequence;
   (b) contacting said amplified target TTV nucleotide sequence of step (a) with a TTV primer pair represented by SEQ ID NO:62 and SEQ ID NO:63 wherein said TTV primer pair hybridizes with said amplified target TTV nucleotide sequence of step (a) to generate an amplified product comprising said target TTV nucleotide sequence; and
   (c) detecting the presence of said, amplified product wherein the presence of the target TTV nucleotide sequence indicates TTV-infection in the biological sample and in said tissue or organ.

20. A method of detecting TTV-infection in a tissue or organ prior to transplantation or xenotransplantation of said tissue or organ comprising the steps of:
   (a) contacting nucleic acids extracted from a biological sample from said tissue or organ suspected of containing a target nucleotide sequence, from a potential donor human or animal, with a TTV primer pair represented by SEQ ID NO:64 and SEQ ID NO:65 and amplifying said target TTV nucleotide sequence thus generating an amplified target TTV nucleotide sequence;
   (b) contacting said amplified target TTV nucleotide sequence of step (a) with a TTV primer pair represented by SEQ ID NO:66 and SEQ ID NO:67 wherein said TTV primer pair hybridizes with said amplified target TTV nucleotide sequence of step (a) to generate an amplified product comprising said target TTV nucleotide sequence; and
   (c) detecting the presence of said amplified product wherein the presence of the target TTV nucleotide sequence indicates TTV-infection in the biological sample and in said tissue or organ.

21. A method of determining TTV-infection in a tissue or organ prior to transplantation or xenotransplantation of said tissue or organ comprising the steps of:
   (a) contacting nucleic acids extracted from a biological sample from said tissue or organ suspected of containing a target TTV nucleotide sequence, from a potential donor human or animal, with a TTV primer pair represented by SEQ ID NO:68 and SEQ ID NO:69 and amplifying said target TTV nucleotide sequence thus generating an amplified target TTV nucleotide sequence;
   (b) contacting said amplified target TTV nucleotide sequence of step (a) with a TTV primer pair represented by SEQ ID NO:70 and SEQ ID NO:71 wherein said TTV primer pair hybridizes with said amplified target TTV nucleotide sequence of step (a) to generate an amplified product comprising said target TTV nucleotide sequence; and
   (c) detecting the presence of said amplified product wherein the presence of the target TTV nucleotide sequence indicates TTV-infection in the biological sample and in said tissue or organ.

22. The method of claim 19, 20, or 21 wherein said biological sample is selected from at least one member of the group consisting of blood, tissue and an organ.

23. A method of detecting the presence of target TTV nucleotide sequences in a test sample, comprising the steps of:
   (a) contacting nucleic acids extracted from a test sample suspected of containing a target TTV nucleotide sequence with a primer pair represented by SEQ ID NO:60 and SEQ ID NO:61 and amplifying said target TTV nucleotide sequence thus generating an amplified target TTV nucleotide sequence;
   (b) contacting said amplified target TTV nucleotide sequence of step (a) with at least one TTV probe selected from the group consisting of SEQ ID NO:62 and SEQ ID NO:63 wherein said TTV primer probe hybridizes with said amplified target TTV nucleotide sequence of step (a) to generate an amplified product comprising said target TTV nucleotide sequence; and
   (c) detecting the presence of said amplified product indicating the presence of the target TTV nucleotide sequence in said test sample.

24. The method of claim 23, wherein said at least one probe is conjugated to a detectable signal-generating compound.

25. The method of claim 24 wherein said detectable signal generating compound is selected from the group consisting of a chemiluminescent compound, fluorescein and an enzyme.

26. The method of claim 23 wherein said at least one probe is conjugated to an antibody.

27. A method of detecting the presence of a target TTV nucleotide sequence in a test sample, comprising the steps of:
   (a) contacting nucleic acids extracted from a test sample suspected of containing a target TTV nucleotide sequence with a primer pair represented by SEQ ID NO:64 and SEQ ID NO:65 and amplifying said target TTV nucleotide sequence thus generating an amplified target TTV nucleotide sequence;

(b) contacting said amplified target TTV nucleotide sequence of step (a) with at least one TTV probe selected from the group consisting of SEQ ID NO:66 and SEQ ID NO:67 wherein said TTV primer probe hybridizes with said amplified target TTV nucleotide sequence of step (a) to generate an amplified product comprising said target TTV nucleotide sequence; and (c) detecting the presence of said amplified product indicating the presence of the target TTV nucleotide sequence in said test sample.

28. The method of claim 27, wherein said at least one probe is conjugated to a detectable signal-generating compound.

29. The method of claim 28 wherein said detectable signal generating compound is selected from the group consisting of a chemiluminescent compound, fluorescein and an enzyme.

30. The method of claim 27 wherein said at least one probe is conjugated to an antibody.

31. A method of detecting the presence of a target TTV nucleotide sequence in a test sample, comprising the steps of:

(a) contacting nucleic acids extracted from a test sample suspected of containing a target TTV nucleotide sequence with a primer pair represented by SEQ ID NO:68 and SEQ ID NO:69 and amplifying said target TTV nucleotide sequence thus generating an amplified target TTV nucleotide sequence;

(b) contacting said amplified target TTV nucleotide sequence of step (a) with at least one TTV probe selected from the group consisting of SEQ ID NO:70 and SEQ ID NO:71 wherein said TTV primer probe hybridizes with said amplified target TTV nucleotide sequence of step (a) to generate an amplified product comprising said target TTV nucleotide sequence; and detecting the presence of said amplified product indicating the presence of the target TTV nucleotide sequence in said test sample.

32. The method of claim 31, wherein said at least one probe is conjugated to a detectable signal-generating compound.

33. The method of claim 32, wherein said detectable signal generating compound is selected from the group consisting of a chemiluminescent compound, fluorescein and an enzyme.

34. The method of claim 31, wherein said at least one probe is conjugated to an antibody.

35. A method of detecting a target TTV nucleotide sequence which may be present in a test sample, comprising the steps of:

(a) contacting nucleic acids extracted from a test sample suspected of containing a target TTV nucleotide sequence with a TTV primer pair consisting of: 1) a primer selected from the group consisting of SEQ ID NO:60, SEQ ID NO:62, SEQ ID NO:64, SEQ ID NO:66, SEQ ID NO:68, and SEQ ID NO:70 and 2) a primer selected from the group consisting of SEQ ID NO:61, SEQ ID NO:63, SEQ ID NO:65, SEQ ID NO:67, SEQ ID NO:69, and SEQ ID NO:71 and amplifying said target TTV nucleotide sequence thus generating an amplified target TTV nucleotide sequence;

(b) contacting said amplified target TTV nucleotide sequence of step (a) with a TTV primer pair consisting of: 1) a primer selected from the group consisting of: SEQ ID NO:60, SEQ ID NO:62, SEQ ID NO:64, SEQ ID NO:66, SEQ ID NO:68, and SEQ ID NO:70, wherein said TTV primer pair hybridizes with said amplified target TTV nucleotide sequence of step (a) to generate an amplified product comprising said target TTV nucleotide sequence; and (b) detecting the presence of said amplified product indicating the presence of the target TTV nucleotide sequence in said test sample.

\* \* \* \* \*